(12) United States Patent
DeFrees et al.

(10) Patent No.: US 9,493,499 B2
(45) Date of Patent: Nov. 15, 2016

(54) PROCESS FOR THE PRODUCTION OF PURIFIED CYTIDINEMONOPHOSPHATE-SIALIC ACID-POLYALKYLENE OXIDE (CMP-SA-PEG) AS MODIFIED NUCLEOTIDE SUGARS VIA ANION EXCHANGE CHROMATOGRAPHY

(75) Inventors: Shawn DeFrees, North Wales, PA (US); Caryn Bowe, Doylestown, PA (US)

(73) Assignee: Novo Nordisk A/S (DK)

( * ) Notice: Subject to any disclaimer, the term of this patent is extended or adjusted under 35 U.S.C. 154(b) by 444 days.

(21) Appl. No.: 12/663,748

(22) PCT Filed: Jun. 12, 2008

(86) PCT No.: PCT/US2008/066749
§ 371 (c)(1),
(2), (4) Date: Mar. 2, 2010

(87) PCT Pub. No.: WO2008/154639
PCT Pub. Date: Dec. 18, 2008

(65) Prior Publication Data
US 2010/0174059 A1 Jul. 8, 2010

Related U.S. Application Data

(60) Provisional application No. 60/943,527, filed on Jun. 12, 2007, provisional application No. 60/968,274, filed on Aug. 27, 2007, provisional application No. 60/970,247, filed on Sep. 5, 2007.

(51) Int. Cl.
*C07H 19/10* (2006.01)
(52) U.S. Cl.
CPC ..................................... *C07H 19/10* (2013.01)
(58) Field of Classification Search
CPC ........ C07H 19/00; C07H 1/06; C07H 21/00; C07H 19/10; C07H 19/20
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,704,361 A | 11/1987 | Miccoli et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,904,584 A | 2/1990 | Shaw |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |
| 5,278,299 A | 1/1994 | Wong et al. |
| 5,281,698 A | 1/1994 | Nitecki |
| 5,288,637 A | 2/1994 | Roth |
| 5,308,460 A | 5/1994 | Mazid et al. |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |

(Continued)

FOREIGN PATENT DOCUMENTS

| | | |
|---|---|---|
| AU | 1991/083760 A | 3/1992 |
| AU | 1992/017052 | 12/1992 |

(Continued)

OTHER PUBLICATIONS

GE Healthcare, Ion Exchange Chromatography, Principles and Methods, 2004, 27 pages.*

(Continued)

*Primary Examiner* — Shaojia Anna Jiang
*Assistant Examiner* — Dale R Miller
(74) *Attorney, Agent, or Firm* — Leydig, Voit & Mayer, Ltd.

(57) ABSTRACT

The current invention provides methods (e.g., large-scale processes) for the production of nucleotide sugars, which are modified with a polymeric modifying group, such as poly (alkylene oxide) moieties (e.g., poly(ethylene glycol) or poly(propylene glycol)) moieties. A typical process of the invention includes anion exchange chromatography followed by an ultrafiltration procedure, such as tangential flow filtration. The process of the invention provides modified nucleotide sugars in unexpectedly high purity and high overall yields.

24 Claims, 8 Drawing Sheets

(56) References Cited

U.S. PATENT DOCUMENTS

| | | |
|---|---|---|
| 5,352,670 A | 10/1994 | Venot et al. |
| 5,369,017 A | 11/1994 | Wong et al. |
| 5,374,541 A | 12/1994 | Wong et al. |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer et al. |
| 5,409,817 A | 4/1995 | Ito et al. |
| 5,410,016 A | 4/1995 | Hubbell et al. |
| 5,432,059 A | 7/1995 | Bean et al. |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,580,560 A | 12/1996 | Nicolaisen et al. |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,639 A | 10/1998 | Berkner |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | DeFrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden et al. |
| 5,997,864 A | 12/1999 | Hart et al. |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,156,547 A | 12/2000 | Roth |
| 6,166,183 A | 12/2000 | Ishikawa et al. |
| 6,183,738 B1 | 2/2001 | Clark |
| 6,188,738 B1 | 2/2001 | Sakamoto et al. |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,379,933 B1 | 4/2002 | Johnson et al. |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,008,252 B2 | 8/2011 | DeFrees et al. |
| 8,053,410 B2 | 11/2011 | Klausen et al. |
| 8,063,015 B2 | 11/2011 | DeFrees et al. |
| 8,076,292 B2 | 12/2011 | DeFrees et al. |
| 8,178,108 B2 | 5/2012 | Buechler et al. |
| 8,207,112 B2 | 6/2012 | Hinderer et al. |
| 8,247,381 B2 | 8/2012 | DeFrees |
| 8,268,967 B2 | 9/2012 | DeFrees et al. |
| 8,361,961 B2 | 1/2013 | DeFrees et al. |
| 8,404,809 B2 | 3/2013 | DeFrees et al. |
| 8,632,770 B2 | 1/2014 | DeFrees et al. |
| 8,633,157 B2 | 1/2014 | DeFrees et al. |
| 8,633,300 B2 | 1/2014 | Ostergaard et al. |
| 8,716,239 B2 | 5/2014 | DeFrees et al. |

(56) References Cited

U.S. PATENT DOCUMENTS

| | | |
|---|---|---|
| 8,716,240 B2 | 5/2014 | DeFrees et al. |
| 8,791,066 B2 | 7/2014 | DeFrees |
| 8,791,070 B2 | 7/2014 | DeFrees et al. |
| 8,841,439 B2 | 9/2014 | Felo et al. |
| 8,853,161 B2 | 10/2014 | DeFrees et al. |
| 8,911,967 B2 | 12/2014 | DeFrees et al. |
| 8,916,360 B2 | 12/2014 | DeFrees et al. |
| 8,969,532 B2 | 3/2015 | DeFrees et al. |
| 9,005,625 B2 | 4/2015 | DeFrees et al. |
| 9,023,992 B2 | 5/2015 | Rasmussen et al. |
| 9,029,331 B2 | 5/2015 | DeFrees et al. |
| 9,050,304 B2 | 6/2015 | Zopf et al. |
| 9,187,532 B2 | 11/2015 | DeFrees |
| 9,187,546 B2 | 11/2015 | DeFrees |
| 9,200,049 B2 | 12/2015 | DeFrees |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0127682 A1 | 9/2002 | Gotschlich |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda |
| 2002/0182586 A1 | 12/2002 | Morris et al. |
| 2003/0003529 A1 | 1/2003 | Bayer |
| 2003/0027257 A1 | 2/2003 | Iatrou et al. |
| 2003/0040037 A1 | 2/2003 | Bayer |
| 2003/0044908 A1 | 3/2003 | Persson |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0043464 A1 | 3/2004 | Gotschlich |
| 2004/0063911 A1 | 4/2004 | DeFrees et al. |
| 2004/0077836 A1 | 4/2004 | DeFrees et al. |
| 2004/0082024 A1 | 4/2004 | Brandstadt et al. |
| 2004/0082026 A1 | 4/2004 | DeFrees et al. |
| 2004/0082038 A1 | 4/2004 | Lee et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0032742 A1 | 2/2005 | DeFrees et al. |
| 2005/0058620 A1 | 3/2005 | Nakamoto et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | DeFrees |
| 2006/0182714 A1 | 8/2006 | Behrens et al. |
| 2006/0183198 A1 | 8/2006 | Buechler et al. |
| 2006/0198819 A1 | 9/2006 | Behrens et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0244301 A1 | 10/2007 | Siekmann et al. |
| 2007/0254834 A1 | 11/2007 | DeFrees et al. |
| 2007/0254836 A1 | 11/2007 | DeFrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |

(56) References Cited

U.S. PATENT DOCUMENTS

| | | |
|---|---|---|
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0261872 A1 | 10/2010 | DeFrees et al. |
| 2010/0286067 A1 | 11/2010 | DeFrees |
| 2010/0322940 A1 | 12/2010 | Bayer |
| 2010/0330060 A1 | 12/2010 | DeFrees et al. |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0064719 A1 | 3/2011 | Rasmussen et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |
| 2013/0344050 A1 | 12/2013 | DeFrees et al. |
| 2014/0112903 A1 | 4/2014 | DeFrees et al. |
| 2014/0294762 A1 | 10/2014 | DeFrees et al. |
| 2015/0111245 A1 | 4/2015 | DeFrees et al. |
| 2015/0258206 A1 | 9/2015 | DeFrees et al. |
| 2015/0274847 A1 | 10/2015 | DeFrees et al. |
| 2015/0343080 A1 | 12/2015 | DeFrees et al. |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2397347 A1 | 8/2001 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 154316 A2 | 9/1985 |
| EP | 0200421 A2 | 12/1986 |
| EP | 0370205 A2 | 5/1990 |
| EP | 0459630 A2 | 12/1991 |
| EP | 0474313 A2 | 3/1992 |
| EP | 0475354 A2 | 3/1992 |
| EP | 0577580 A2 | 1/1994 |
| EP | 0585109 A2 | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 A1 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H02-076894 A | 3/1990 |
| JP | H03-503759 A | 8/1991 |
| JP | H06-086684 A | 3/1994 |
| JP | H06-105692 A | 4/1994 |
| JP | H06-160365 A | 6/1994 |
| JP | H06-172375 A | 6/1994 |
| JP | H06-504678 A | 6/1994 |
| JP | 07-107979 A | 4/1995 |
| JP | H07-196925 A | 8/1995 |
| JP | H07-223921 A | 8/1995 |
| JP | H08-506023 A | 7/1996 |
| JP | H09503905 | 4/1997 |
| JP | H09-208461 A | 8/1997 |
| JP | H10-307356 A | 11/1998 |
| JP | 2000-501607 A | 2/2000 |
| JP | 2001-061479 A | 3/2001 |
| JP | 2001-508783 A | 7/2001 |
| JP | 2001-519784 A | 10/2001 |
| JP | 2002-536018 A | 10/2002 |
| JP | 2003-516731 A | 5/2003 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 87/00056 A1 | 1/1987 |
| WO | WO 87/05330 A1 | 9/1987 |
| WO | 88/10295 A1 | 12/1988 |
| WO | WO 89/06546 A1 | 7/1989 |
| WO | WO 89/10134 A1 | 11/1989 |
| WO | WO 90/07572 A1 | 7/1990 |
| WO | WO 90/08164 A1 | 7/1990 |
| WO | WO 90/08823 A1 | 8/1990 |
| WO | WO 90/12090 A1 | 10/1990 |
| WO | WO 90/13540 A1 | 11/1990 |
| WO | WO 91/06635 A1 | 5/1991 |
| WO | WO 91/09122 | 6/1991 |
| WO | 91/11514 A1 | 8/1991 |
| WO | WO 91/14697 A1 | 10/1991 |
| WO | WO 92/01055 A1 | 1/1992 |
| WO | WO 92/15686 A1 | 9/1992 |
| WO | 92/16555 A1 | 10/1992 |
| WO | WO 92/16555 A1 | 10/1992 |
| WO | WO 92/16640 A1 | 10/1992 |
| WO | WO 92/18135 A1 | 10/1992 |
| WO | WO 92/22310 A1 | 12/1992 |
| WO | WO 93/08842 A1 | 5/1993 |
| WO | WO 93/13198 A1 | 7/1993 |
| WO | WO 93/15189 A1 | 8/1993 |
| WO | WO 93/18787 A1 | 9/1993 |
| WO | WO 94/04193 A1 | 3/1994 |
| WO | WO 94/05332 A2 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/25614 A1 | 11/1994 |
| WO | WO 94/25615 A1 | 11/1994 |
| WO | WO 94/26760 A1 | 11/1994 |
| WO | WO 94/27631 A1 | 12/1994 |
| WO | WO 94/28024 A1 | 12/1994 |
| WO | WO 95/02421 A1 | 1/1995 |
| WO | 95/04816 A1 | 2/1995 |
| WO | WO 95/04278 A1 | 2/1995 |
| WO | WO 95/05465 A1 | 2/1995 |
| WO | WO 96/10089 A1 | 4/1996 |
| WO | WO 96/11953 A1 | 4/1996 |
| WO | WO 96/12800 A1 | 5/1996 |
| WO | WO 96/21468 A1 | 7/1996 |
| WO | WO 96/21469 A1 | 7/1996 |
| WO | 96/32492 A1 | 10/1996 |
| WO | WO 96/32491 A1 | 10/1996 |
| WO | WO 96/32492 A1 | 10/1996 |
| WO | WO 96/34015 A1 | 10/1996 |

(56) References Cited

FOREIGN PATENT DOCUMENTS

| | | |
|---|---|---|
| WO | WO 96/36357 A1 | 11/1996 |
| WO | WO 96/40731 A1 | 12/1996 |
| WO | WO 96/40881 A1 | 12/1996 |
| WO | WO 97/05330 A1 | 2/1997 |
| WO | WO 97/21822 A2 | 6/1997 |
| WO | WO 97/47651 A1 | 12/1997 |
| WO | WO 98/05363 A2 | 2/1998 |
| WO | WO 98/31826 A1 | 7/1998 |
| WO | WO 98/32466 A1 | 7/1998 |
| WO | WO 98/41562 A1 | 9/1998 |
| WO | WO 98/51784 A1 | 11/1998 |
| WO | WO 98/58964 A1 | 12/1998 |
| WO | 99/03887 A1 | 1/1999 |
| WO | WO 99/00150 A2 | 1/1999 |
| WO | WO 99/13063 A1 | 3/1999 |
| WO | WO 99/14259 A1 | 3/1999 |
| WO | WO 99/22764 A1 | 5/1999 |
| WO | WO 99/28491 A1 | 6/1999 |
| WO | WO 99/34833 A1 | 7/1999 |
| WO | WO 99/37779 A1 | 7/1999 |
| WO | WO 99/45964 A1 | 9/1999 |
| WO | WO 99/48515 A1 | 9/1999 |
| WO | WO 99/54342 A1 | 10/1999 |
| WO | WO 99/55376 A1 | 11/1999 |
| WO | WO 00/23114 A2 | 4/2000 |
| WO | WO 00/26354 A1 | 5/2000 |
| WO | WO 00/29558 A1 | 5/2000 |
| WO | WO 00/29603 A2 | 5/2000 |
| WO | 00/47741 A2 | 8/2000 |
| WO | WO 00/44785 A1 | 8/2000 |
| WO | WO 00/46379 A1 | 8/2000 |
| WO | WO 00/65087 A1 | 11/2000 |
| WO | WO 01/02017 A2 | 1/2001 |
| WO | WO 01/05434 A2 | 1/2001 |
| WO | WO 01/19955 A2 | 3/2001 |
| WO | 01/36640 A2 | 5/2001 |
| WO | WO 01/39788 A2 | 6/2001 |
| WO | WO 01/49830 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | 01/68565 A2 | 9/2001 |
| WO | WO 01/76640 A2 | 10/2001 |
| WO | WO 01/83725 A1 | 11/2001 |
| WO | WO 01/87329 A1 | 11/2001 |
| WO | WO 01/87925 A2 | 11/2001 |
| WO | WO 01/88117 A2 | 11/2001 |
| WO | 02/03075 A2 | 1/2002 |
| WO | WO 02/02597 A2 | 1/2002 |
| WO | WO 02/02764 A2 | 1/2002 |
| WO | WO 02/13843 A2 | 2/2002 |
| WO | WO 02/13873 A2 | 2/2002 |
| WO | WO 02/29025 A2 | 4/2002 |
| WO | WO 02/44196 A1 | 6/2002 |
| WO | WO 02/49673 A2 | 6/2002 |
| WO | WO 02/50099 A2 | 6/2002 |
| WO | WO 02/053580 A2 | 7/2002 |
| WO | WO 02/074806 A2 | 9/2002 |
| WO | WO 02/077218 A1 | 10/2002 |
| WO | WO 02/092619 A2 | 11/2002 |
| WO | WO 03/006501 A2 | 1/2003 |
| WO | WO 03/011879 A1 | 2/2003 |
| WO | WO 03/017949 A2 | 3/2003 |
| WO | 03/027147 A2 | 4/2003 |
| WO | 03/031464 A2 | 4/2003 |
| WO | WO 03/029291 A2 | 4/2003 |
| WO | WO 03/031464 A2 | 4/2003 |
| WO | 03/037932 A2 | 5/2003 |
| WO | WO 03/045980 A2 | 6/2003 |
| WO | WO 03/046150 A2 | 6/2003 |
| WO | WO 03/093448 A2 | 11/2003 |
| WO | WO 2004/000366 A1 | 12/2003 |
| WO | WO 2004/009838 A2 | 1/2004 |
| WO | WO 2004/010327 A2 | 1/2004 |
| WO | WO 2004/014417 A2 | 2/2004 |
| WO | WO 2004/022004 A2 | 3/2004 |
| WO | WO 2004/029090 A1 | 4/2004 |
| WO | WO 2004/029091 A2 | 4/2004 |
| WO | WO 2004/033651 A2 | 4/2004 |
| WO | WO 2004/046222 A1 | 6/2004 |
| WO | WO 2004/047858 A1 | 6/2004 |
| WO | 2004/067566 A1 | 8/2004 |
| WO | WO 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/093823 A2 | 11/2004 |
| WO | WO 2004/096148 A2 | 11/2004 |
| WO | WO 2004/099231 A2 | 11/2004 |
| WO | WO 2004/101597 A2 | 11/2004 |
| WO | WO 2004/101740 A2 | 11/2004 |
| WO | WO 2004/103275 A2 | 12/2004 |
| WO | WO 2004/106373 A1 | 12/2004 |
| WO | WO 2005/001025 A2 | 1/2005 |
| WO | WO 2005/003171 A2 | 1/2005 |
| WO | 2005/014035 A2 | 2/2005 |
| WO | WO 2005/012484 A2 | 2/2005 |
| WO | WO 2005/014024 A2 | 2/2005 |
| WO | WO 2005/014035 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005072371 * | 8/2005 |
| WO | WO2005072371 A * | 8/2005 |
| WO | WO 2005/079363 A2 | 9/2005 |
| WO | WO 2005/091944 A2 | 10/2005 |
| WO | WO 2005/121331 A2 | 12/2005 |
| WO | WO 2006/005058 A2 | 1/2006 |
| WO | WO 2006/010143 A2 | 1/2006 |
| WO | 2006/016168 A2 | 2/2006 |
| WO | WO 2006/011839 A1 | 2/2006 |
| WO | WO 2006/013202 A2 | 2/2006 |
| WO | WO 2006/014349 A2 | 2/2006 |
| WO | WO 2006/014466 A2 | 2/2006 |
| WO | WO 2006/018204 A1 | 2/2006 |
| WO | WO 2006/020372 A2 | 2/2006 |
| WO | WO 2006/031811 A2 | 3/2006 |
| WO | WO 2006/035057 A1 | 4/2006 |
| WO | WO 2006/050247 A2 | 5/2006 |
| WO | WO 2006/053299 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | 2006/082517 A1 | 8/2006 |
| WO | WO 2006/103298 A2 | 10/2006 |
| WO | WO 2006/105426 A2 | 10/2006 |
| WO | 2006/119987 A2 | 11/2006 |
| WO | WO 2006/121569 A2 | 11/2006 |
| WO | WO 2006/127910 A2 | 11/2006 |
| WO | WO 2006/134173 A2 | 12/2006 |
| WO | WO 2007/022512 A2 | 2/2007 |
| WO | 2007/056191 A1 | 5/2007 |
| WO | WO 2007/056191 A2 | 5/2007 |
| WO | WO 2007/135182 A2 | 11/2007 |
| WO | WO 2008/011633 A2 | 1/2008 |
| WO | 2008/025856 A2 | 3/2008 |
| WO | WO 2008/057683 A2 | 5/2008 |
| WO | WO 2008/060780 A2 | 5/2008 |
| WO | WO 2008/073620 A2 | 6/2008 |
| WO | 2008/116633 A3 | 10/2008 |
| WO | WO 2008/124406 A2 | 10/2008 |
| WO | WO 2008/151258 A2 | 12/2008 |
| WO | WO 2008/154639 A2 | 12/2008 |

(56) References Cited

FOREIGN PATENT DOCUMENTS

| WO | WO 2009/089396 A2 | 7/2009 |
|----|-------------------|--------|
| WO | 2011/101242 A1 | 8/2011 |
| WO | 2014/060397 A1 | 4/2014 |

OTHER PUBLICATIONS

Räbinä, J., Mäki, M., Savilahti, E. M., Järvinen, N., Penttilä, L., & Renkonen, R. (2001). Analysis of nucleotide sugars from cell lysates by ion-pair solid-phase extraction and reversed-phase high-performance liquid chromatography. Glycoconjugate journal, 18(10), 799-805.*
Monfardini, C., Schiavon, O., Caliceti, P., Morpurgo, M., Harris, J. M., & Veronese, F. M. (1995). A branched monomethoxypoly (ethylene glycol) for protein modification. Bioconjugate chemistry, 6(1), 62-69.*
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.

(56) References Cited

OTHER PUBLICATIONS

Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.

(56) References Cited

OTHER PUBLICATIONS

Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 3, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Abeijon et al., *J. Biol. Chem.*, 261(24): 11374-11377 (1986).
Abuchowski et al., *J. Biol. Chem.*, 252(11): 3578-3581 (1977).
Abuchowski et al., *J. Biol. Chem.*, 252(11): 3582-3586 (1977).
Abuchowski et al., *Cancer Biochem. Biophys.*, 7(2): 175-186 (1984).
Adelhorst et al., *J. Biol. Chem.*, 269(9): 6275-6278 (1994).
Ailor et al., *Glycobiology*, 10(8): 837-847 (2000).
Alam et al., *J. Biotechnol.*, 65(2-3): 183-190 (1998).
Allegre et al., *J. Memb. Sci.*, 269(1-2): 109-117 (2006).
Altmann et al., *Glycoconj. J.*, 16(2): 109-123 (1999).
Amersham Pharmacia Biotech, "Hydrophobic Interaction Chromatography: Principles and Methods," 104 pp. (2000).
Aplin et al., *CRC Crit. Rev. Biochem.*, 10(4): 259-306 (1981).
Barrios et al., *J. Mol. Recognit.*, 17(4):332-338 (2004).
Beauchamp et al., *Anal. Biochem.*, 131(1): 25-33 (1983).
Bedard et al., *Cytotechnology*, 15(1-3):129-138 (1994).
Bennett et al., *J. Biol. Chem.*, 273(46): 30472-30481 (1998).
Bennett et al., *FEBS Lett.*, 460(2): 226-230 (1999).
Berger et al., *Blood*, 71(6): 1641-1647 (1988).
Berg-Fussman et al., *J. Biol. Chem.*, 268(20): 14861-14866 (1993).
Bhadra et al., *Pharmazie*, 57(1): 5-29 (2002).
Bhatia et al., *Anal. Biochem.*, 178(2): 408-413 (1989).
Bickel et al., *Adv. Drug Deliv. Rev.*, 46(1-3): 247-279 (2001).
Bijsterbosch et al., *Eur. J. Biochem.*, 237(2): 344-349 (1996).
Bjoern et al., *J. Biol. Chem.*, 266(17): 11051-11057 (1991).
Boccu et al., *Z. Naturforsch.*, 38c: 94-99 (1983).
Boime et al., *Recent Prog. Horm. Res.*, 54: 271-289 (1999).
Boissel et al., *J. Biol. Chem.*, 268(21): 15983-15993 (1993).
Bork et al., *Trends Genet.*, 12(10): 425-427 (1996).
Bork, *Genome Res.*, 10(4): 398-400 (2000).
Bouizar et al., *Eur. J. Biochem.*, 155(1): 141-147 (1986).
Boyd et al., *Mol. Immunol.*, 32(17-18): 1311-1318 (1995).
Brenner, *Trends Genet.*, 15(4): 132-133 (1999).
Brockhausen et al., *Acta Anatomica*, 161: 36-78 (1998).
Brockhausen et al., *Glycoconj. J.*, 15: 595-603 (1998).
Broun et al., *Science*, 282(5392): 1315-1317 (1998).
Browning et al., *J. Immunol.*, 143(6): 1859-1867 (1989).
Brumeanu et al., *J. Immunol. Meth.*, 183: 185-197 (1995).
Bückmann et al., *Makromol. Chem.*, 182(5): 1379-1384 (1981).
Burns et al., *Blood*, 99(12): 4400-4405 (2002).
Butnev et al., *Biol. Reprod.*, 58(2): 458-469 (1998).
Byun et al., *ASAIO J.*, 38(3): M649-M653 (1992).
Casares et al., *Nat. Biotechnol.*, 19(2): 142-147 (2001).
Chaffee et al., *J. Clin. Invest.*, 89(5): 1643-1651 (1992).
Charter et al., *Glycobiology*, 10(10): 1049-1056 (2000).
Chern et al., *Eur. J. Biochem.*, 202(2): 225-229 (1991).
Chiba et al., *Biochem. J.*, 308(2): 405-409 (1995).
Chrisey et al., *Nucleic Acids Res.*, 24(15): 3031-3039 (1996).
Clark et al., *J. Biol. Chem.*, 271(36): 21969-21977 (1996).
Cohn et al., *J. Biomed. Mater. Res,.* 22(11): 993-1009 (1988).
Cointe et al., *Glycobiology*, 10(5): 511-519 (2000).
Conradt et al., *J. Biol. Chem.*, 262(30): 14600-14605 (1987).
Cope et al., *Mol. Microbiol.*, 5(5): 1113-1124 (1991).
Copeland, "Enzymes: A Practical Introduction to Structure, Mechanism and Data Analysis" 2nd ed., Wiley-VCH, New York, pp. 146-150 (2000).
Costa et al., *J. Biol. Chem.*, 272(17): 11613-11621 (1997).
Crout et al., *Curr. Opin. Chem. Biol.*, 2(1): 98-111 (1998).
Culajay et al., *Biochem.*, 39: 7153-7158 (2000).
Deacon, *Diabetes*, 54: 2181-2189 (2004).
DeFrees et al., *Glycobiology*, 16(9): 833-843 (2006).
Delgado et al., *Biotechnol. Appl. Biochem.*, 12(2): 119-128 (1990).
Delgado et al., *Crit. Rev. Ther. Drug Carrier Syst.*, 9(3-4): 249-304 (1992).
De Vries et al, *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Doerks et al., *Trends Genet.*, 14(6): 248-250 (1998).
Douglas et al., *J. Am. Chem. Soc.*, 113(13): 5095-5097 (1991).
Dubé et al., *J. Biol. Chem.*, 263(33): 17516-17521 (1988).
Dumas et al., *Bioorg. Med. Chem. Lett.*, 1(8): 425-428 (1991).
Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Durieux et al., *Tetrahedron Lett.*, 42(12): 2297-2299 (2001).
Dwek et al., *J. Anat.*, 187(Pt. 2): 279-292 (1995).
Eavarone et al., *J. Biomed. Mater. Res.*, 51(1): 10-14 (2000).
Edge et al., *Anal. Biochem.*, 118(1): 131-137 (1981).
Elhalabi et al., *Curr. Med. Chem.*, 6(2): 93-116 (1999).
Espuelas et al., *Bioorg. Med. Chem. Lett.*, 13(15): 2557-2560 (2003).
Fairhall et al., Endocrinology, 131(4): 1963-1969 (1992).
Fan et al., *J. Biol. Chem.*, 272(43): 27058-27064 (1997).
Feldman et al., *Proc. Natl. Acad. Sci. USA*, 102(8): 3016-3021 (2005).
Felix et al., *J. Peptide Res.*, 63: 85-90 (2004).
Fibi et al., *Blood*, 85(5): 1229-1236 (1995).
Fischer et al., *Thromb. Res.*, 89(3): 147-150 (1998).
Flynn et al., *Curr. Opin. Oncol.*, 12(6): 574-581 (2000).
Francis et al., *Intl. J. Hematol.*, 68(1): 1-18 (1998).
Fritz et al., *Proc. Natl. Acad. Sci. USA*, 101(43): 15307-15312 (2004).
Fritz et al., *J. Biol. Chem.*, 281(13): 8613-8619 (2006).
Garnett et al., *Adv. Drug Deliv. Rev.*, 53(2): 171-216 (2002).
Gatot et al., *J. Biol. Chem.*, 273(21): 12870-12880 (1998).

(56) References Cited

OTHER PUBLICATIONS

Ge et al., *J. Biol. Chem.*, 272(34): 21357-21363 (1997).
Gervais et al., *Glycobiology*, 13(3): 179-189 (2003).
Gilbert et al., *Cytotechnology*, 22(1-3): 211-216 (1996).
Gillis et al., *Behring Inst. Mitt.*, 83: 1-7 (1988).
Ginns, PEG Glucocerebrosidase, Internet page from www.gaucher.org.uk/peg2.prg, Nov. 1994, printed Jun. 21, 2002.
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Gotschlich, *J. Exp. Med.*, 180(6): 2181-2190 (1994).
Grabenhorst et al., *Eur. J. Biochem.*, 215(1): 189-197 (1993).
Grabenhorst et al., *J. Biol. Chem.*, 274(51): 36107-36116 (1999).
Grodberg et al., *Eur. J. Biochem.*, 218(2): 597-601 (1993).
Gross et al., *Eur. J. Biochem,.* 177(3): 583-589 (1988).
Gross et al., *Biochemistry*, 28(18): 7386-7392 (1989).
Gross, *Eur. J. Biochem.*, 203(1-2): 269-275 (1992).
Guo et al., *Appl. Biochem. Biotechnol.*, 68(1-2): 1-20 (1997).
Hagen et al., *J. Biol. Chem.*, 274(10): 6797-6803 (1999).
Hagen et al., *J. Biol. Chem.*, 276(20): 17395-17404 (2001).
Hall, *Methods Mol. Biol.*, 166: 139-154 (2001).
Hällgren et al., *J. Carb. Chem.*, 14(4-5): 453-464 (1995).
Haneda et al., *Carbohydr. Res.*, 292: 61-70 (1996).
Hang et al., *J. Am. Chem. Soc.*, 123(6): 1242-1243 (2001).
Hansen et al., *Biochem J.*, 308: 801-813 (1995).
Haro et al., *Biochem. Biophys. Res. Comm.*, 228(2): 549-556 (1996).
Harris et al., *Nat. Rev. Drug Discov.*, 2(3): 214-221 (2003).
Harris et al., Abstracts of Papers of the American Chemical Society, V 201, APR, p. 64-POLY, pp. 154-155 (1991).
Harris, *J. Macromol. Science, Rev. Macromol. Chem. Phys.*, C25(3): 325-373 (1985).
Hassan et al., *J. Biol. Chem.*, 275(49): 38197-38205 (2000).
Hassan et al., *Carbohydrates in Chemistry and Biology*, Part II, 3: 273-292 (2000).
Hayes et al., *J. Biol. Chem.*, 268(22): 16170-16178 (1993).
Hellstrom et al., *Methods Mol. Biol.*, 166: 3-16 (2001).
Hermentin, et al., *Glycobiology*, 6(2): 217-230 (1996).
Herscovics et al., *FASEB J.*, 7(6): 540-550 (1993).
Hills et al., *Am. Biotechnol. Lab.*, 20(11): 30 (2002).
Hink et al., *Biotechnol. Prog.*, 7(1): 9-14 (1991).
Höglund, *Med. Oncol.*, 15(4): 229-233 (1998).
Hollister et al., *Glycobiology*, 11(1): 1-9 (2001).
Hounsell et al., *Glycoconj. J.*, 13(1): 19-26 (1996).
Hu et al., *Mol. Cell. Biol.*, 18(10): 6063-6074 (1998).
Ichikawa et al., *J. Am. Chem. Soc.*, 114(24): 9283-9298 (1992).
Ikonomou et al., *In Vitro Cell. Dev. Biol. Anim.*, 37(9): 549-559 (2001).
Inlow et al., *J. Tissue Cult. Methods*, 12(1): 13-16 (1989).
Inoue et al., *Biotechnol. Annu. Rev.*, 1: 297-313 (1995).
Ito et al., *Pure Appl. Chem.*, 65(4): 753-762 (1993).
Jackson et al., *Anal. Biochem.*, 165(1): 114-127 (1987).
Jarvis et al., *Curr. Opin. Biotechnol.*, 9(5): 528-533 (1998).
Jezek et al., *J. Peptide Sci.*, 5: 46-55 (1999).
Joppich et al., *Makromol. Chem.*, 180: 1381-1384 (1979).
Joshi et al., *J. Biol. Chem.*, 265(24): 14518-14525 (1990).
Jung et al., *Biochim. Biophys. Acta*, 761(2): 152-162 (1983).
Kajihara et al., *Carbohydrate Research*, 315: 137-141 (1999).
Kalsner et al., *Glycoconj. J.*, 12(3): 360-370 (1995).
Kaneko et al., *Cytogenet. Cell Genet.*, 86(3-4): 329-330 (1999).
Kaneko et al., *FEBS Lett.*, 452(3): 237-242 (1999).
Kasina et al., *Bioconjug. Chem.*, 9(1): 108-117 (1998).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keene et al., *J. Biol. Chem.*, 264(9): 4769-4775 (1989).
Kennedy, "Hydrophobic-Interaction Chromatography," in *Current Protocols in Protein Science*, pp. 8.4.1-8.4.21, Wiley (1995).
Keppler et al., *Glycobiology*, 11(2): 11R-18R (2001).
Kimura et al., *Proc. Natl. Acad. Sci. USA*, 96(8): 4530-4535 (1999).
Kisselev, *Structure*, 10(1): 8-9 (2002).
Kitamura et al., *Biochem. Biophys. Res. Commun.*, 171(3): 1387-1394 (1990).
Kitamura et al., *Cancer Res.*, 51(16): 4310-4315 (1991).
Kobayashi et al., *Eur. J. Nucl. Med.*, 27(9):1334-1339 (2000).
Kodama et al., *Tetrahedron Lett.*, 34(40): 6419-6422 (1993).
Koeller et al., *Nat. Biotechnol.*, 18(8): 835-841 (2000).
Koeller et al., *Nature*, 409(6817): 232-240 (2001).
Koide et al., *Biochem. Biophys. Res. Commun.*, 111(2): 659-667 (1983).
Kornfeld et al., *Ann. Rev. Biochem.*, 54: 631-664 (1985).
Kreitman, *Curr Pharm Biotechnol.*, 2(4): 313-325 (2001).
Krystal et al., *Blood*, 67(1): 71-99 (1986).
Kuhn et al., *J. Biol. Chem.*, 270(49): 29493-29497 (1995).
Kukowska-Latallo et al., *Genes Dev.*, 4(8): 1288-1303 (1990).
Kukuruzinska et al., *Proc. Natl. Acad. Sci. USA*, 84(8): 2145-2149 (1987).
Lai et al., *J. Biol. Chem.*, 261(7): 3116-3121 (1986).
Langer, *Science*, 249(4976): 1527-1533 (1990).
Lau et al., *J. Biotechnol.*, 75(2-3): 105-115 (1999).
Lee et al., *Biochemistry*, 28(4): 1856-1861 (1989).
Lee-Huang et al., *Proc. Natl. Acad. Sci. USA*, 81(9): 2708-2712 (1984).
Legault et al., *J. Biol. Chem.*, 270(36): 20987-20996 (1995).
Leist et al., *Science*, 305: 239-242 (2004).
Leiter et al., *J. Biol. Chem.*, 274(31): 21830-21839 (1999).
Leung, *J Immunol.* 154(11): 5919-5926 (1995).
Lewis et al., *Endocr. J.*, 47(Suppl.): S1-S8 (2000).
Li et al., *Trends Pharmacol. Sci.*, 23(5): 206-209 (2002).
Li et al., *Med. Res. Rev.*, 22(3): 225-250 (2002).
Licari et al., *Biotechnol. Bioeng.*, 39(4): 432-441 (1992).
Licari et al., *Biotechnol. Bioeng.*, 39(9): 932-944 (1992).
Lin et al., *Proc. Natl. Acad. Sci. USA*, 82: 7580-7584 (1985).
Liu et al., *Chem. Eur. J.*, 2(11): 1359-1362 (1996).
Long et al., *Exp. Hematol.*, 34(6): 697-704 (2006).
Lönnberg, *Curr. Org. Synth.*, 6(4): 400-425 (2009).
Lord et al., *Clin. Cancer Res.*, 7(7): 2085-2090 (2001).
Lougheed et al., *J. Biol. Chem.*, 274(53): 37717-37722 (1999).
Luckow et al., *Curr. Opin. Biotechnol.*, 4(5): 564-572 (1993).
Lund et al., *FASEB J.*, 9(1): 115-119 (1995).
Lund et al., *J. Immunol.*, 157(11): 4963-4969 (1996).
Mahal et al., *Science*, 276(5315): 1125-1128 (1997).
Malissard et al., *Biochem. Biophys. Res. Commun.*, 267(1): 169-173 (2000).
Maranga et al., *Biotechnol. Bioeng.*, 84(2): 245-253 (2003).
Maras et al., *J Biotechnol.*, 77(2-3): 255-263 (2000).
Meynial-Salles et al., *J. Biotechnol.*, 46(1): 1-14 (1996).
Miller, *Curr. Opin. Genet. Dev.*, 3(1): 97-101 (1993).
Min et al., *Endocr. J.*, 43(5): 585-593 (1996).
Mistry et al., *Lancet*, 348(9041): 1555-1559 (1996).
Mollicone et al., *Eur. J. Biochem.*, 191(1): 169-176 (1990).
Monaco et al., *Gene*, 180: 145-150 (1996).
Morimoto et al., *Glycoconj. J.*, 13(6): 1013-1020 (1996).
Muller et al., *J. Biol. Chem.*, 272(40): 24780-24793 (1997).
Muller et al., *J. Biol. Chem.*, 274(26): 18165-18172 (1999).
Nagata et al., *EMBO J.*, 5(3): 575-581 (1986).
Natsuka et al., *J. Biol. Chem.*, 269(24): 16789-16794 (1994).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Ngo et al., "The Protein Folding Problem and Tertiary Structure Prediction, Chapter 14: Computational Complexity Protein Structure Prediction, and the Levinthal Paradox," pp. 433-440 and 492-495 (1994).
Nilsson et al., *Methods Enzymol.*, 104: 56-69 (1984).
Nunez et al., *Can. J. Chem.*, 59(14): 2086-2095 (1981).
O'Connell et al., *J. Biol. Chem.*, 267(35): 25010-25018 (1992).
Oetke et al., *J. Biol. Chem.*, 277(8): 6688-6695 (2002).
Oh-Eda et al., *J. Biol. Chem.*, 265: 11432-11435 (1990).
Olson et al., *J. Biol. Chem.*, 274(42): 29889-29896 (1999).

(56) References Cited

OTHER PUBLICATIONS

Orlean, "Vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Orskov et al., *J. Biol. Chem.*, 264(22): 12826-12829 (1989).
O'Shannessy et al., *J. Appl. Biochem.*, 7: 347-355 (1985).
Palacpac et al., *Proc. Natl. Acad. Sci. USA*, 96(8): 4692-4697 (1999).
Palcic et al., *Carbohydr. Res.*, 190(1): 1-11 (1989).
Park et al., *J. Biol. Chem.*, 261(1): 205-210 (1986).
Paulson et al., *J. Biol. Chem.*, 252(23): 8624-8628 (1977).
Plummer et al., *J. Biol. Chem.*, 270(22): 13192-13196 (1995).
PNGase-F Amidase Sequence from F. Meningosepticum (RN 128688-70-0) (2007).
PNGase-F Amidase Sequence from F. Meningosepticum (RN 128688-71-1) (2007).
Prati et al., *Biotech and Bioeng.*, 79(5): 580-585 (2002).
Prieels et al., *J. Biol. Chem.*, 256(20): 10456-10463 (1981).
Pyatak et al., *Res. Commun. Chem. Pathol. Pharmacol.*, 29(1): 113-127 (1980).
Quelle et al., *Blood*, 74(2): 652-657 (1989).
Rabouille et al., *J Cell Sci.*, 112(Pt. 19): 3319-3330 (1999).
Rasko et al., *J. Biol. Chem.*, 275(7): 4988-4994 (2000).
R & D Systems, Fibroblast Growth Factors (FGFs), Internet page from www.rndsystems.com/mini_review_detail_objectname_MR01_FGFs.aspx, 2001, printed Mar. 10, 2011.
Rathnam et al., *Biochim. Biophys. Acta*, 624(2): 436-442 (1980).
Reff et al., *Cancer Control*, 9(2): 152-166 (2002).
Rosenthal et al., *Methods Enzymol.*, 235: 253-285 (1994).
Rotondaro et al., *Mol. Biotech.*, 11: 117-128 (1999).
Rudikoff et al., *Proc. Natl. Acad. Sci. USA*, 79(6):1979-1983 (1982).
Sadler et al., *Methods Enzymol.*, 83: 458-514 (1982).
Sandberg et al., *Semin. Hematol.*, 38(2 Suppl. 4): 4-12 (2001).
Saneyoshi et al., *Biol. Reprod.*, 65(6): 1686-1690 (2001).
Sasaki et al., *J. Biol. Chem.*, 262(25): 12059-12076 (1987).
Sasaki et al., *J.Biol. Chem.*, 269(20): 14730-14737 (1994).
Saxon et al., *Science*, 287(5460): 2007-2010 (2000).
Saxon et al., *J. Am. Chem. Soc.*, 124(50): 14893-14902 (2002).
Schlaeger, *Cytotechnology*, 20(1-3): 57-70 (1996).
Schwarz et al., *Nucl. Med. Biol.*, 26(4):383-388 (1999).
Schwientek et al., *Gene*, 145(2): 299-303 (1994).
Schwientek et al., *J. Biol. Chem.*, 277(25): 22623-22638 (2002).
Scouten, *Methods Enzymol.*, 135: 30-65 (1987).
Seely et al., *J. Chromatog.*, 908: 235-241 (2001).
Seffernick et al., *J. Bacteriol.*, 183(8): 2405-2410 (2001).
Seitz, *Chembiochem.*, 1(4): 214-246 (2000).
Shah et al., *J. Pharm. Sci.*, 85(12): 1306-1311 (1996).
Shapiro et al., *Blood*, 105(2): 518-525 (2005).
Shen et al., *Biochem. Biophys. Res. Commun.*, 102(3): 1048-1054 (1981).
Shinkai et al., *Prot. Exp. Purif.*, 10: 379-385 (1997).
Sinclair et al., *J. Pharm. Sci.*, 94: 1626-1635 (2005).
Singh et al., *Chem. Commun.*, 1996(8): 993-994 (1996).
Sinha et al., *Infect. Immun.*, 29(3): 914-925 (1980).
Skolnick et al., *Trends Biotechnol.*, 18(1): 34-39 (2000).
Smith et al., *Nat. Biotechnol.*, 15(12): 1222-1223 (1997).
Snider et al., *J. Chromatogr.*, A 599(1-2): 141-155 (1992).
Sojar et al., *Arch. Biochem. Biophys.*, 259(1): 52-57 (1987).
Song et al., *J. Pharmacol. Exp. Ther.*, 301(2): 605-610 (2002).
Srinivasachar et al., *Biochemistry*, 28(6): 2501-2509 (1989).
Srivastava et al., *J. Biol. Chem.*, 267(31): 22356-22361 (1992).
Staudacher, *Trends Glycosci. Glycotechnol.*, 8(44): 391-408 (1996).
Stemmer, *Nature*, 370(6488): 389-391 (1994).
Stemmer, *Proc. Natl. Acad. Sci. USA*, 91(22): 10747-10751 (1994).
Stephens et al., *Eur. J. Biochem.*, 133(1): 155-162 (1983).
Stephens et al., *Eur. J. Biochem.*, 133(3): 481-489 (1983).
Stephens et al., *Eur. J. Biochem.*, 135(3): 519-527 (1983).
Strausberg et al., *Proc Natl Acad Sci USA*, 99(26): 16899-16903 (2002).
Takane et al., *J Pharmacol Exp Ther.*, 294(2): 746-752 (2000).
Takeda et al., *Trends Biochem. Sci.*, 20(9): 367-371 (1995).
Takeuchi et al., *J. Biol. Chem.*, 265(21): 12127-12130 (1990).
Taniguchi et al., *Proteomics*, 1(2): 239-247 (2001).
Tanner et al., *Biochim. Biophys. Acta*, 906(1): 81-99. (1987).
Taylor et al., Protein Immobilization Fundamentals and Applications, Manual (1991).
Ten Hagen et al., *J. Biol. Chem.*, 274(39): 27867-27874 (1999).
Tenno et al., *J. Biol. Chem.*, 277(49): 47088-47096 (2002).
Thotakura et al., *Meth. Enzym.*, 138: 350-9 (1987).
Tom et al., *AAPS Journal*, 9(2): E227-E234 (2007).
Trottein et al., *Mol. Biochem. Parasitol.*, 107(2): 279-287 (2000).
Tsuboi et al., *Arch. Biochem. Biophys.*, 374(1): 100-106 (2000).
Tsunoda et al., *J. Pharmacol. Exp. Ther.*, 209(1): 368-372 (1999).
Tuddenham, *Nature*, 419(6902): 23-24 (2002).
Udenfriend et al., *Annu. Rev. Biochem.*, 64: 563-591 (1995).
Ulloa-Aguirre et al., *Endocrine*, 11(3): 205-215 (1999).
Uludag et al., *Biotechnol. Prog.*, 18(3): 604-611 (2002).
Uptima, Detergents: Solubilization of Biomolecules, Internet page from vvww.interchim.com/interchim/bio/produits_uptima/product_line/p1p_detergents.htm, 2001, printed Nov. 14, 2011.
Urdal et al, *J. Chromatogr.*, 296: 171-179 (1984).
Van Berkel et al., *Biochem. J.*, 319(Pt. 1): 117-122 (1996).
Van Reis et al., *Biotechnol. Bioeng.*, 38(4): 413-422 (1991).
Van Tetering et al., *FEBS Lett.*, 461(3): 311-314 (1999).
Veronese et al., *Appl. Biochem. Biotechnol.*, 11(2): 141-152 (1985).
Veronese, *Biomaterials*, 22(5): 405-417 (2001).
Vitetta et al., *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., *Crit. Rev. Ther. Drug Carrier Syst.*, 18(1): 1-76 (2001).
Wang et al., *Glycobiology*, 6(8): 837-842 (1996).
Wang et al., *Tetrahedron Lett.*, 37(12): 1975-1978 (1996).
Wang et al., *Protein Eng.*, 11(12): 1277-1283 (1998).
Wang et al., *Microbiol.*, 145(Pt. 11): 3245-3253 (1999).
Wellhoner et al., *J. Biol. Chem.*, 266(7): 4309-4314 (1991).
Wells, *Biochemistry*, 29(37): 8509-8517 (1990).
Weston et al., *J. Biol. Chem.*, 267(6): 4152-4160 (1992).
Weston et al., *J. Biol. Chem.*, 267(34): 24575-24584 (1992).
White et al., *J. Biol. Chem.*, 270(41): 24156-24165 (1995).
Wishart et al., *J. Biol. Chem.*, 270(45): 26782-26785 (1995).
Witkowski et al., *Biochemistry*, 38(36): 11643-11650 (1999).
Witte et al., *J. Am. Chem. Soc.*, 119(9): 2114-2118 (1997).
Witte et al., *Cancer and Metastasis Rev.*, 17: 155-161 (1998).
Woghiren et al., *Bioconjug. Chem.*, 4(5): 314-318 (1993).
Wong et al., *J. Org. Chem.*, 47(27): 5416-5418 (1982).
Wong et al., *Enzyme Microb Technol.*, 14(11): 866-874 (1992).
Wong et al., *Biotechnol. Bioeng.*, 49(6): 659-666 (1996).
Woods et al., *Eur. J. Cell Biol.*, 50(1): 132-143 (1989).
Wright et al., *J. Immunol.*, 160(7): 3393-3402 (1998).
Wu et al., *J. Drug Target.*, 10(3): 239-245 (2002).
Xing et al., *Biochem. J.*, 336(Pt. 3): 667-673 (1998).
Yamada et al., *Biochemistry*, 20(17): 4836-4842 (1981).
Yamamoto et al., *Carbohydr. Res.*, 305(3-4): 415-422 (1998).
Yarema et al., *J. Biol. Chem.*, 273(47): 31168-31179 (1998).
Yin et al., *Pharm. Res.*, 21(12): 2377-2383 (2004).
Yoshida et al., *Glycobiology*, 9(1): 53-58 (1999).
Yoshitake et al., *Biochemistry*, 24(14): 3736-3750 (1985).
Younes et al., *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, *Bioconjug. Chem.*, 6(2): 150-165 (1995).
Zarling et al., *J. Immunol.*, 124(2): 913-920 (1980).
Zhang et al., *Biochim. Biophys. Acta*, 1425: 441-452 (1998).
Zheng et al., *Biotechnol. Bioeng.*, 65(5): 600-604 (1999).
Zhou et al., 1994, *Mol. Microbiol.*, 14(4): 609-618 (1994).
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.

(56) References Cited

OTHER PUBLICATIONS

Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Office Action dated Oct. 23, 2012 in U.S. Appl. No. 12/811,963.
Office Action dated Nov. 9, 2012 in U.S. Appl. No. 12/663,056.
Office Action dated Nov. 26, 2012 in U.S. Appl. No. 13/215,439.
Office Action dated Dec. 21, 2012 in U.S. Appl. No. 13/246,512.
Perrin et al., "Common Physical Techniques Used in Purification," in *Purification of Laboratory Chemicals*, pp. 30-31, Pergamon (1980).
Song et al., *Mar. Drugs*, 1: 34-45 (2003).
Detty et al., "Enzyme-Catalyzed Synthesis of N-Acetyllactosamine With In Situ Regeneration of Uridine 5'-Diphosphate Glucose and Uridine 5'-Diphosphate Galactose," *J. Org. Chem.*, 47(27): 5415-5418 (1982).
Drucker et al., "Glucagon Gene Expression in Vertebrate Brain," *J. Biol. Chem.*, 263(27): 13475-13478 (1988).
Moscatelli et al., "Enzymatic Properties of a β-Glucanase from *Bacillus subtilis*," *J. Biol. Chem.*, 236(11): 2858-2862 (1961).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Koeller et al., "Complex Carbohydrate Synthesis Tools for Glycobiologists: Enzyme-Based Approach and Programmable One-Pot Strategies," *Glycobiology*, 10(11): 1157-1169 (2000).
Tsuji, "Molecular Cloning and Functional Analysis of Sialyltransferases," *J. Biochemistry*, 120: 1-13 (1996).
Office Action dated Jan. 17, 2013 in U.S. Appl. No. 13/541,185.
Office Action dated Mar. 6, 2013 in U.S. Appl. No. 13/157,575.
Office Action dated Mar. 13, 2013 in U.S. Appl. No. 12/811,963.
Office Action dated Mar. 14, 2013 in U.S. Appl. No. 12/784,323.
Office Action dated Mar. 21, 2013 in U.S. Appl. No. 13/541,185.
Office Action dated May 9, 2013 in U.S. Appl. No. 12/594,326.
Office Action dated May 21, 2013 in U.S. Appl. No. 12/811,963.
Office Action dated Jun. 6, 2013 in U.S. Appl. No. 11/701,949.
Office Action dated Jul. 11, 2013 in U.S. Appl. No. 11/652,467.
Office Action dated Jul. 17, 2013 in U.S. Appl. No. 13/215,439.
Office Action dated Jul. 30, 2013 in U.S. Appl. No. 13/246,512.
Office Action dated Aug. 12, 2013 in U.S. Appl. No. 13/541,185.
Office Action dated Sep. 6, 2013 in U.S. Appl. No. 12/784,323.
Office Action dated Sep. 16, 2013 in U.S. Appl. No. 11/781,885.
Office Action dated Sep. 17, 2013 in U.S. Appl. No. 11/781,888.
Office Action dated Sep. 25, 2013 in U.S. Appl. No. 12/663,748.
Office Action dated Oct. 10, 2013 in U.S. Appl. No. 10/581,538.
Office Action dated Oct. 16, 2013 in U.S. Appl. No. 11/597,258.
Office Action dated Nov. 7, 2013 in U.S. Appl. No. 12/811,963.
Office Action dated Dec. 5, 2013 in U.S. Appl. No. 10/565,331.
Office Action dated Dec. 26, 2013 in U.S. Appl. No. 13/157,575.
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).
Brinkman-Van Der Linden et al., *J. Biol. Chem.*, 271(24): 14492-14495 (1996).
Broquet et al., *Eur. J. Biochem.* 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al, *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett 1999*, (9): 1495-1507 (1999).
De Rosa et al., *Phytochemistry*, 42(4): 1031-1034 (1996).
Deangelis et al., *Biochemistry*, 33(31): 9033-9039 (1994).
Deluca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Dudas et al., *Infect. Immun.*, 56(2): 499-504 (1988).
Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia, pp. 568-575 (1988).
EMBL Accession No. M80599 and M86935, pp. 1-6 (Jan. 23, 1992).
EMBL Accession No. S56361, pp. 1-4 (May 4, 1993).
EMBL Accession No. U00039, pp. 1-137 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare, Instructions 28-9064-05 AA, pp. 1-32 (2006).
GE Healthcare, Instructions 28-9064-05 AC, pp. 1-40 (2006).
GenBank Accession No. AAA98726, "Factor IX," pp. 1-3 (Apr. 14, 2009).
GenBank Accession No. CAA01607, "Factor IX of *Homo sapiens*," pp. 1-2 (Apr. 14, 2009).
GenBank Accession No. D49915, pp. 1-3 (Sep. 1, 1995).
GenBank Accession No. U02304, p. 1 (Mar. 8, 1994).
GenBank Accession No. U18918, p. 1 (Oct. 1, 1995).
Gibson et al., *J. Bacteriol.*, 175(9): 2702-2712 (1993).
Gilbert, "Methods in Enzymology" Packer (ed.), 2(251): 8-28, Biothiols Part A, Elsevier (1995).
Gillespie et al., *FASEB Journal*, 4(7): A2068 [Abstract No. 2173] (1990).
Gillespie et al., *J. Biol. Chem.*, 267(29): 21004-21010 (1992).
Goodson et al., *Biotechnology (N.Y.)*, 8(4): 343-346 (1990).
Greenwell et al., *Blood Group A Synthesising Activity of the Blood Group B Gene Specified .alpha-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).

(56) References Cited

OTHER PUBLICATIONS

Helling et al., *Cancer Res.*, 54(1): 197-203 (1994).
Higa et al., *J. Biol. Chem.*, 260(15): 8838-8849 (1985).
Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990).
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).
Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta.*, 1437(2): 101-118 (1999).
Mackenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).
Manfioletti et al., "The Protein Encoded by a Growth Arrest-Specific Gene (*gas6*) Is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Muramatsu et al., *Comprehensive Research on Clinical Organ Xenotransplantation by Genetic Regulation*, p. 10-12. (1997).
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).

Raju et al., "Glycoengineering of Therapeutic Glycoproteins: In Vitro Galactosylation and Sialylation of Glycoproteins with Terminal *N*-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbiol.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).
Sandlin et al., *J. Bacteriol.*, 176(10): 2930-2937 (1994).
Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).
Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
Swiss-Prot Accession No. P19817, p. 1 (Feb. 1, 1991).
Swiss-Prot Accession No. P25740, pp. 1-6 (May 1, 1992).
Swiss-Prot Accession No. P27129, pp. 1-5 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl Le$^x$ but Not 6-Sulfo Sialyl Le$^x$ Expressed on the Cell Surface Supports L-selectin-mediated Adhesion," *J. Biol. Chem.*, 271(44): 27213-27216 (1996).
Tsujihara et al., *Chem. Pharm. Bull.*, (Tokyo) 29(11): 3262-3273 (1981).
Van Den Eijnden et al., *J. Biol. Chem.*, 256(7): 3159-3162 (1981).
Van Den Eijnden et al., *J. Biol. Chem.*, 258(6): 3435-3437 (1983).
Van Putten et al., *EMBO J.*, 12(11): 4043-4051 (1993).
Van Roey et al., *Biochemistry*, 33(47): 13989-13996 (1994).
Vann et al., *J Biol Chem.*, 262(36): 17556-17562 (1987).
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Webster et al., *J. Biol. Chem.*, 258(17): 10637-10641 (1983).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia, Image:Ceramide.svg, http://en.wikipedia.org/wiki/Ceramide, pp. 1-2 (2007).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).

(56) References Cited

OTHER PUBLICATIONS

Yamasaki et al., *J. Bacteriol.*, 175(14): 4565-4568 (1993).
Yoshikawa et al., *Phytochemistry*, 34(5): 1431-1433 (1993).
Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).
Cheng et al., "Poly(ethylene glycol) . modification of β-glucuronidase-antibody conjugates for solid-tumor therapy by targeted activation of glucuronide prodrugs," *Cancer Immunol. Immunother.*, 44: 305-315 (1997).
Duncan, "The dawning era of polymer therapeutics," *Nature Reviews Drug Discovery*, 2(5): 347-360 (2003).
Eisenhaber et al., "Prediction of Posttranslational Modification of Proteins from Their Amino Acid Sequence," *Methods in Molecular Biology*, 609: 365-384 (2010).
Fay, "Activation of factor VIII and mechanisms of cofactor action," *Blood Reviews*, 18: 1-15 (2004).
Fernandes et al., "The effect of polysialylation on the immunogenicity and antigenicity of asparaginase: implication in its pharmacokinetics," *Intl. J. of Pharmaceutics*, 217(1): 215-224 (2001).
Kelleher et al., "Oligosaccharyltransferase Isoforms that Contain Different Catalytic STT3 Subunits Have Distinct Enzymatic Properties," *Molecular Cell*, 12: 101-111 (2003).
Kirikoshi et al., "Molecular Cloning and Characterization of Human FGF-20 on Chromosome 8p21.3-p22," *Biochem. and Biophys. Research Comm.*, 274: 337-343 (2000).
Kumar et al., "'Green'-enzymatic synthesis of pegylated phenolic macromer and polymer," *Chem. Commun.*, 7(7): 862-863 (2004).
Lodish et al., "Protein Glycosylation in the ER and Golgi Complex," *Molecular Cell Biology*, Section 17.7, 4th Ed. New York, W. H. Freeman (2000).
Markovsky et al., "Administration, distribution, metabolism and elimination of polymer therapeutics," *J. Controlled Release*, 161: 446-460 (2012).
Matsumura et al., "A New Concept for Macromolecular Therapeutics in Cancer Chemotherapy: Mechanism of Tumoritropic Accumulation of Proteins and the Antitumor Agent Smancs," *Cancer Research*, 46: 6387-6392 (1986).
Mehvar, "Modulation of the Pharmacokinetics and Pharmacodynamics of Proteins by Polyethylene Glycol Conjugation," *J. Pharm. Pharmaceut. Sci.*, 3(1): 125-136 (2000).
Nishimura et al., "Identification of a novel FGF, FGF-21, preferentially expressed in the liver," *Biochemica et Biophysica Acta*, 1492: 203-206 (2000).
NOF Corporation Catalogue, *NOF Corporation*, Catalogue Ver. 8: 1-60 (2006).
Ohbayashi et al., "Structure and Expression of the mRNA Encoding a Novel Fibroblast Growth Factor, FGF-18," *J. Biol. Chem.*, 273(29): 18161-18164 (1998).
Ottenbrite, "Polymeric Drugs and Drug Delivery Systems," Dunn et al. (eds.), Chapter 1 "Biologically Active Polymers," pp. 3-10, ACS Symposium Series vol. 469, *American Chemical Society*, Washington D.C. (1991).
Satchi et al., "PDEPT: polymer-directed enzyme prodrug therapy I.HPMA copolymer-cathepsin B and PK1 as a model combination," *Brit. J. Cancer*, 85(7): 1070-1076 (2001).
Shu et al., "Peptide-Polymer Conjugates: From Fundamental Science to Application," *Annu. Rev. Phys. Chem.*, 64: 631-657 (2013).
Smallwood et al., "Fibroblast growth factor (FGF) homologous factors: new members of the FGF family implicated in nervous system development," *Proc. Natl. Acad. Sci. USA*, 93: 9850-9857 (1996).
SUNBRIGHT® GL2-400NP [100mg], NOF Corporation, http://www.nofamerica.com/store/index.php?dispatch=products.view&product_id=157, 1 page dated Aug. 5, 2015.
Vasey et al., "Phase I Clinical and Pharmacokinetic Study of PK1 [N-(2-Hydroxypropyl)methacrylamide Copolymer Doxorubicin]: First Member of a New Class of Chemotherapeutic Agents—Drug-Polymer Conjugates," *Clinical Cancer Research*, 5(1): 83-94 (1999).
Harris (ed.), "Poly(Ethylene Glycol) Chemistry: Biotechnical and Biomedical Applications", Plenum Press, New York (1992) (Title Pages only).
Harris et al. (eds.), "Poly(ethylene glycol): Chemistry and Biological Applications," ACS Symposium Series, vol. 680, American Chemical Society (1997) (Title Pages only).
Hermanson et al., *Immobilized Affinity Ligand Techniques*, Academic Press (1992) (Table of Contents).
Hermanson, *Bioconjugate Techniques*, Academic Press, San Diego (1996) (Table of Contents).
Arslan et al., *Transf. Apher. Sci.*, 37: 179-185 (2007).
Broxmeyer et al., *J. Exp. Med.*, 201(8): 1307-1318 (2005).
Cantin et al., *Am. J. Respir. Cell Mol. Biol.*, 27(6): 659-665 (2002).
Capoccia et al., *Blood*, 108(7): 2438-2445 (2006).
Cashen et al., *Bone Marrow Trans.*, 39: 577-588 (2007).
Flomenberg et al., *Blood*, 106(5): 1867-1874 (2005).
Hill et al., *Biol. Blood Marrow Trans.*, 12: 603-607 (2006).
Hübel et al., *Ann. Hematol.*, 82: 207-213 (2003).
Kroschinsky et al., *Trans. Apher. Sci.*, 38: 237-244 (2008).
Liles et al., *Transfusion*, 45: 295-300 (2005).
Almeida et al., "Biomedical applications of polymer-based pharmaceuticals," *Biomedical Engineering*, pp. 1-16 (2008).
Bückmann et al., "Functionalization of Poly(Ethylene Glycol) and Monomethoxy-Poly(Ethylene Glycol)," *Angewandte Makromolekulare Chem.*, 182(5): 1379-1384 (1981).
Busterbosch et al., "Quantitative Analysis of the targeting of mannose-terminal glucocerebrosidase," *European Journal of Biochemistry*, 237: 344-349 (1996).
Butenas et al., "Potency and mass of factor VIII in FVIII products," *Haemophilia*, 15: 63-72 (2009).
Collins et al., "Recombinant long-acting glycoPEGylated factor IX in hemophilia B: a multinational randomized phase 3 trial," *Blood*, 124(26): 3880-3886 (2014).
Cox et al., "Enhanced circulating half-life and hematopoietic properties of a human granulocyte colony-stimulating factor/immunoglobulin fusion protein," *Experimental Hematology*, 32: 441-449 (2004).
Declaration of Juergen Siekmann, Ph.D., U.S. Appl. No. 12/184,567, 5 pgs. (2009).
Declaration of Juergen Siekmann, Ph.D., WO 2008/025856, 2 pgs. (2013).
De Graff et al., "Inflammation-Induced Expression of Sialyl Lewis X-Containing Glycan Structures on Alpha1-Acid Glycoprotein (Orosomucoid) in Human Sera," *Journal of Experimental Medicine*, 177: 657-666 (1993).
Definition of Insect Cells, From http://www.biochem.northwestern.edu/holmgren/Glossary/Definitions/Def-I/insect_cells.html, p. 1, accessed Apr. 14, 2009.
Definition of Moiety, From http://dictionary.reference.com/browse/moiety, p. 1-3, accessed Aug. 26, 2010.
Definition of N-Acetylglucosaminetransferase, From http://www.online-medical-dictionary.org/N-Acetylglucosaminyltransferases.asp?q=N-Acetylglucosaminyltransferases, pp. 1-2, accessed Apr. 14, 2009.
Dunn, Richard L. and Raphael M. Ottenbrite eds., "Polymeric Drugs and Drug Delivery Systems," *American Chemical Society*, pp. 3-23 (Aug. 15, 1991).
Eavarone et al., "Targeted Drug Delivery to C6 Glioma by Transferrin-Coupled Liposiomes," *J. Biomed. Mater. Res.*, 51: 41196 (2000).
El-Maarri et al., "Functional Analysis of the Factor VIII B Domain," 34th Hemophilia Symposium, pp. 324-337 (2005).
Ethylene Glycol Chemistry: Biotechnical & Biomedical Applications, POLY, 1992.
Fischer et al., "Comparison of N-Glycan Pattern of Recombinant Human Coagulation Factors II and IX Expressed In Chinese Hamster Ovary (CHO) and African Green Monkey (VERO) Cells," *Journal of Thrombosis and Thrombolysis*, 3: 57-62 (1996).
Geoghegan et al., "Periodate Inactivation of Ovotransferrin and Human Serum Transferrin," *The Journal of Biological Chemistry*, 255(23): 11429-11434 (Dec. 10, 1980).

(56) References Cited

OTHER PUBLICATIONS

Ghose et al., "Cytotoxicity Tests and Cytotoxic Agents," *Methods in Enzymology*, Academic Press Inc., San Diego, CA, 93: 280-333 (1983).
Gross et al., "A Highly Sensitive Fluorometric Assay For Sialyltransferase Activity Using CMP-9-Fluoresceinyl-Neuac as Donor," *Analytical Biochemistry*, 186(1): 127-134 (1990).
Hallgren et al., "An Animated GDP-Fucose Analog Useful in the Fucosyltranferase Catalyzed Addition of Biological Probes Onto Oligosaccharide Chains," *J. Carbo Chem.*, 14(4-5): 453-464 (1995).
Harris et al., "Identification and Structural Analysis of the Tetrasaccharide NeuAc alpha(2forward arrow6)Gal beta(1forward arrow4)GlcNac beta(1forward arrow3)Fuc alpha1 forward arrow O-linked to Serine 61 of Human Factor IX," *Biochemistry*, 32: 6539-6547 (1993).
Hedner et al., "Clinical Experience with Human Plasma-Derived Favor VIIa in Patients with Hemophilia A and High Titer Inhibitors," *Haemostatis*, 19: 335-343 (1989).
Johansen et al., "Prolonged effect of GlycoPEGylated rFVIIa (40I-PEG-rFVIIa) in Rabbits Correlates to Activity in Plasma," *Thrombosis and Haemostasis*, 104: 157-164 (2010).
Joshi, "Recent Advances in Drug Delivery Systems: Polymeric Prodrugs," *Pharmaceutical Technology*, 118-130 (Jun. 1988).
Jung et al., "Chemical Strategies for the Synthesis of Protein-Polymer Conjugates," *Advanced Polymer Science*, 253: 37-70 (2013).
Lenting et al., "The Life Cycle of Coagulation Factor VIII in View of Its Structure and Function," *Blood*, 92(11): 3983-3996 (Dec. 1, 1998).
Lenting et al., "Factor VIII and von Willebrand factor—too sweet for their own good," *Haemophilia*, 16(Suppl. 5): 194-199 (2010).
Liu et al., "A Paradigm Case For the Merging of Glycal and Enzymatic Assembly Methods in Glycoconjugate Synthesis: A Highly Efficient Chemo-Enzymatic Synthesis of GM3," *Chemistry—A European Journal*, 2(11): 1359-1362 (1996).
Ludlam, "The Evidence Behind Inhibitor Treatment with Recombinant Factor VIIa," *Pathophysiology of Haemostasis and Thrombosis*, 32(Suppl. 1): 13-18 (2002).
Makino et al., "Structural Analysis of N-Linked Sugar Chains of Human Blood Clotting Factor IX," *Journal of Biolochemistry*, 128: 175-180 (2000).
Mazsaroff et al., "Quantitative Comparison of Global Carbohydrate Structures of Glycoproteins Using LC-MS and In-Source Fragmentation," *Anal. Chem.*, 69: 2517-2524 (1997).
Mizugushi et al., "Structural Elements of Factor VIIA Required for Active Site Formation," *Thrombosis and Haemostasis*, 1474(466): abstract (1999).
Negrier et al., "Enhanced Pharmacokinetic Properties of a glycoPEGylated recombinant factor IX: a first human dose trial in patients with hemophilia B," *Blood*, 118(10): 2695-2701 (2011).
Neose Technologies, Inc.'s 2002 Annual Report, "Neose Technologies, Inc.'s 2002 Annual Report".
Neose Technologies, Inc.'s 2003 Annual Report, "Neose Technologies, Inc.'s 2003 Annual Report".
Neose Technologies, Inc.'s press release, "Neose Technologies, Inc.'s Press Release" (Nov. 17, 2003).
Neose Technologies, Inc.'s press release, "Neose Technologies, Inc.'s Press Release" (Jun. 28, 2006).
Okamoto et al., "The optimal molecular design of polymeric drug carriers and its application for renal drug targeting," *Gene Therapy and Molecular Biology*, 8: 221-230 (2004).
Parti et al., "In vitro stability of recombinant human factor VIII (Recombinate™)," *Haemophilia*, 6: 513-522 (2000).
Roberts et al., "Chemistry for Peptide and Protein Pegylation," *Advanced Drug Delivery Reviews*, 54: 459-476 (2002).
Saenko et al., "Strategies towards a longer acting factor VIII," *Haemophilia*, 12 (Suppl. 3): 42-51 (2006).
Sandberg et al., "Structural and Functional Characterization of B-Domain Deleted Recombinant Factor VIII," *Seminars in Hematology*, 38(2-Suppl. 4): 4-12 (2001).
Schachter et al., "The Biosynthesis of Branched O-Linked Glycans," *Society For Experimental Biology*, pp. 1-26, Great Britain (1989).
Shearwater Polymers, Inc., Polyethylene Glycol and Derivatives: Functionalized Biocompatible Polymers for Research and Pharmaceuticals, pp. 1-50 (Catalog-Jan. 2000).
Sheridan, "The Most Common Chemical Replacements in Drug-Like Compounds," *J. Chem. Inf. Comput. Sci.*, 42: 108-108 (2002).
Tenno et al., "The Lectin Domain of UDP-GaINAc:Polypeptide N-AcetylGalactosaminyltransferase 1 is involved in O-Glycosylation of a Polypeptide with Multiple Acceptor Sites," *Biochemistry*, 29(37): 8509-8517 (2002).
Veronese et al., "Bioconjugation in Pharmaceutical Chemistry Bioconjugation in Pharmaceutical Chemistry," *IL Farmaco*, 54(8): 497-516 (1999).
Vocadlo et al., "Glycosidase-Catalysed Oligosaccharide Synthesis," *Carbohydrates in Chemistry and Biology*, 2: 1-122 (2000).
Zalipsky et al., "Hydrazide Derivatives of Poly(ethylene glycol) and Their Bioconjugates," *ACS Symposium Series*, 680(21): 318-341 (1997).
Zeng et al., "High-efficiency labeling of sialylated glycoproteins on living cells," *Nature Methods*, 6(3): 207-209 (Mar. 2009).

* cited by examiner

PROCESS FOR THE PRODUCTION OF PURIFIED CYTIDINEMONOPHOSPHATE-SIALIC ACID-POLYALKYLENE OXIDE (CMP-SA-PEG) AS MODIFIED NUCLEOTIDE SUGARS VIA ANION EXCHANGE CHROMATOGRAPHY

CROSS-REFERENCES TO RELATED APPLICATIONS

This application is the U.S. national phase of International Patent Application PCT/US2008/066749, filed Jun. 12, 2008, which claims priority under 35 U.S.C. §119(e) to U.S. Provisional Patent Application No. 60/943,527 filed Jun. 12, 2007, U.S. Provisional Patent Application No. 60/968,274 filed Aug. 27, 2007, and U.S. Provisional Patent Application No. 60/970,247 filed Sep. 5, 2007, each of which is incorporated herein by reference in their entirety for all purposes.

FIELD OF THE INVENTION

The invention relates to methods of making sugar-nucleotides, wherein the sugar moiety is modified with a polymeric modifying group.

BACKGROUND OF THE INVENTION

Nucleotide sugars produced via enzymatically catalyzed reactions (e.g., using glycosyltransferases) and/or other synthetic methods are often obtained in the form of complex mixtures that include not only the desired compound but also contaminants such as unreacted sugars, salts, pyruvate, phosphate, nucleosides, nucleotides, proteins and the like. The presence of these contaminants is undesirable for many downstream applications. Side products are typically removed using one or more chromatographic purification steps. A common chromatographic method is reverse-phase chromatography. However, reverse-phase chromatography is often not feasible for large-scale applications due to expensive separation media and limited supply of pre-packed columns. In addition, for reverse-phase chromatography, organic solvents are typically required for optimal separation and resolution. A need exists for cost- and time-efficient processes and purification methods useful for the production of nucleotide sugars and their isolation from complex reaction mixtures. The present invention addresses this and other needs.

SUMMARY OF THE INVENTION

The current invention provides methods (e.g., large-scale processes) for the production of nucleotide sugars, which are modified with a polymeric modifying group. Exemplary modifying groups include at least one polymeric moiety selected from poly(alkylene oxide) moieties, such as poly(ethylene glycol) (PEG) and polypropylene glycol) (PPG) moieties. In particular, the current invention provides processes for the production of modified cytidine-monophosphate-sialic acids (CMP-SA). Exemplary modified nucleotide sugars, which can be produced using the methods of the invention, include CMP-SA-PEG-10 kDa, CMP-SA-PEG-20 kDa and CMP-SA-glycerol-PEG-40 kDa (see FIG. 2 for exemplary CMP-SA-PEGs).

Modified nucleotide sugars are used, e.g., in glycoconjugation (e.g., GlycoPEGylation) processes. Various methods for the synthesis of modified nucleotide sugars (e.g., CMP-SA-PEGs) have been described. See e.g., WO2003/31464 filed Oct. 9, 2002, WO2004/99231, filed Apr. 9, 2004 and WO2007/056191, filed Nov. 3, 2006, the disclosures of which are incorporated herein by reference in their entirety for all purposes.

Modified nucleotide sugars can be prepared by reacting a nucleotide sugar derivative incorporating a reactive functional group (e.g., an amino group) with a reactive polymeric reagent, such as a PEG-p-nitrophenyl (pNP) carbonate. For example, CMP-SA-PEGs, such as CMP-SA-PEG-10 kDa, CMP-SA-PEG-20 kDa and CMP-SA-glycerol-PEG-40 kDa, can be prepared by reacting CMP-SA-Glycine (GSC) with a PEG reagent incorporating a p-nitrophenyl carbonate moiety. An exemplary synthetic route according to this embodiment is outlined in FIG. 2. Unexpectedly, the inventors have discovered that a pH range between about 8.0 and about 8.8 in an aqueous solvent system is critical during the coupling reaction between PEG-p-nitrophenyl (pNP) carbonates (e.g., mPEG-p-nitrophenyl) and a nucleotide sugar derivative (e.g., CMP-SA-glycine). The optimized pH range largely reduces the formation of side-products due to hydrolysis of the reaction partners, and thus significantly increases yields and purities for the final products.

The current invention describes processes, which incorporate less production steps and provide modified nucleotide sugars (e.g. CMP-SA-PEGs) with improved purities and overall yields when compared to known methods. A typical process incorporates (a) anion exchange chromatography (AEX), which is useful, e.g., to remove PEG-based impurities. Anion exchange chromatography is followed by (b) desalting of the partially purified product solution using membrane filtration (i.e., ultrafiltration), such as tangential flow filtration (TFF). A representative process of the invention is depicted in FIG. 1. In one example, the TFF step uses a membrane with a molecular weight cutoff (MWCO) significantly smaller than the molecular weight of the modified nucleotide sugar being purified. For example, for CMP-SA-PEG-10 kDa, CMP-SA-PEG-20 kDa and CMP-SA-glycerol-PEG-40 kDa a membrane with a molecular weight cutoff between about 10 kDa and about 1 kDa is used. The improved process does not require ultrafiltration (e.g., TFF) before anion exchange chromatography. Instead, the volume of the crude reaction mixture can be reduced by evaporating part of the solvent that is present in the reaction mixture (e.g., THF). In one example, evaporation is accomplished using rotary evaporation. The volume-reduced mixture can then be filtered to remove particles, for example, through a 0.22 μm filter, before the mixture is subjected to anion exchange chromatography. In one example, modified nucleotide sugars (e.g., CMP-SA-PEGs) produced by a method of the invention, are obtained with purities greater than about 90% (w/w) and isolated yields between about 60 and about 80%.

In various examples, the invention provides a method of making a composition that includes a modified nucleotide sugar covalently linked to a polymeric modifying group, wherein the polymeric modifying group includes at least one linear or branched poly(alkylene oxide) moiety. The method includes: (i) contacting a reaction mixture comprising the modified nucleotide sugar with an anion exchange medium; (ii) eluting the modified nucleotide sugar from the anion exchange medium thereby forming an eluate fraction containing the modified nucleotide sugar; and (iii) desalting the eluate fraction. The method does preferably not include ultrafiltration (e.g., TFF) prior to anion exchange chromatography.

In a particular example, the method of the invention includes: (i) contacting a nucleotide sugar derivative including a primary amino group with an activated poly(alkylene oxide) moiety incorporating a p-nitrophenyl carbonate moiety under conditions sufficient to form a covalent bond between the amino group of the nucleotide sugar derivative and the poly(alkylene oxide) moiety. The contacting occurs in the presence of an aqueous solvent having a pH between about 8.0 and about 8.8. A reaction mixture is formed, which includes the modified nucleotide sugar. The method further include (ii) contacting the reaction mixture with an anion exchange medium and (iii) eluting the modified nucleotide sugar from the anion exchange medium forming an eluate fraction that contains the modified nucleotide sugar. The method can further include: (iv) desalting the eluate fraction using membrane filtration; and (v) removing water from the eluate fraction. The method does preferably not include ultrafiltration prior to step (i).

The invention further provides a modified nucleotide sugar produced by a method of the invention.

BRIEF DESCRIPTION OF THE DRAWINGS

In FIG. 2, n is an integer selected from 1 to 2500.

In FIG. 3, n is an integer selected from 1 to 2500.

DETAILED DESCRIPTION OF THE INVENTION

I. Abbreviations

Figure 1:
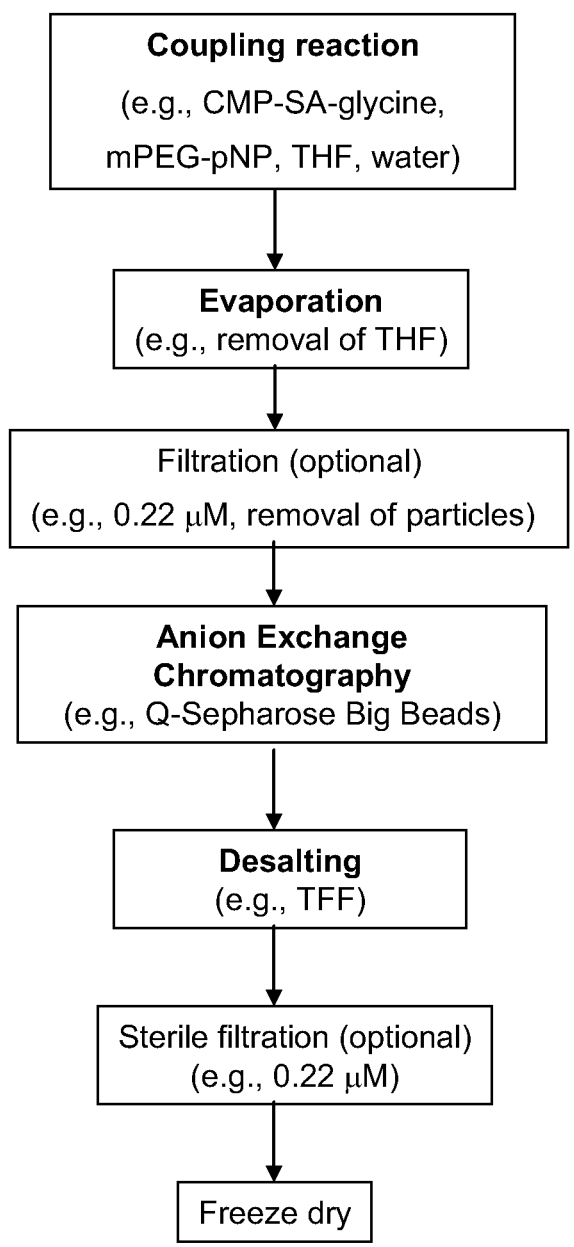
FIG. 1 is a diagram of an exemplary production process of the invention.

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; and NeuAc, sialyl (N-acetylneuraminyl); M6P, mannose-6-phosphate; BEVS, baculovirus expression vector system; CV, column volume; NTU, nominal turbidity units; vvm, volume/volume/min; ACN, acetonitrile; mcL, microliter; RO, reverse osmosis.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "nucleotide sugar" is used interchangeably with the term "sugar nucleotide" and refers to a nucleotide covalently linked to an additional sugar moiety, such as sialic acid. The nucleotide sugar is optionally cavalently modified with a polymeric modifying group, such as a linera or branched PEG moiety.

The "sugar moiety" of the nucleotide sugar of the invention is selected from both natural and unnatural furanoses and hexanoses. The unnatural saccharides optionally include an alkylated or acylated hydroxyl and/or amine moiety, e.g., ethers, esters and amide substituents on the ring. Other unnatural saccharides include an H, hydroxyl, ether, ester or amide substituent at a position on the ring at which such a substituent is not present in the natural saccharide. Alternatively, the carbohydrate is missing a substituent that would be found in the carbohydrate from which its name is derived, e.g., deoxy sugars. Still further exemplary unnatural sugars include both oxidized (e.g., -onic and -uronic acids) and reduced (sugar alcohols) carbohydrates. The sugar moiety can be a mono-, oligo- or polysaccharide.

Exemplary natural sugars of use in the present invention include glucose, galactose, fucose, mannose, xylanose, ribose, N-acetyl glucose (GlcNAc), sialic acid and N-acetyl galactose (GalNAc).

Similarly, the nucleoside can be selected from both natural and unnatural nucleosides. Exemplary natural nucleosides of use in the present invention include cytosine, thymine, guanine, adenine and uracil. A variety of unnatural nucleosides and methods of making them are known in the art.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galac-tononulopyranos-1-onic acid (often abbreviated as Neu5Ac, NeuAc, NAN or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, N.Y. (1992)). The synthesis and use of sialic acid compounds in a sialylation procedure is disclosed in international application WO 92/16640, published Oct. 1, 1992.

The term "anion-exchange chromatography" includes procedures involving packed columns as well as procedures involving anion-exchange membranes. The term "anion exchange chromatography" includes chromatography performed using any mixed-mode medium having anion-exchange capabiliteis.

The term "aqueous solvent" describes solvents incorporating at least about 10%, at least about 20%, at least about 30%, at least about 40%, at least about 50%, at leats about 60%, at least about 70% or at least about 80% water (v/v). The aqueous solvent can optionally include water-miscible organic solvents, such as alcohols (e.g., methanol, ethanol or butanol), THF and other aliphatic or cyclic ethers.

The term "polymeric modifying group" refers to any polymer attached to a nucleotide sugar of the invention. The polymeric modifying group can be water-soluble or essentially water-insoluble. Exemplary water-soluble polymers of use in the present invention include PEG, m-PEG and other functionalized PEG moieties, m-PPG, PPG, polysialic acid, polyglutamate, polyaspartate, polylysine, polyethyeleneimine and biodegradable polymers (e.g., polylactide, polyglyceride).

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly (ethylene imine) is an exemplary polyamine, and poly (acrylic) acid is a representative poly(carboxylic acid).

The polymer backbone of the water-soluble polymer can be poly(ethylene glycol) (i.e., PEG). However, it should be understood that other related polymers are also suitable for use in the practice of this invention and that the use of the term PEG or poly(ethylene glycol) is intended to be inclusive and not exclusive in this respect. The term "PEG" includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly (ethylene glycol) can be represented in general form as R(—PEG-OH)$_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as polypropylene glycol) ("PPG"), copolymers of ethylene glycol and propylene glycol and the like, poly(oxyethylated polyol), poly(olefinic alcohol), poly(vinylpyrrolidone), poly (hydroxypropylmethacrylamide), poly(α-hydroxy acid), poly(vinyl alcohol), polyphosphazene, polyoxazoline, poly (N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

A "feed solution" refers to any solution that contains a compound to be purified. For example, a reaction mixture can be used as a feed solution from which the desired reaction product is purified using the methods of the invention.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl" by itself or as part of another substituent, means, unless otherwise stated, a straight or branched chain, or cyclic (i.e., cycloalkyl) hydrocarbon radical, or combination thereof, which may be fully saturated, mono- or polyunsaturated and can include di- (e.g., alkylene) and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical unless otherwise indicated. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$, or —S(O)$_2$NR'—. The substituents R, R', R" and R"' are preferably independently selected from hydrogen or substituted or unsubstituted (C$_1$-C$_6$)alkyl.

As used herein, the term "heteroatom" includes oxygen (O), nitrogen (N), sulfur (S), silicon (Si) and boron (B).

The symbol "R" is a general abbreviation that represents a substituent group. Exemplary substituent groups include substituted or unsubstituted alkyl, substituted or unsubstituted heteroalkyl, substituted or unsubstituted aryl, substituted or unsubstituted heteroaryl, and substituted or unsubstituted heterocycloalkyl groups.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

As used herein, the term "modified sugar" refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "glycoconjugation" as used herein, refers to the enzymatically mediated conjugation of a modified sugar species to an amino acid or glycosyl residue of a polypeptide, e.g., an erythropoietin peptide prepared by the method of the present invention. A subgenus of "glycoconjugation" is "glyco-PEGylation," in which the modifying group of the modified sugar is poly(ethylene glycol), an alkyl derivative (e.g., m-PEG) or reactive derivative (e.g., H$_2$N—PEG, HOOC—PEG) thereof.

The terms "large-scale" and "industrial-scale" are used interchangeably and refer to a reaction cycle or process that produces at least about 250 mg, at least about 500 mg, at least about 1 gram, at least about 2 gram, at least about 5 g, at least about 10 g, at least about 20 g, at least about 30 g, at least about 50 or at least about 100 g of nucleotide sugar at the completion of a single cycle. In one embodiment, the invention provides large-scale processes, which are suitable to prepare nucleotide sugars to a high degree of purity on a kilogram scale (e.g., at least about 1 kg, at least about 1.5 kg, at least about 2 kg, or at least about 3 kg of purified sugar nucleotide per synthesis/purification run).

The term "isolated" or "purified" when referring to a nucleotide sugar or modified nucleotide sugar of the invention, means that such material is essentially free from components, which are used to produce the material. "Isolated", "pure" or "purified" are used interchangeably. Purity can be determined by any art-recognized method of analysis (e.g., band intensity on a silver stained gel, polyacrylamide gel electrophoresis, NMR, HPLC, ELISA, or a similar means). In one example, purity is determined as the ratio between the amount of desired nucleotide sugar and the amount of total other components present in a sample (w/w). For example the concentration of the nucleotide sugar in the sample may be determined using analytical chromatography (e.g., HPLC, RP—HPLC) in combination with a nucleotide sugar standard.

Typically, nucleotide sugars isolated using a method of the invention, have a level of purity expressed as a range. The lower end of the range of purity for the sugar nucleotide is about 30%, about 40%, about 50%, about 60%, about 70%, about 75% or about 80% and the upper end of the range of purity is about 70%, about 75% about 80%, about 85%, about 90%, about 95% or more than about 95%.

When the nucleotide sugar is more than about 90% pure, its purity is also preferably expressed as a range. The lower end of the range of purity is about 90%, about 92%, about 94%, about 96% or about 98%. The upper end of the range of purity is about 92%, about 94%, about 96%, about 98% or about 100% purity (w/w).

"nucleotide sugar recovery", "yield" or "reaction yield" is typically expressed as the range between the amount of recovered nucleotide sugar after a particular process step (or series of steps) and the amount of nucleotide sugar that entered the process step. For example, the recovery of nucleotide sugar for a method of the invention is about 20%, about 30%, about 40%, about 50%, about 60%, about 70%, about 80% or about 90%. In another example, the nucleotide sugar recovery for a method of the invention is about 92%, about 94%, about 96%, about 98% or more than about 98%.

The term "loading buffer" refers to the buffer, in which the peptide being purified is applied to a purification device, e.g. a chromatography column or a filter cartridge. Typically, the loading buffer is selected so that separation of the peptide of interest from unwanted impurities can be accomplished. For instance, when purifying the peptide on a hydroxyapatite (HA) or fluoroapatite column the pH of the loading buffer and the salt concentration in the loading buffer may be selected so that the peptide is initially retained on the column while certain impurities are found in the flow through.

The term "elution buffer", also called "limit buffer", refers to the buffer, which is typically used to remove (elute) the peptide from the purification device (e.g. a chromatographic column or filter cartridge) to which it was applied earlier. Typically, the loading buffer is selected so that separation of the peptide of interest from unwanted impurities can be accomplished. Often the concentration of a particular salt (e.g. NaCl) in the elution buffer is varied during the elution procedure (gradient). The gradient may be continuous or stepwise.

The term "room temperature" or "ambient temperature" refers to a temperature of at least about 10° C., at least about 15° C., at least about 20° C. or at least about 25° C. Typically, room temperature is between about 20° C. and about 25° C.

III. Methods

The current invention provides methods (e.g., large-scale processes) for the production of nucleotide sugars. In one embodiment, the nucleotide sugar is modified with a polymeric modifying group (modified nucleotide sugar). Exemplary polymeric modifying groups are disclosed herein. In one example, the polymeric modifying group includes at least one polymeric moiety selected from poly(alkylene oxide) moieties. Exemplary poly(alkylene oxides) include poly(ethylene glycol) (PEG) and polypropylene glycol) (PPG) moieties.

In one example, the invention provides a method of making a composition that includes a modified nucleotide sugar. In the modified nucleotide sugar, the sugar moiety is covalently linked to a polymeric modifying group, wherein the polymeric modifying group includes at least one linear or branched poly(alkylene oxid) moiety. An exemplary method includes: (i) contacting a reaction mixture comprising the modified nucleotide sugar with an anion exchange medium; (ii) eluting the modified nucleotide sugar from the anion exchange medium thereby forming an eluate fraction containing the modified nucleotide sugar; and (iii) desalting the eluate fraction. Unexpectedly, the inventors have discovered that the process of the invention results in modified nucleotide sugars with high purity and high overall yields, even when the process does not include ultrafiltration prior to anion-exchange chromatography and the reaction mixture is first processed by anion-exchange chromatography (e.g., after conditioning the reaction mixture by removing solvent and particles). Thus, in one example, the method does not include ultrafiltration (e.g., TFF) prior to anion exchange chromatography, i.e., step (i).

In an exemplary embodiment, the above method can further include: (iv) reducing the volume of the reaction mixture. In one example, the volume of the reaction mixture is reduced by evaporation (e.g., under reduced pressure) of at least part of the solvent (e.g., via rotary evaporation). In one example, the reaction mixture includes an organic solvent (e.g., THF), which is essentially removed or partly removed through evaporation under reduced pressure. The above method may further include (e.g., after reducing the volume of the reaction mixture): (v) filtering the reaction mixture (e.g., in order to remove particles). In a typical example, the reaction mixture is filtered through a 0.22 μm filter. The term "filtering" in this context does not include "ultrafiltration". Other suitable filters useful to precondition the reaction mixture for anion-exchange chromatogarphy are described herein. In a particular example, the volume of the reaction mixture is first reduced and the resulting mixture is subjected to filtering before the filtrate is contacted with the anion exchange medium.

In one example, according to any of the above embodiments, the method can further include, e.g., after step (iii): (v) removing water from the eluate fraction. In one example, the water is removed by subjecting the eluate fraction to freeze drying or spray drying. Typically, these procedures result in an essentially dry product, in which the residual water content is, e.g., less than about 10% (w/w), less than about 5% (w/w), less than about 4% (w/w), less than about 3% (w/w), less than about 2% (w/w) or less than about 1% (w/w).

In a particular example, the invention provides a method of making a composition that includes a modified nucleotide-sugar, in which a polymeric modifying group is covalently linked to the nucleotide sugar. In one example, the polymeric modifying group includes at least one linear or branched poly(alkylene oxid) moiety. The method includes: (i) contacting a nucleotide sugar derivative including a primary amino group, with an activated poly(alkylene oxide) moiety incorporating a p-nitrophenyl carbonate moiety under conditions sufficient to form a covalent bond between the amino group of the nucleotide sugar derivative and the poly(alkylene oxide) moiety. The contacting occurs in the presence of an aqueous solvent having a pH between about 8.0 and about 8.8. Hence a reaction mixture is formed, which includes the modified nucleotide sugar. The method can further include: (ii) contacting the reaction mixture with an anion exchange medium and (iii) eluting the modified nucleotide sugar from the anion exchange medium forming an eluate fraction that contains the modified nucleotide sugar. The method can further include: (iv) desalting the eluate fraction using membrane filtration; and (v) removing water from the eluate fraction (e.g., via freeze drying or spray drying optionally in the presence of an additive). The method does preferably not include ultrafiltration prior to step (i).

Exemplary polymeric modifying groups useful in any of the above embodiments are disclosed hereinbelow. In one example, the polymeric modifying group includes at least one polymeric moiety selected from poly(alkylene oxide) moieties. Exemplary poly(alkylene oxides) include poly (ethylene glycol) (PEG) and polypropylene glycol) (PPG). In one example, the PEG modifying group has a molecular weight between about 5 kDa and about 600 kDa, between about 5 kDa and about 500 kDa, between about 5 kDa and about 400 kDa, between about 10 kDa and about 400 kDa, between about 10 kDa and about 300 kDa, between about 10 kDa and about 200 kDa or between about 10 kDa and about 100 kDa. In an particular example, the PEG moiety has a moleculare weight between about 10 kDa and about 80 kDa, between about 10 kDa and about 60 kDa or between about 10 kDa and about 40 kDa. In one example, the polymeric modifying group is branched and includes a glycerol backbone covalently linked to at least two polymeric moieties (e.g., two PEG moieties).

Nucleotide Sugar

The nucleotide sugar or modified nucleotide sugar according to any of the above embodiments includes a nucleoside moiety covalently linked to a phosphate moiety (selected from monophosphate, diphosphate, triphosphate and polyphosphate moieties) and an additional sugar moiety covalently linked to the phosphate moiety. The nucleoside moiety of the nucleotide sugar can be any nucleoside or deoxynucleoside, including adenosine, guanosine, 5-methyluridine, uridine, cytidine, deoxyadenosine, deoxyguanosine, deoxythymidine, deoxyuridine, and deoxycytidine. Additional nucleoside moieties are described herein. The methods of the invention are useful for producing nucleotide sugars, in which the nucleotide is in various states of phosphorylation. Accordingly, exemplary nucleotides of the nucleotide sugar include CMP, CDP, CTP, AMP, cAMP, ADP, ATP, UMP, UDP, UTP, GMP, cGMP, GDP, GTP, TMP, TDP and TTP as well as the deoxy forms of these and other nucleotides, including modified nucleotides.

The sugar moiety of the nucleotide sugar can be any glycosyl moiety including mono- and oligo-saccharides. Exemplary sugar moieties include sialic acid, glucose, GlcNAc, mannose, fucose, galactose, GalNAc and combinations thereof. The term "glycosyl moiety" or "sugar moiety" includes "glycosyl-mimetic moieties".

Exemplary nucleotide sugars include CMP-SA, CDP-SA, CTP-SA, AMP-SA, cAMP-SA, ADP-SA, ATP-SA, UMP-SA, UDP-SA, UTP-SA, GMP-SA, cGMP-SA, GDP-SA, GTP-SA, TMP-SA, TDP-SA and TTP-SA, CMP-GlcNAc, CDP-GlcNAc, CTP-GlcNAc, AMP-GlcNAc, cAMP-GlcNAc, ADP-GlcNAc, ATP-GlcNAc, UMP-GlcNAc, UDP-GlcNAc, UTP-GlcNAc, GMP-GlcNAc, cGMP-GlcNAc, GDP-GlcNAc, GTP-GlcNAc, TMP-GlcNAc, TDP-GlcNAc and TTP-GlcNAc, CMP-Gal, CDP-Gal, CTP-Gal, AMP-Gal, cAMP-Gal, ADP-Gal, ATP-Gal, UMP-Gal, UDP-Gal, UTP-Gal, GMP-Gal, cGMP-Gal, GDP-Gal, GTP-Gal, TMP-Gal, TDP-Gal and TTP-Gal, CMP-GalNAc, CDP-GalNAc, CTP-GalNAc, AMP-GalNAc, cAMP-GalNAc, ADP-GalNAc, ATP-GalNAc, UMP-GalNAc, UDP-GalNAc, UTP-GalNAc, GMP-GalNAc, cGMP-GalNAc, GDP-GalNAc, GTP-GalNAc, TMP-GalNAc, TDP-GalNAc and TTP-GalNAc, CMP-Glc, CDP-Glc, CTP-Glc, AMP-Glc, cAMP-Glc, ADP-Glc, ATP-Glc, UMP-Glc, UDP-Glc, UTP-Glc, GMP-Glc, cGMP-Glc, GDP-Glc, GTP-Glc, TMP-Glc, TDP-Glc and TTP-Glc, CMP-fucose, CDP-fucose, CTP-fucose, AMP-fucose, cAMP-fucose, ADP-fucose, ATP-fucose, UMP-fucose, UDP-fucose, UTP-fucose, GMP-fucose, cGMP-fucose, GDP-fucose, GTP-fucose, TMP-fucose, TDP-fucose and TTP-fucose, CMP-Man, CDP-Man, CTP-Man, AMP-Man, cAMP-Man, ADP-Man, ATP-Man, UMP-Man, UDP-Man, UTP-Man, GMP-Man, cGMP-Man, GDP-Man, GTP-Man, TMP-Man, TDP-Man and TTP-Man, and deoxy variants thereof. Any of the above nucleotide sugars can be part of a modified nucleotide sugar produced by a method of the invention. In a preferred embodiment, the polymeric modifying group (e.g., linear or branched PEG moiety) in these modified nucleotide sugars is covalently attached to the sugar moiety of the nucleotide sugar, optionally via a linker moiety.

Exemplary modified nucleotide sugars that can be produced using methods of the invention include CMP-SA-PEG, CDP-SA-PEG, CTP-SA-PEG, AMP-SA-PEG, cAMP-SA-PEG, ADP-SA-PEG, ATP-SA-PEG, UMP-SA-PEG, UDP-SA-PEG, UTP-SA-PEG, GMP-SA-PEG, SA-PEG, cGMP-SA-PEG, GDP-SA-PEG, GTP-SA-PEG, TMP-SA-PEG, TDP-SA-PEG and TTP-SA-PEG, CMP-GlcNAc-PEG, CDP-GlcNAc-PEG, CTP-GlcNAc-PEG, AMP-GlcNAc-PEG, cAMP-GlcNAc-PEG, ADP-GlcNAc-PEG, ATP-GlcNAc-PEG, UMP-GlcNAc-PEG, UDP-GlcNAc-PEG, UTP-GlcNAc-PEG, GMP-GlcNAc-PEG, cGMP-GlcNAc-PEG, GDP-GlcNAc-PEG, GTP-GlcNAc-PEG, TMP-GlcNAc-PEG, TDP-GlcNAc-PEG and TTP-GlcNAc-PEG, CMP-Gal-PEG, CDP-Gal-PEG, CTP-Gal-PEG, AMP-Gal-PEG, cAMP-Gal-PEG, ADP-Gal-PEG, ATP-Gal-PEG, UMP-Gal-PEG, UDP-Gal-PEG, UTP-Gal-PEG, GMP-Gal-PEG, cGMP-Gal-PEG, GDP-Gal-PEG, GTP-Gal-PEG, TMP-Gal-PEG, TDP-Gal-PEG and TTP-Gal-PEG, CMP-GalNAc-PEG, CDP-GalNAc-PEG, CTP-GalNAc-PEG, AMP-GalNAc-PEG, cAMP-GalNAc-PEG, ADP-GalNAc-PEG, ATP-GalNAc-PEG, UMP-GalNAc-PEG, UDP-GalNAc-PEG, UTP-GalNAc-PEG, GMP-GalNAc-PEG, cGMP-GalNAc-PEG, GDP-GalNAc-PEG, GTP-GalNAc-PEG, TMP-GalNAc-PEG, TDP-GalNAc-PEG and TTP-GalNAc-PEG, CMP-Glc-PEG, CDP-Glc-PEG, CTP-Glc-PEG, AMP-Glc-PEG, cAMP-Glc-PEG, ADP-Glc-PEG, ATP-Glc-PEG, UMP-Glc-PEG, UDP-Glc-PEG, UTP-Glc-PEG, GMP-Glc-PEG, cGMP-Glc-PEG, GDP-Glc-PEG, GTP-Glc-PEG, TMP-Glc-PEG, TDP-Glc-PEG and TTP-Glc-PEG, CMP-fucose-PEG, CDP-fucose-PEG, CTP-fucose-PEG, AMP-fucose-PEG, cAMP-fucose-PEG, ADP-fucose-PEG, ATP-fucose-PEG, UMP-fucose-PEG, UDP-fucose-PEG, UTP-fucose-PEG, GMP-fucose-PEG, cGMP-fucose-PEG, GDP-fucose-PEG, GTP-fucose-PEG, TMP-fucose-PEG, TDP-fucose-PEG and TTP-fucose-PEG, CMP-Man-PEG, CDP-Man-PEG, CTP-Man-PEG, AMP-Man-PEG, cAMP-Man-PEG, ADP-Man-PEG, ATP-Man-PEG, UMP-Man-PEG, UDP-Man-PEG, UTP-Man-PEG, GMP-Man-PEG, cGMP-Man-PEG, GDP-Man-PEG, GTP-Man-PEG, TMP-Man-PEG, TDP-Man-PEG and TTP-Man-PEG, and deoxy variants thereof. Any of the above PE moieties can be replaced with another polymeric moiety, such as a PPG moiety.

In one example, the sugar nucleotide or modified sugar nucleotide of the invention includes cytidine as the nucleoside and sialic acid as the sugar moiety. In a particular example, the sugar nucleotide or modified nucleotide sugar includes cytidine-monophospho-sialic acid (CMP-SA). In another example, the nucleotide sugar is CMP-SA. In a further example, the modified nucleotide sugar is CMP-SA covalently linked to a linear or branched PEG moiety (CMP-SA-PEG).

In one example, the nucleotide sugar according to any of the above embodiments, is a member selected from:

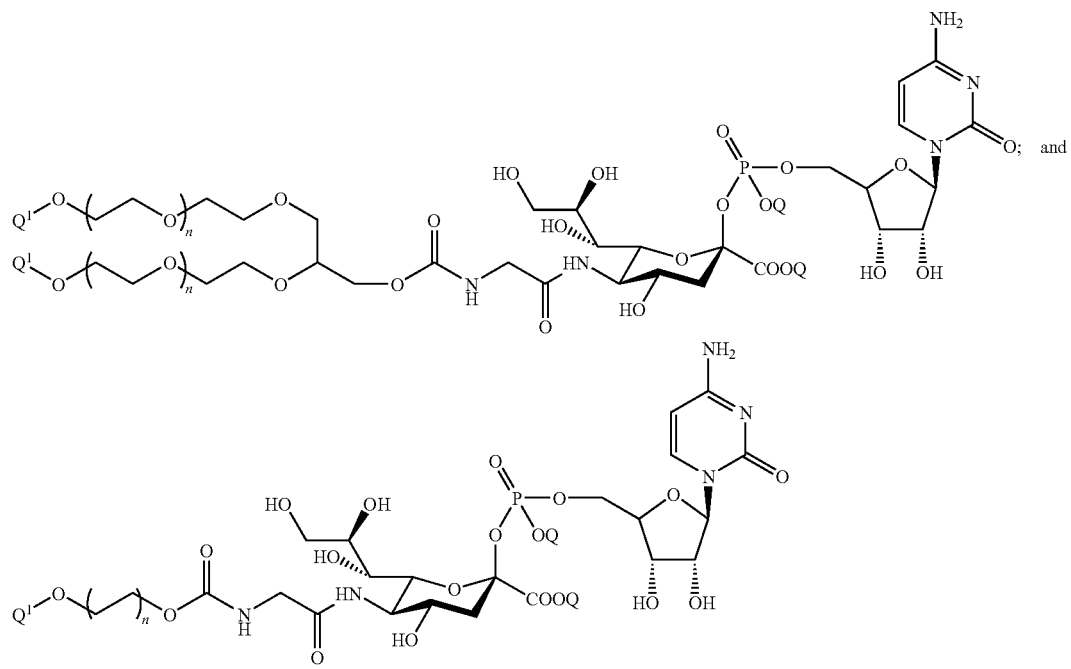

wherein each n is an integer independently selected from 1 to 2500. In one example, n is selected from about 100 to about 1000, from about 100 to about 800, from about 100 to about 600, from about 100 to about 500. Each Q is a member independently selected from H, a negative charge and a salt counter ion (e.g., Na, K). Each $Q^1$ is a member independently selected from H, and $C_1$-$C_6$ alkyl, such as methyl, ethyl, propyl (e.g., n-propyl, iso-propyl), butyl (e.g., n-butyl, iso-butyl), pentyl and hexyl.

In an exemplary embodiment, according to any of the above methods, the anion exchange medium is selected from a quaternary ammonium resin and a dietylaminoethyl (DEAE) resin. In another example, the anion exchange medium is a sepharose resin (e.g., Q-sepharose). Additional anion exchange media are described herein, each of which is equally useful in the methods of the invention. In one example, the anion exchange medium is a quaternary ammonium resin, which includes bicarbonate ions as counter-ions. For example, the quaternary ammonium resin is treated with a bicarbonate buffer (e.g., $NaHCO_3$) prior to use.

In another example, the nucleotide sugar is eluted from the anion exchange medium using a bicarbonate buffer. For example, the nucleotide sugar is eluted using a stepwise elution protocol or a gradient, in which the bicarbonate concentration in the elution buffer is increased from about 0 mM to about 1M bicarbonate (e.g., $NaHCO_3$). Typically, the PEG-modified nucleotide sugar (e.g., CMP-SA-PEG) elutes close to the corresponding modified sugar (e.g., SA-PEG), which is a frequent side product of the coupling reaction used to form the modified nucleotide sugar. Unexpectedly, the inventors have discovered that the nucleotide sugar can be separated from the corresponding modified sugar using low bicarbonate concentrations or slow gradients involving between about 0.01 mM and about 30 mM of bicarbonate. Thus, in one example, the nucleotide sugar is eluted from the anion-exchange medium using a bicarbonate buffer including bicarbonate concentrations between about 0.01 mM and about 50 mM, between about 0.01 mM and about 30 mM, between about 0.01 mM and about 20 mM or between about 0.01 mM and about 10 mM. Other contaminants of the reaction mixture (e.g., nucleosides, non-modified nucleotide sugars) typically elute at bicarbonate concentrations higher than about 30 or 50 mM.

In another exemplary embodiment, the reaction mixture (anion exchange feed solution), which is loaded onto the anion exchange column (i.e., contacted with the anion exchange medium) has a salt conductivity of less than about 10 mS/cm, less than about 8 mS/cm, less than about 6 mS/cm, less than about 5 mS/cm, less than about 4 mS/cm, less than about 3 mS/cm or less than about 2 mS/cm. In one example, the reaction mixture, which is loaded onto the anion-exchange column, has a salt conductivity of less than about 1 mS/cm, less than about 0.8, 0.6, 0.4 or 0.2 mS/cm. The salt conductivity of the reaction mixture can be adjusted prior to anion-exchange chromatography, e.g., by diluting the reaction mixture with water.

In one example according to any of the above embodiments, the desalting of step (iii) is accomplished using membrane filtration, such as ultrafiltration. For example, desalting is accomplished using tangential flow filtration (TFF). Ultrafiltration membranes useful for desalting are known in the art. Exemplary membranes are described herein. In one example, the ultrafiltration membrane has a MWCO that is smaller than the molecular weight of the nucleotide sugar. Hence, the nucleotide sugar is retained by the membrane while salt ions can pass through the membrane filter. For example, the ultrafiltration membrane used for desalting of a nucleotide sugar solution has a the molecular weight cutoff less than about 100 kDa, leass than about 80 kDa, less than about 60 kDa, less than about 40 kDa or less than about 20 kDa. In a particular example, the ultrafiltration membrane has a molecular weight cutoff that is less than about 10 kDa. Ultrafiltration membranes used to desalt CMP-SA-PEGs with PEG moieties between about 10 kDa and 60 kDa, typically have a molecular weight cutoff between about 1 kDa and about 5 kDa.

In one example, the above desalting step (e.g., involving membrane filtration, such as ultrafiltration) results in reduced salt conductivity of the nucleotide sugar solution (e.g., the eluate fraction) compared to the salt conductivity prior to membrane filtration. For example, the reduced salt conductivity of the eluate fraction after membrane filtration is between about 1 µS/cm and about 1000 µS/cm. In a particular example, the salt conductivity of the eluate fraction after membrane filtration is between about 1 µS/cm and about 600 µS/cm, between about 1 µS/cm and about 400 µS/cm, between about 1 µS/cm and about 200 µS/cm, between about 10 µS/cm and about 100 µS/cm, between about 10 µS/cm and about 80 µS/cm, between about 10 µS/cm and about 60 µS/cm, between about 10 µS/cm and about 40 µS/cm, between about 10 µS/cm and about 20 µS/cm or between about 1 µS/cm and about 10 µS/cm. In a preferred example, the salt conductivity during membrane filtration is lowered to less than about 400 µS/cm, less than about 300 µS/cm, less than about 200 µS/cm, less than about 100 µS/cm, less than about 80 µS/cm, less than about 60 µS/cm, less than about 50 µS/cm, less than about 40 µS/cm, less than about 30 µS/cm, less than about 20 µS/cm, less than about 10 µS/cm, less than about 8 µS/cm, less than about 6 µS/cm, less than about 4 µS/cm, less than about 2 µS/cm or less than about 1 µS/cm.

In one example, ultrafiltration (e.g., TFF) is used to reduce the final volume of the eluate fraction or a purified modified nucleotide sugar solution.

Figure 2:
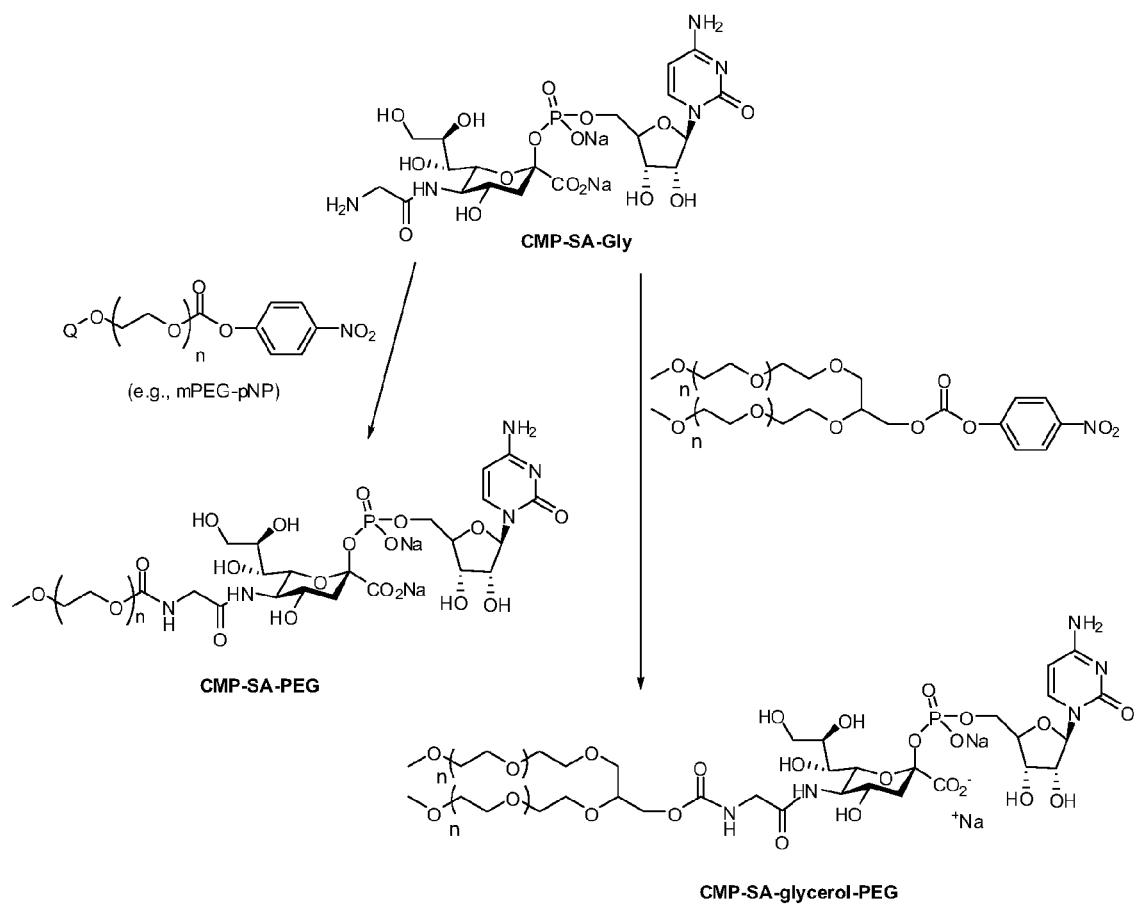
FIG. 2 is a synthetic scheme outlining exemplary methods for the synthesis of CMP-SA-PEGs incorporating linear (e.g., CMP-SA-PEG-10 kDa and CMP-SA-PEG-20 kDa) and branched (e.g., CMP-SA-PEG-glycerol-40 kDa) PEG moieties.

In a particular example, the current invention provides processes for the production of modified cytidine-monophosphate-sialic acid (CMP-SA) nucleotides. Exemplary modified nucleotide sugars, which can be produced using the methods of the invention, include CMP-SA-PEG-10 kDa, CMP-SA-PEG-20 kDa and CMP-SA-glycerol-PEG-40 kDa. Exemplary modified nucleotide sugars (CMP-SA-PEGs) are shown in FIG. 2.

In one example according to any of the above embodiments, the nucleotide sugar produced by the method of the invention (e.g., CMP-SA-PEG) has a purity of at least about 50% (w/w), at least about 60% (w/w), at least about 70% (w/w), at least about 80% (w/w), at least about 85% (w/w), at least about 90% (w/w) or at least about 95% (w/w). In a particular example, the nucleotide sugar produced by a method of the invention has a purity between about 50% and about 100% (w/w), between about 60% and about 100% (w/w), between about 80% and about 100% (w/w) or between about 90% and about 100% (w/w). In another example, the nucleotide sugar produced by a method of the invention has a purity between about 96% and about 100% (w/w), between about 97% and about 100% (w/w), between about 98% and about 100% (w/w) or between about 99% and about 100% (w/w).

Figure 3:
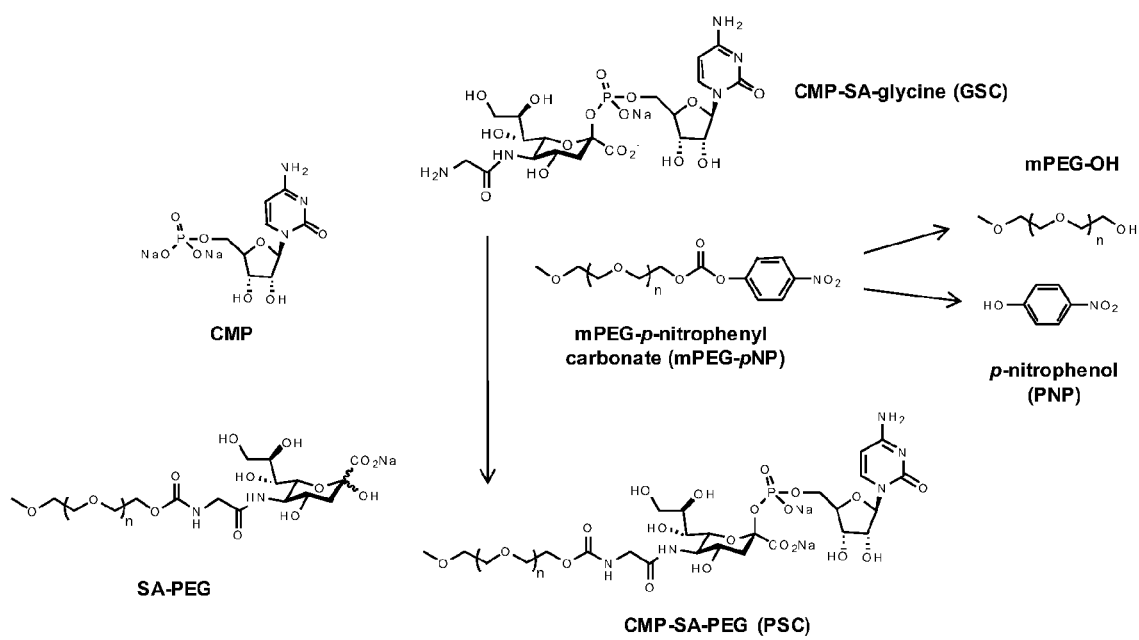
FIG. 3 is a diagram summarizing side-products formed during the synthesis of nucleotide-sugar PEGs (e.g., CMP-SA-PEGs) using a coupling reaction involving a nucleotide sugar derivative (e.g., CMP-SA-glycine) and a PEG-p-nitrophenyl carbonate reagent (e.g., mPEG-pNF). The impurities mPEG-OH and p-nitrophenol (PNP) can be formed during the hydrolysis of mPEG-p-nitrophenyl carbonate. CMP can be formed via hydrolysis of CMP-SA glycine and/or CMP-SA-PEG. SA-PEG can be formed by hydrolysis of CMP-SA-PEG.

In one embodiment, the process of the invention is utilized to purify the nucleotide sugar from other reaction components. In the case of CMP-SA-PEGs the reaction mixture can contain, e.g., mPEG-OH and p-nitrophenol (PNP), e.g., formed during the hydrolysis of mPEG-p-nitrophenyl carbonate. The reaction mixture can further include CMP, e.g., formed via hydrolysis of CMP-SA glycine and/or CMP-SA-PEG. The reaction mixture can further include SA-PEG, e.g., formed by hydrolysis of CMP-SA-PEG, as well as salts (FIG. 3).

In one embodiment, the method of the invention provides a CMP-SA-PEG product that includes less than about 10%, less than about 5%, less than about 4%, less than about 3%, less than about 2% or less than about 1% of CMP (w/w) compared to CMP-SA-PEG. In another embodiment, the method of the invention provides a CMP-SA-PEG that includes less than about 0.9%, less than about 0.8%, less than about 0.7%, less than about 0.6%, less than about 0.5%, less than about 0.4%, less than about 0.3% or less than about 0.2% CMP (w/w) compared to CMP-SA-PEG.

In another embodiment, the method of the invention provides a CMP-SA-PEG product that includes less than about 10%, less than about 5%, less than about 4%, less than about 3%, less than about 2% or less than about 1% of SA-PEG (w/w) compared to CMP-SA-PEG. In another embodiment, the method of the invention provides a CMP-SA-PEG that includes less than about 0.9%, less than about 0.8%, less than about 0.7%, less than about 0.6%, less than about 0.5%, less than about 0.4%, less than about 0.3% or less than about 0.2% SA-PEG (w/w) compared to CMP-SA-PEG.

In another embodiment, the method of the invention provides a CMP-SA-PEG product that includes less than about 10%, less than about 5%, less than about 4%, less than about 3%, less than about 2% or less than about 1% of mPEG-OH (w/w) compared to CMP-SA-PEG. In another embodiment, the method of the invention provides a CMP-SA-PEG that includes less than about 0.9%, less than about 0.8%, less than about 0.7%, less than about 0.6%, less than about 0.5%, less than about 0.4%, less than about 0.3% or less than about 0.2% mPEG-OH (w/w) compared to CMP-SA-PEG.

In another embodiment, the method of the invention provides a CMP-SA-PEG product that includes less than about 10%, less than about 5%, less than about 4%, less than about 3%, less than about 2% or less than about 1% of p-nitrophenol (w/w) compared to CMP-SA-PEG. In another embodiment, the method of the invention provides a CMP-SA-PEG that includes less than about 0.9%, less than about 0.8%, less than about 0.7%, less than about 0.6%, less than about 0.5%, less than about 0.4%, less than about 0.3% or less than about 0.2% of p-nitrophenol (w/w) compared to CMP-SA-PEG.

In another embodiment, the method of the invention provides a CMP-SA-PEG product that includes less than about 10%, less than about 5%, less than about 4%, less than about 3%, less than about 2% or less than about 1% of p-nitrophenol (w/w) compared to CMP-SA-PEG. In another embodiment, the method of the invention provides a CMP-SA-PEG that includes less than about 0.9%, less than about 0.8%, less than about 0.7%, less than about 0.6%, less than about 0.5%, less than about 0.4%, less than about 0.3% or less than about 0.2% of p-nitrophenol (w/w) compared to CMP-SA-PEG.

In another example according to any of the above embodiments, the nucleotide sugar produced by the method of the invention is obtained in an overall yield of at least about 30%, at least about 40%, at least about 50%, at least about 60%, at least about 70%, at least about 80%, at least about 90% or at least about 95%. In a particular example, the nucleotide sugar produced by the method of the invention is obtained in an overall yield between about 50% and about 100%, between about 60% and about 95%, between about 80% and about 95% or between about 90% and about 95%. In another example, the nucleotide sugar produced by the method of the invention is obtained in an overall yield between about 40% and about 90%, between about 50% and about 90%, between about 60% and about 90%, between about 70% and about 90%, between about 80% and about 90%, between about 85% and about 90% (w/w) or between about 85% and about 95%.

In an exemplary embodiment, the modified nucleotide sugar purified by a method of the invention includes a sugar, activated sugar or nucleotide sugar that is conjugated to one or more polymer, e.g. a branched polymer. Exemplary polymers include both water-soluble and water-insoluble species.

Exemplary modified nucleotide sugars substituted with the polymeric modifying group at any position within the sugar moiety of the nucleotide sugar. In an exemplary embodiment, the sugar is substituted with a linker or polymeric modifying group attached through a linker at one or more of C-1, C-2, C-3, C-4 or C-5. In another embodiment, the invention provides a pyranose that is substituted with a linker or modifying group attached to the sugar through a linker at one or more of C-1, C-2, C-3, C-4, C-5 or C-6. Preferably, the linker and/or modifying group is attached directly to an oxygen, nitrogen or sulfur pendent from the carbon of the sugar.

In a presently preferred embodiment, the polymeric linker or modifying group is appended to a position that is selected such that the resulting conjugate functions as a substrate for an enzyme used to ligate the modified sugar moiety to another species, e.g., peptide, glycopeptide, lipid, glycolipid, etc. Exemplary enzymes are known in the art and include glycosyl transferases (sialyl transferases, glucosyl transferases, galactosyl transferases, N-acetylglucosyl transferases, N-acetylgalactosyl transferases, mannosyl transferases, fucosyl transferases, etc.). Exemplary sugar nucleotide and activated sugar conjugates of the invention also include substrates for mutant glycosidases and mutant glycoceramidases that are modified to have synthetic, rather than hydrolytic activity.

In an exemplary embodiment, the nucleotide sugar purified by a method of the invention has a formula selected from:

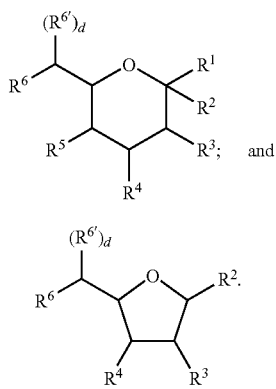

I

II

In Formulae I and II, $R^1$ is H, $CH_2OR^7$, $COOR^7$ or $OR^7$, in which $R^7$ represents H, substituted or unsubstituted alkyl or substituted or unsubstituted heteroalkyl. $R^2$ is H, OH, NH or a moiety that includes a nucleotide. An exemplary $R^2$ species according to this embodiment has the formula:

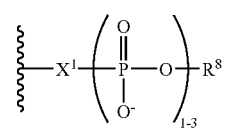

in which $X^1$ represents O or NH and $R^8$ is a nucleoside.

The symbols $R^3$, $R^4$, $R^5$, $R^6$ and $R^{6'}$ independently represent H, substituted or unsubstituted alkyl, $OR^9$, NHC(O)$R^{10}$. The index d is 0 or 1. $R^9$ and $R^{10}$ are independently selected from H, substituted or unsubstituted alkyl, substituted or unsubstituted heteroalkyl or sialic acid. At least one of $R^3$, $R^4$, $R^5$, $R^6$, and $R^{6'}$ includes the linker or linker-modifying group, e.g., PEG. In an exemplary embodiment, $R^6$ and $R^{6'}$, together with the carbon to which they are attached are components of the side chain of sialic acid. In still a further exemplary embodiment, this side chain is modified with the linker or linker-modifying moiety at one or more of C-6, C-7 or C-9.

In an exemplary embodiment, the linker arm has the structure below when w is 0, and when w is greater than 0, a modifying group is joined to the sugar core through the linker:

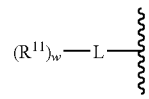

in which $R^{11}$ is the polymeric moiety and L is selected from a bond and a linking group, and w is an integer from 1-6, preferably 1-3 and more preferably, 1-2.

When L is a bond it is formed between a reactive functional group on a precursor of $R^{11}$ and a reactive functional group of complementary reactivity on a precursor of L. As set forth herein, the selection and preparation of precursors with appropriate reactive functional groups is within the ability of those skilled in the art. Moreover, combining the precursors proceeds by chemistries that are well-understood in the art.

In an exemplary embodiment L is a linking group that is formed from an amino acid, an amino acid mimetic, or small peptide (e.g., 1-4 amino acid residues) providing a modified sugar. In another embodiment, the modifying group is attached through the linker, e.g., a polymeric modifying moiety is attached through a substituted alkyl linker. The linker is formed through reaction of an amine moiety and carboxylic acid (or a reactive derivative, e.g., active ester, acid halide, etc.) of the amino acid with groups of complementary reactivity on the precursors to L and $R^{11}$. The elements of the conjugate can be conjugated in essentially any convenient order. For example the precursor to L can be in place on the saccharide core prior to conjugating the precursors of $R^{11}$ and L. Alternatively, an $R^{11}$-L cassette, bearing a reactive functionality on L can be prepared and subsequently linked to the saccharide through a reactive functional group of complementary reactivity on this species.

In an exemplary embodiment, the linker and/or modifying moiety is $R^3$ and/or $R^6$. In another exemplary embodiment, $R^3$ and/or $R^6$ includes both the polymeric modifying moiety and a linker, L, joining the polymeric moiety to the remainder of the molecule. In another exemplary embodiment, the modifying moiety is $R^3$. In a further exemplary embodiment, $R^3$ includes both the modifying group and a linker, L, joining the modifying group to the remainder of the molecule. In yet another exemplary embodiment in which the sugar is a sialic acid, the linker and/or modifying group is at $R^5$ or attached at a position of the sialic acid side chain, e.g., C-9.

In an exemplary embodiment, the present invention provides a method of purifying a sugar or activated sugar conjugate or nucleotide sugar conjugate that is formed between a linear polymer, such as a water-soluble or water-insoluble polymer. In these conjugates, the polymer is attached to a sugar, activated sugar or sugar nucleotide. As discussed herein, the polymer is linked to the sugar moiety, either directly or through a linker An exemplary compound according to this embodiment has a structure according to Formulae (I) or (II), in which at least one of $R^1$, $R^3$, $R^4$, $R^5$ or $R^6$ has the formula:

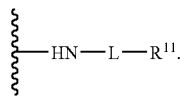

$R^{11}$ is present or absent. In this embodiment, an exemplary linker is derived from a natural or unnatural amino acid, amino acid analogue or amino acid mimetic, or a small peptide formed from one or more such species. For example, certain branched polymers found in the compounds purified by methods of the invention have the formula:

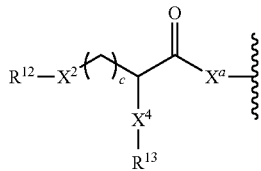

$X^a$ is a linking moiety that is formed by the reaction of a reactive functional group on a precursor of the branched polymeric modifying moiety and the sugar moiety, or a precursor to a linker. For example, when $X^{3'}$ is a carboxylic acid, it can be activated and bound directly to an amine group pendent from an amino-saccharide (e.g., GalNH$_2$, GlcNH$_2$, ManNH$_2$, etc.), forming an $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

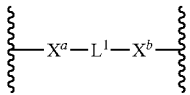

in which $X^b$ is a linking moiety and is independently selected from those groups set forth for $X^a$, and $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), (O)CNH and NHC(O)O, and OC(O)NH.

Another example according to this embodiment has the formula:

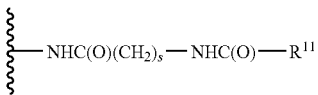

in which s is an integer from 0 to 20 and $C(O)R^{11}$ is present or absent and, when present, $R^{11}$ is a modifying group.

When the modifying group is a PEG moiety, the PEG moieties can have any molecular weight, e.g., 2 kDa, 5 kDa, 10 kDa, 20 kDa, 30 kDa and 40 kDa are of use in the present invention.

Exemplary nucleosides include AMP, UMP, GMP, CMP, TMP, ADP, UDP, GDP, CDP, TDP, ATP, UTP, GTP, CTP, TTP, cAMP and cGMP.

In a preferred embodiment, the sugar purified by the method of the invention includes a sialic acid modified with a linker group. Preferred sites for such modification are $R^5$, $R^6$ or $R^{6'}$. Thus, in a preferred embodiment, at least one of $R^1$ and $R^2$ includes a linker. An exemplary linker is a glycyl linker.

In another preferred embodiment, the nucleotide sugar purified by the methods set forth herein has the formula:

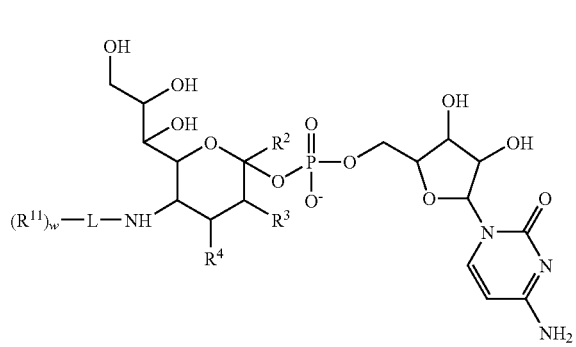

in which the radicals are as discussed above, and $R^{11}$ is a modifying group which is present or absent.

In one embodiment, the modified sialic acid (nucleotide sugar derivative) has the following structure:

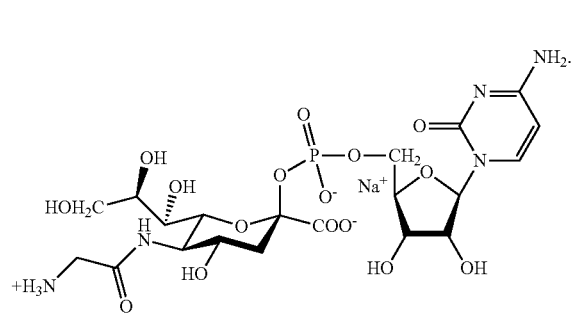

In yet another embodiment, a modifying group is attached to the sialic acid through the linker. An exemplary species according to this description includes a modifying group attached through the primary amino group of the linker. An exemplary modifying group is a water-soluble polymer, such as poly(ethylene glycol) and polypropylene glycol).

In another embodiment, the nucleotide sugar produced by a method of the invention the formula:

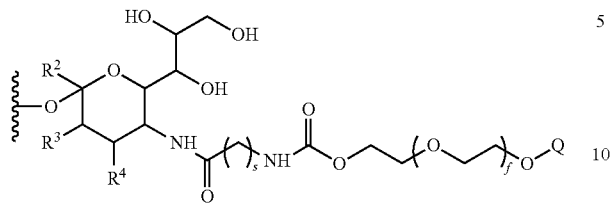

wherein

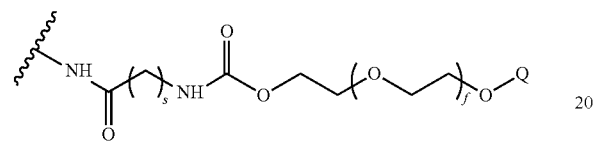

is a linker-modifying group. The index s is an integer selected from 1 to 20. The index f is an integer selected from 1 to 2500. Q is a member selected from H and substituted or unsubstituted $C_1$-$C_6$ alkyl.

Exemplary PEG moieties included as modifying groups in the modified nucleotide sugars of the invention include, but are not limited to:

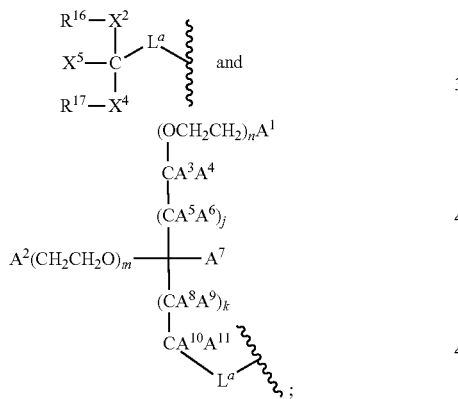

wherein $L^a$ is a linker selected from a bond, substituted or unsubstituted alkyl and substituted or unsubstituted heteroalkyl. The symbols $X^5$, $R^{16}$ and $R^{17}$ independently represent polymeric moieties and non-reactive groups. $X^2$ and $X^4$ represent independently selected linkage fragments joining polymeric moieties $R^{16}$ and $R^{17}$ to C The indices m and n are integers independently selected from 0 to 5000.

The symbols $A^1$, $A^2$, $A^3$, $A^4$, $A^5$, $A^6$, $A^7$, $A^8$, $A^9$, $A^{10}$ and $A^{11}$ independently represent H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$NA^{12}A^{13}$, —$OA^{12}$ or —$SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Exemplary linkage fragments for $X^2$ and $X^4$ include $CH_2$, S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_aO$, $(CH_2)_aS$ or $(CH_2)_aY'$—PEG or $(CH_2)_aY'$—PEG wherein Y' is S or O and a is an integer from 1 to 50.

In an exemplary embodiment, the polymeric modifying group has a structure according to the following formulae:

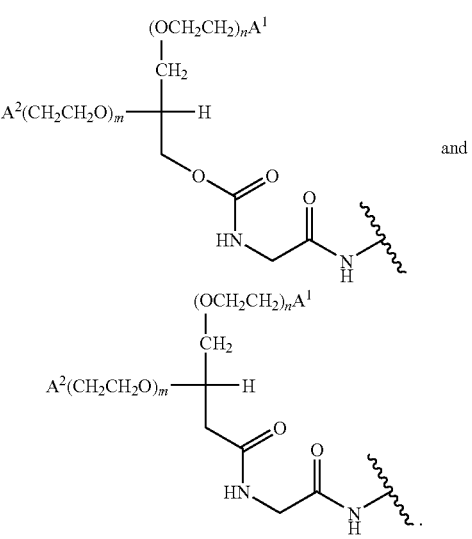

In another exemplary embodiment according to the formula above, the polymeric modifying group has a structure according to the following formula:

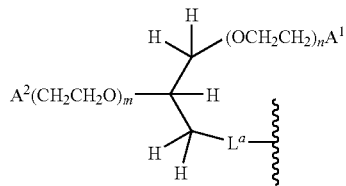

In an exemplary embodiment, $A^1$ and $A^2$ are each members selected from —OH and —$OCH_3$.

Exemplary linker-polymeric modifying groups according to this embodiment include:

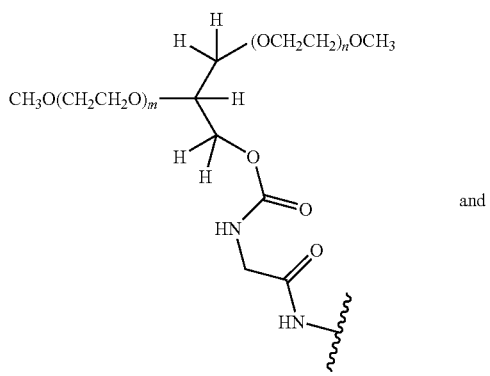

-continued

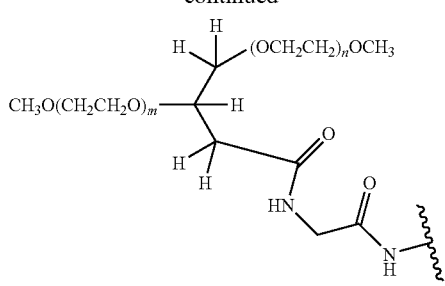

Further specific embodiments of linear and branched polymers, e.g., PEGs, of use in the invention include:

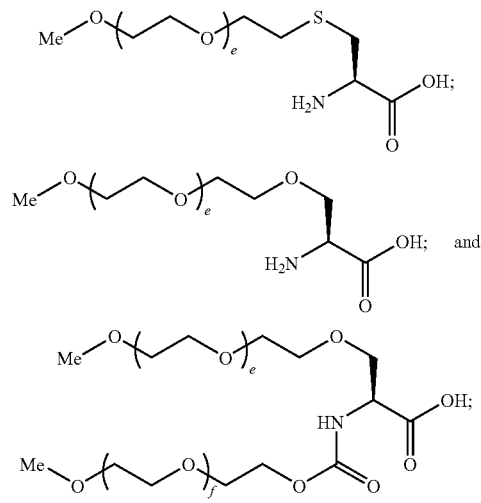

and carbonates and active esters of these species, such as:

can be used to form the linear and branched polymeric species, linker arm conjugates of these species and conjugates between these compounds and sugars and nucleotide sugars.

Other exemplary activating, or leaving groups, appropriate for activating linear PEGs of use in preparing the compounds set forth herein include, but are not limited to the species:

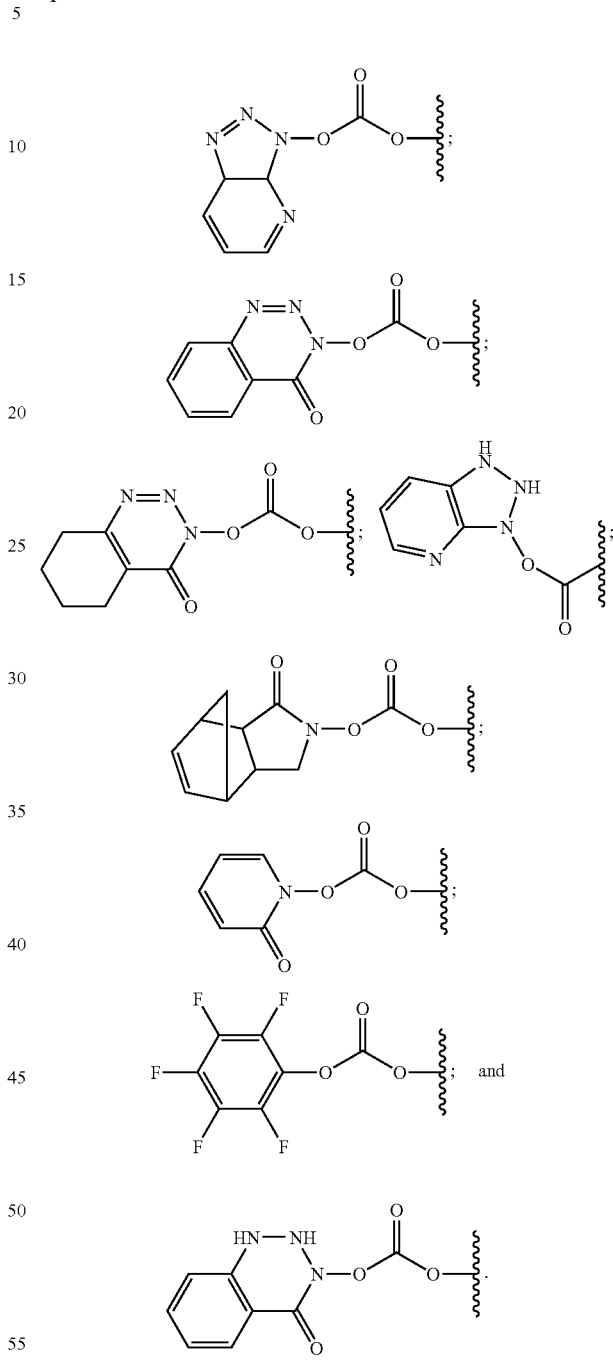

It is well within the abilities of those of skill in the art to select an appropriate activating group for a selected moiety on the precursor to the polymeric modifying moiety.

PEG molecules that are activated with these and other species and methods of making the activated PEGs are set forth in WO 04/083259.

In exemplary embodiments, the branched polymer is a PEG is based upon a cysteine, serine, lysine, di- or tri-lysine core. Thus, further exemplary branched PEGs include:

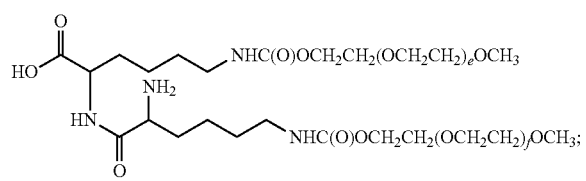
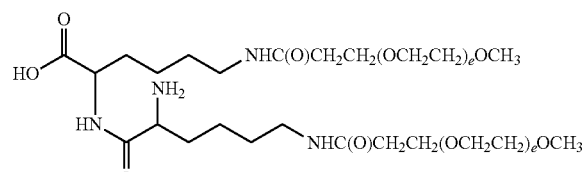
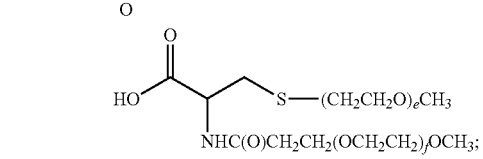
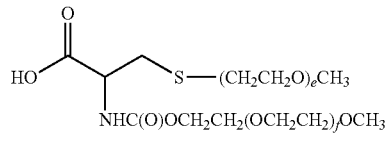
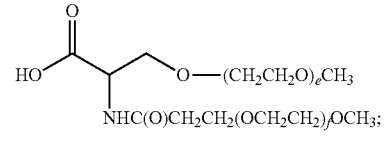
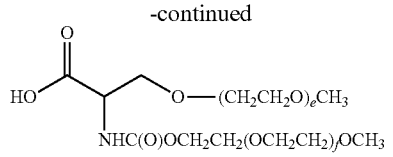
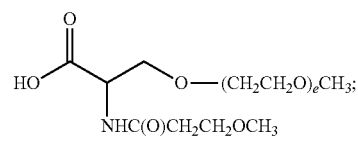
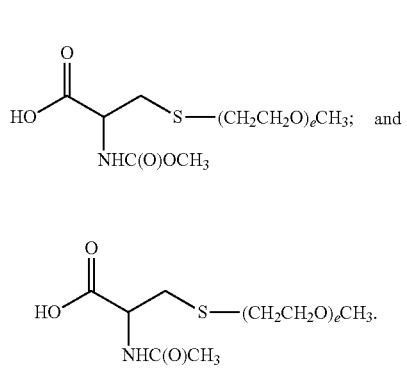
In yet another embodiment, the branched PEG moiety is based upon a tri-lysine peptide. The tri-lysine can be mono-, di-, tri-, or tetra-PEG-ylated. Exemplary species according to this embodiment have the formulae:
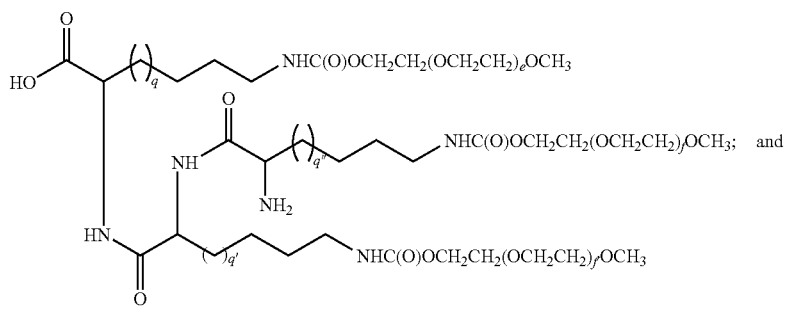
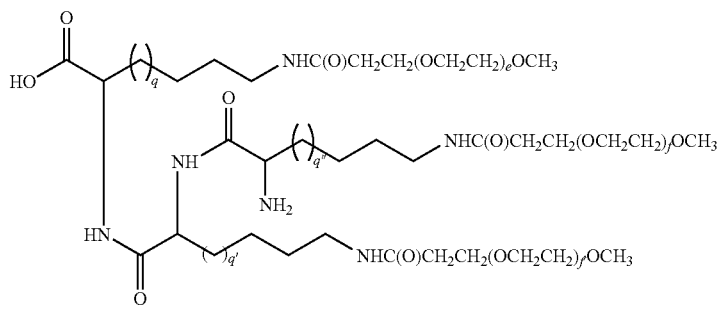

in which e, f and f' are independently selected integers from 1 to 2500; and q, q' and q" are independently selected integers from 1 to 20.

In exemplary embodiments of the invention, the PEG is m-PEG (5 kD, 10 kD, or 20 kD). An exemplary branched PEG species is a serine- or cysteine-(m-PEG)$_2$ in which the m-PEG is a 20 kD m-PEG.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits is within the scope of the invention.

Those of skill in the art will appreciate that one or more of the m-PEG arms of the branched polymer can be replaced by a PEG moiety with a different terminus, e.g., OH, COOH, NH$_2$, C$_2$-C$_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

In an exemplary embodiment, L$^a$ is attached to a free amine moiety of the linker arm, e.g., glycyl linker, through an amine, amide or urethane bond.

In another exemplary embodiment, the PEG is a linear PEG. Similar to the branched PEG species, the linear PEG can be attached to an amine moiety of the linker arm through an amine, amide or urethane linkage.

In a presently preferred embodiment, the saccharides described above are converted to their nucleoside analogues, derivatives including a linker arm, analogues in which a modifying group is attached to a sugar residue of the saccharide directly or through a linker, and nucleotide adducts of each of these motifs.

Formation of the Modified Nucleotide Sugar

In another example according to any of the above embodiments, the method further includes: (vi) forming the modified nucleotide sugar. In one example, the modified nucleotide sugar is formed by contacting a nucleotide sugar derivative that includes a reactive functional group (e.g., a primary amino group) with an activated polymeric reagent, for example an activated poly(alkylene oxide) reagent. The polymeric reagent may be activated by incorporating an activated ester moiety (e.g., NHS-ester), an acid chloride group or an activated carbonate (e.g., p-nitrophenyl carbonate) moiety. Exemplary activated polymeric reagents include a p-nitrophenyl moiety. A person of skill in the art will appreciate that any coupling reaction suitable for conjugating two reaction partners can be used to covalently link the nucleotide sugar to a modifying group. The term "nucleotide sugar derivative" is any nucleotide sugar incorporating a reactive functional group useful to form a covalent bond with another reactive functional group on the polymeric modifying group. Exemplary reactive functional groups include nucleophilic groups, such as amino groups, hydroxyl groups and sulfhydryl groups. Exemplary electrophilic reactive functional groups include activated esters, p-nitrophenyl carbonates, acid chlorides and the like.

In one example, the modified nucleotide sugar is formed by contacting a nucleotide sugar derivative that includes a primary amino group with an activated poly(alkylene oxide) moiety under conditions sufficient to form a covalent bond between the amino group of the nucleotide sugar derivative and the poly(alkylene oxide) moiety. In one example, the nucleotide sugar derivative is a nucleotide sugar covalently linked to a glycine moiety. In another example, the nucleotide sugar derivative is selected from CMP-SA-glycine, AMP-SA-glycine, UMP-SA-glycine, GMP-SA-glycine, CMP-SA-glycine, TMP-SA-glycine, ADP-SA-glycine, UDP-SA-glycine, GDP-SA-glycine, CDP-SA-glycine, TDP-SA-glycine, ATP-SA-glycine, UTP-SA-glycine, GTP-SA-glycine, CTP-SA-glycine, TTP-SA-glycine, cAMP-SA-glycine and cGMP-SA-glycine, wherein the sialic acid moiety (SA) is optionally replaced with another sugar moiety (e.g., Glc, GlcNAc, Gal, GalNAc, fucose, mannose, xylose) and/or the glycine moiety is optionally replaced with another linker moiety providing a reactive functional group.

In one example, the nucleotide sugar derivative used in the methods of the invention is enzymatically synthesized from a nucleotide and a sugar in the presence of an enzyme, such as a glycosyltransferase (e.g., sialyltransferase). Exemplary methods for the synthesis and purification of nucleotide sugar derivatives as well as exemplary enzymes are disclosed in WO2007/056191, filed November 3, the disclosure of which is incorporated herein in its entirety.

In one example according to any of the above embodiment, the nucleotide sugar derivative, which includes a primary amino group and the activated polymeric moiety, which includes a p-nitrophenyl carbonate moiety (e.g., poly (ethylene glycol)-p-nitrophenylcarbonate) are contacted in the presence of an aqueous solvent having a pH between about 8.0 and 9.0, between 8.0 and about 8.9 or between about 8.0 and about 8.8.

Unexpectedly, the inventors have discovered that a pH range between about 8.0 and about 8.8 in an aqueous solvent system is critical during the coupling reaction between an activated polymeric modifying group that includes a p-nitrophenyl (pNP) carbonate moiety, such as PEG-p-nitrophenyl carbonates (e.g., mPEG-p-nitrophenyl) and the nucleotide sugar deivative, (e.g., CMP-SA-glycine). The optimized pH range (above pH 7.0) largely reduces the formation of side-products due to hydrolysis of the reaction partners and products, and thus significantly increases yields and purities for the final products. For example, below pH 7.0, CMP-SA-glycine and CMP-SA-PEG decomposed due to hydrolysis to form CMP, sialic acid-glycine and sialic acid-PEG. Exemplary decomposition products are shown in FIG. 3. An initial pH between about 8.0 and about 8.8 (e.g., about 8.6 to about 8.7) of the reaction mixture was critical in achieving the highest conversion yields. The optimum pH range throughout the process was between about 8.0 and about 8.8. When the pH dropped below 8.0, the reaction slowed dramatically resulting in poor conversion yields.

For example, CMP-SA-PEGs (e.g., CMP-SA-PEG-10 kDa, CMP-SA-PEG-20 kDa and CMP-SA-glycerol-PEG-40 kDa) can be prepared by reacting CMP-SA-Glycine (GSC) with a PEG reagent incorporating a p-nitrophenyl carbonate moiety (e.g. linear or branched 10 kDa, 20 kDa, 40 kDa, 60 kDa, 80 kDa, 100 kDa molecular weight PEG reagents). An exemplary synthetic route according to this embodiment is outlined in FIG. 2. The current invention provides improved methods, in which the CMP-SA-PEGs are obtained in greater purity and in better overall yields than during known processes.

Anion Exchange Chromatography

In an exemplary embodiment a sample containing the nucleotide sugar of interest is loaded onto an anion exchanger in a loading buffer comprising a salt concentration below the concentration at which the nucleotide sugar would elute from the column. In one example, the pH of the buffer is selected so that the nucleotide sugar is retained on the anion exchange medium. Changing the pH of the buffer alters the charge of the nucleotide sugar, and lowering the pH value shortens the retention time with anion exchangers. Alternatively, the anion exchange conditions are selected to preferentially bind impurities, while the purified peptide is found in the flow-through.

The column may be washed with several column volumes (CV) of buffer to remove unbound substances and/or those substances that bind weakly to the resin. Fractions are then eluted from the column using, for example, a bicarbonate gradient according to conventional methods. The salt in the solution competes with the nucleotide sugar in binding to the column and the nucleotide sugar is released. Components with weak ionic interactions elute at a lower salt concentration than components with a strong ionic interaction. Sample fractions are collected from the column. Fractions containing high levels of the desired nucleotide sugar and low levels of impurities are pooled or processed separately.

Anion exchange media are known to those of skill in the art. Exemplary anion exchange media are described, e.g., in *Protein Purification Methods, A Practical Approach*, Ed. Harris E L V, Angal S, IRL Press Oxford, England (1989); *Protein Purification*, Ed. Janson J C, Ryden L, VCH-Verlag, Weinheim, Germany (1989); *Process Scale Bioseparations for the Biopharmaceutical Industry*, Ed. Shukla A A, Etzel M R, Gadam S, CRC Press Taylor & Francis Group (2007), pages 188-196; *Protein Purification Handbook*, GE Healthcare 2007 (18-1132-29) and *Protein Purification, Principles, High ResolutionMethods and Applications* ($2^{nd}$ Edition 1998), Ed. Janson J-C and Ryden L, the disclosures of which are are incorporated herein by reference in their entirety. An exemplary anion exchanger of the invention is selected from quaternary ammonium resins and DEAE resins. In one embodiment, the anion exchanger is a quaternary ammonium resin (e.g. Mustang Q ion exchange membrane, Pall Corporation). Other useful resins include QXL, Capto and BigBeads resins. In one example, the anion exchanger is Sartobind Q.

Exemplary anion exchange media and exemplary manufacturers are summarized below:
GE Healthcare:
Q-Sepharose FF
Q-Sepharose BB
Q-Sepharose XL
Q-Sepharose HP
Mini Q
Mono Q
Mono P
DEAE Sepharose FF
Source 15Q
Source 30Q
Capto Q
ANX Sepharose 4 FF (high sub)
Streamline DEAE
Streamline QXL
Applied Biosystems:
Poros HQ 10 and 20 um self pack
Poros HQ 20 and 50 um bulk media
Poros PI 20 and 50 um
Poros D 50 um
Tosohaas:
Toyopearl DEAE 650S, M and C
Super Q 650
QAE 550C
Pall Corporation:
DEAE Hyper D
Q Ceramic Hyper D
Mustang Q membrane absorber
Merck KGgA:
Fractogel DMAE
FractoPrep DEAE
Fractoprep TMAE
Fractogel EMD DEAE
Fractogel EMD TMAE
Sartorious: Sartobind Q Membrane Absorber The anion exchangers used in the methods of the invention are optionally membrane adsorbers rather than chromatographic resins or supports. The membrane adsorber is optionally disposable.

Desalting

In one embodiment, the mixture containing the nucleotide sugar of interest is desalted subsequent to anion exchange chromatography.

Desalting of nucleotide sugar solutions is achieved using membrane filters wherein the membrane filter has a MWCO smaller than the nucleotide sugar of interest. The nucleotide sugar is found in the retentate and is reconstituted in a buffer of choice (e.g., water). The MWCO of the membrane used for desalting of the nucleotide sugar must be relatively small in order to avoid leaking of the nucleotide sugar through the membrane pores. For example, the MWCO of the ultrafiltration membrane is between about 1 kDa and 10 kDa (e.g. a pore size of about 5 kDa).

In one embodiment, desalting of the nucleotide sugar is accomplished using size-exclusion chromatography (e.g. gel filtration). The technique separates molecules on the basis of size. Typically, high molecular weight components can travel through the column more easily than smaller molecules, since their size prevents them from entering bead pores. Accordingly, low-molecular weight components take longer to pass through the column. Thus, low molecular weight materials, such as unwanted salts, can be separated from the nucleotide sugar of interest.

In an exemplary embodiment, the column material is selected from dextran, agarose, and polyacrylamide gels, in which the gels are characterized by different particle sizes. In another exemplary embodiment, the material is selected from rigid, aqueous-compatible size exclusion materials. An exemplary gel filtration resin of the invention is Sepharose G-25 resin (GE Healthcare).

In an exemplary embodiment, desalting is performed subsequent to anion-exchange chromatography (e.g. after Q-sepharose chromatography).

To purify nucleotide sugars according to the methods of the invention, a membrane is selected that is appropriate for separating the desired carbohydrate from the undesired components (contaminants) of the solution from which the carbohydrate is to be purified. The goal in selecting a membrane is to optimize for a particular application the molecular weight cutoff (MWCO), membrane composition, permeability, and rejection characteristics, that is, the membrane's total capacity to retain specific molecules while allowing other species, e.g., salts and other, generally smaller or opposite charged molecules, to pass through. The percent retention of a component i ($R_i$) is given by the formula $R_i=(1-C_{ip}/C_{ir})\times100\%$, wherein $C_{ip}$ is the concentration of component i in the permeate and $C_{ir}$ is the concentration of component i in the retentate, both expressed in weight percent. The percent retention of a component is also called the retention characteristic or the membrane rejection coefficient.

In an exemplary embodiment, a membrane is chosen that has a high rejection ratio for the nucleotide sugar of interest relative to the rejection ratio for compounds from which separation is desired. If a membrane has a high rejection ratio for a first compound relative to a second compound, the concentration of the first compound in the permeate solution which passes through the membrane is decreased relative to that of the second compound. Conversely, the concentration of the first compound increases relative to the concentration of the second compound in the retentate. If a membrane does not reject a compound, the concentration of the compound in both the permeate and the reject portions will remain essentially the same as in the feed solution. It is also possible for a membrane to have a negative rejection rate for a compound if the compound's concentration in the permeate becomes greater than the compound's concentration in the feed solution. A general review of membrane technology is found in "Membranes and Membrane Separation Processes," in Ullmann's *Encyclopedia of Industrial Chemistry* (VCH, 1990); see also, Noble and Stern, *Membrane Separations Technology: Principles and Applications* (Elsevier, 1995).

As a starting point, one will generally choose a membrane having a molecular weight cut-off (MWCO, which is often related to membrane pore size) that is expected to retain the desired compounds while allowing an undesired compound present in the feed stream to pass through the membrane. The desired MWCO is generally less than the molecular weight of the compound being purified, and is typically greater than the molecular weight of the undesired contaminant that is to be removed from the solution containing the compound being purified. For example, to purify a compound having a molecular weight of 200 Da, one would choose a membrane that has a MWCO of less than about 200 Da. A membrane with a MWCO of 100 Da, for example, would also be a suitable candidate. The membranes that find use in the present invention are classified in part on the basis of their MWCO as ultrafiltration (UF) membranes, nanofiltration (NF) membranes, or reverse osmosis (RO) membranes, depending on the desired separation. For purposes of this invention, UF, NF, and RO membranes are classified as defined in the *Pure Water Handbook*, Osmonics, Inc. (Minnetonka Minn.). RO membranes typically have a nominal MWCO of less than about 200 Da and reject most ions, NF membranes generally have a nominal MWCO of between about 150 Da and about 5 kDa, and UF membranes generally have a nominal MWCO of between about 1 kDa and about 300 kDa (these MWCO ranges assume a saccharide-like molecule). A presently preferred utrafiltration membrane of use in purifying a nucleotide sugar PEG conjugate has a molecular weight cutoff of 19 Kd.

A second parameter that is considered in choosing an appropriate membrane for a particular separation is the polymer type of the membrane. Exemplary membranes of use in the invention are made of conventional membrane material whether inorganic, organic, or mixed inorganic and organic. Typical inorganic materials include glasses, ceramics, cermets, metals and the like. Ceramic membranes, which are preferred for the UF zone, may be made, for example, as described in U.S. Pat. No. 4,692,354 to Asaeda et al, U.S. Pat. No. 4,562,021 to Alary et al., and others. The organic materials which are preferred for the NF and RO applications, are typically polymers, whether isotropic, or anisotropic with a thin layer or "skin" on either the bore side or the shell side of the fibers. Preferred materials for fibers are polyamides, polybenzamides, polysulfones (including sulfonated polysulfone and sulfonated polyether sulfone, among others), polystyrenes, including styrene-containing copolymers such as acrylo-nitrile-styrene, butadiene-styrene and styrene-vinylbenzylhalide copolymers, polycarbonates, cellulosic polymers including cellulose acetate, polypropylene, poly(vinyl chloride), poly(ethylene terephthalate), polyvinyl alcohol, fluorocarbons, and the like, such as those disclosed in U.S. Pat. Nos. 4,230,463, 4,806,244, and 4,259,183. The NF and RO membranes often consist of a porous support substrate in addition to the polymeric discrimination layer.

Of particular importance in selecting a suitable membrane composition is the membrane surface charge. Within the required MWCO range, a membrane is selected that has a surface charge that is appropriate for the ionic charge of the carbohydrate and that of the contaminants. While MWCO for a particular membrane is generally invariable, changing the pH of the feed solution can affect separation properties of a membrane by altering the membrane surface charge. For example, a membrane that has a net negative surface charge at neutral pH can be adjusted to have a net neutral charge simply by lowering the pH of the solution. An additional effect of adjusting solution pH is to modulate the ionic charge on the contaminants and on the carbohydrate of interest. Therefore, by choosing a suitable membrane polymer type and pH, one can obtain a system in which both the contaminant and the membrane are neutral, facilitating pass-through of the contaminant. If, for instance, a contaminant is negatively charged at neutral pH, it is often desirable to lower the pH of the feed solution to protonate the contaminant. For example, removal of phosphate is facilitated by lowering the pH of the solution to at least about 3, preferably to at least about 4, more preferably to at least about 5 and still more preferably to at least about 6, which protonates the phosphate anion, allowing passage through a membrane. For purification of an anionic carbohydrate, the pH will generally between about pH 1 and about pH 7, preferably between about 3 to about 7 and more preferably from about 4 to about 6. Conversely, if contaminant has a positive surface charge, the pH of the feed solution can be adjusted to between about pH 7 and about pH 14. For example, increasing the pH of a solution containing a contaminant having an amino group ($-NH_3^+$) will make the amino group neutral, thus facilitating its passage through the membrane. Thus, one aspect of the invention involves modulating a separation by adjusting the pH of a solution in contact with the membrane; this can change the ionic charge of a contaminant and can also affect the surface charge of the membrane, thus facilitating purification if the desired carbohydrate. Of course, the manufacturer's instructions must be followed as to acceptable pH range for a particular membrane to avoid damage to the membrane.

For some applications, a mixture is first subjected to nanofiltration or reverse osmosis at one pH, after which the retentate containing the nucleotide sugar of interest is adjusted to a different pH and subjected to an additional round of membrane purification. For example, filtration of a reaction mixture used to synthesize sialyl lactose through an Osmonics MX07 membrane (a nanofiltration membrane having a MWCO of about 500 Da) at pH 3, preferably at least about 4, more preferably at least about 5 and still more preferably at least about 6 will retain the sialyl lactose and remove most phosphate, pyruvate, salt and manganese from the solution, while also removing some of the GlcNAc, lactose, and sialic acid. Further recirculation through the MX07 membrane after adjusting the pH of the retentate to about 7, e.g., 7.4, will remove most of the remaining phosphate, all of the pyruvate, all of the lactose, some of the sialic acid, and substantial amounts of the remaining manganese.

If a nucleotide sugar is to be purified from a mixture that contains proteins, such as enzymes used to synthesize a desired oligosaccharide or nucleotide sugar, it is often desirable to remove the proteins as a first step of the purification procedure. For a nucleotide sugar that is smaller than the proteins, this separation is accomplished by choosing a membrane that has an MWCO which is less than the molecular mass of the protein or other macromolecule to be removed from the solution, but is greater than the molecular mass of the oligosaccharide being purified (i.e., the rejection ratio in this case is higher for the protein than for the desired saccharide). Proteins and other macromolecules that have a molecular mass greater than the MWCO will thus be rejected by the membrane, while the nucleotide sugar will pass through the membrane. Conversely, if an oligosaccharide or nucleotide sugar is to be purified from proteins that are smaller than the oligosaccharide or nucleotide sugar, a membrane is used that has a MWCO that is larger than the molecular mass of the protein but smaller than that of the oligosaccharide or nucleotide sugar. Generally, separation of proteins from carbohydrates will employ membranes that are commonly referred to as ultrafiltration (UF) membranes. UF membranes that are suitable for use in the methods of the invention are available from several commercial manufacturers, including Millipore Corp. (Bedford, Mass.), Osmonics, Inc. (Minnetonka, Minn.), Filmtec (Minneapolis, Minn.), UOP, Desalination Systems, Advanced Membrane Technologies, and Nitto.

The invention also provides methods for removing salts and other low molecular weight components from a mixture containing a nucleotide sugar of interest by using a nanofiltration (NF) or a reverse osmosis (RO) membrane. Nanofiltration membranes are a class of membranes for which separation is based both on molecular weight and ionic charge. These membranes typically fall between reverse osmosis and ultrafiltration membranes in terms of the size of species that will pass through the membrane. Nanofiltration membranes typically have micropores or openings between chains in a swollen polymer network. Molecular weight cut-offs for non-ionized molecules are typically in the range from 100-20,000 Daltons. For ions of the same molecular weight, membrane rejections (retentions) will increase progressively for ionic charges of 0, 1, 2, 3 etc. for a particular membrane because of increasing charge density (see, e.g., Eriksson, P., "Nanofiltration Extends the Range of Membrane Filtration," *Environmental Progress*, 7: 58-59 (1988)). Nanofiltration is also described in *Chemical Engineering Progress*, pp. 68-74 (March 1994), Rautenbach et al., *Desalination* 77: 73 (1990), and U.S. Pat. No. 4,806,244). In a typical application, nucleotide sugars of interest will be retained by the nanofiltration membrane and contaminating salts and other undesired components will pass through. A nanofiltration membrane useful in the methods of the invention will typically have a retention characteristic for the nucleotide sugar of interest of from about 40% to about 100%, preferably from about 70% to about 100%, more preferably from about 90% to about 100%. The nanofilter membranes used in the invention can be any one of the conventional nanofilter membranes, with polyamide membranes being particularly suitable. Several commercial manufacturers, including Millipore Corp. (Bedford, Mass.), Osmonics, Inc. (Minnetonka, Minn.), Filmtec, UOP, Advanced Membrane Technologies, Desalination Systems, and Nitto, among others, distribute nanofiltration membranes that are suitable for use in the methods of the invention. For example, suitable membranes include the Osmonics MX07, YK, GH (G-10), GE (G-5), and HL membranes, among others.

Reverse osmosis (RO) membranes also allow a variety of aqueous solutes to pass through them while retaining selected molecules. Generally, osmosis refers to a process whereby a pure liquid (usually water) passes through a semipermeable membrane into a solution (usually sugar or salt and water) to dilute the solution and achieve osmotic equilibrium between the two liquids. In contrast, reverse osmosis is a pressure driven membrane process wherein the application of external pressure to the membrane system results in a reverse flux with the water molecules passing from a saline or sugar solution compartment into the pure water compartment of the membrane system. A RO membrane, which is semipermeable and non-porous, requires an aqueous feed to be pumped to it at a pressure above the osmotic pressure of the substances dissolved in the water. An RO membrane can effectively remove low molecular weight molecules (<200 Daltons) and also ions from water. Preferably, the reverse osmosis membrane will have a retention characteristic for the nucleotide sugar of interest of from about 40% to about 100%, preferably from about 70% to about 100%, and more preferably from about 90% to about 100%. Suitable RO membranes include, but are not limited to, the Filmtec BW-30, Filmtec SW-30, Filmtec SW-30HR, UOP RO membranes, Desal RO membranes, Osmonics RO membranes, Advanced Membrane Technologies RO membranes, and the Nitto RO membranes, among others. One example of a suitable RO membrane is Millipore Cat. No. CDRN500 60 (Millipore Corp., Bedford Mass.).

The membranes used in the invention may be employed in any of the known membrane constructions. For example, the membranes can be flat, plate and frame, tubular, spiral wound, hollow fiber, and the like. In a preferred embodiment, the membrane is spiral wound. The membranes can be employed in any suitable configuration, including either a cross-flow or a depth configuration. In "cross-flow" filtration, which is preferred for ultrafiltration, nanofiltration and reverse osmosis purifications according to the invention, the "feed" or solution from which the carbohydrate of interest is to be purified flows through membrane channels, either parallel or tangential to the membrane surface, and is separated into a retentate (also called recycle or concentrate) stream and a permeate stream. To maintain an efficient membrane, the feed stream should flow, at a sufficiently high velocity, parallel to the membrane surface to create shear forces and/or turbulence to sweep away accumulating particles rejected by the membrane. Cross-flow filtration thus entails the flow of three streams—feed, permeate and retentate. In contrast, a "dead end" or "depth" filter has only two streams—feed and filtrate (or permeate). The recycle or retentate stream, which retains all the particles and large molecules rejected by the membrane, can be entirely recycled to the membrane module in which the recycle stream is generated, or can be partially removed from the system. When the methods of the invention are used to purify nucleotide sugars from lower molecular weight components, for example, the desired nucleotide sugars are contained in the retentate stream (or feed stream, for a depth filter), while the permeate stream contains the removed contaminants.

The purification methods of the invention can be further optimized by adjusting the pressure, flow rate, and temperature at which the filtration is carried out. UF, NF, and RO generally require increasing pressures above ambient to overcome the osmotic pressure of the solution being passed through the membrane. The membrane manufacturers' instructions as to maximum and recommended operating pressures can be followed, with further optimization possible by making incremental adjustments. For example, the recommended pressure for UF will generally be between about 25 and about 100 psi, for NF between about 50 psi and about 1500 psi, and for RO between about 100 and about 1500 psi. Flow rates of both the concentrate (feed solution) and the permeate can also be adjusted to optimize the desired purification. Again, the manufacturers' recommendations for a particular membrane serve as a starting point from which to begin the optimization process by making incremental adjustments. Typical flow rates for the concentrate ($P_c$) will be between about 1 and about 15 gallons per minute (GPM), and more preferably between about 3 and about 7 GPM. For the permeate, flow rates ($P_f$) of between about 0.05 GPM and about 10 GPM are typical, with flow rates between about 0.2 and about 1 GPM being preferred. The temperature at which the purification is carried out can also influence the efficiency and speed of the purification. Temperatures of between about 0 and about 100° C. are typical, with temperatures between about 20 and 40° C. being preferred for most applications. Higher temperatures can, for some membranes, result in an increase in membrane pore size, thus providing an additional parameter that one can adjust to optimize a purification.

In a preferred embodiment, the filtration is performed in a membrane purification machine which provides a means for automating control of flow rate, pressure, temperature, and other parameters that can affect purification. For example, the Osmonics 213T membrane purification machine is suitable for use in the methods of the invention, as are machines manufactured by other companies listed above.

The membranes can be readily cleaned either after use or after the permeability of the membrane diminishes. Cleaning can be effected at a slightly elevated temperature if so desired, by rinsing with water or a caustic solution. If the streams contain small amounts of enzyme, rinsing in the presence of small amounts of surfactant, for instance ULTRASIL, is useful. Also, one can use prefilters (100-200 μm) to protect the more expensive nanofiltration membranes. Other cleaning agents can, if desired, be used. The choice of cleaning method will depend on the membrane being cleaned, and the membrane manufacturer's instructions should be consulted. The cleaning can be accomplished with a forward flushing or a backward flushing.

The purification methods of the invention can be used alone or in combination with other methods for purifying carbohydrates. For example, an ion exchange resin can be used to remove particular ions from a mixture containing a nucleotide sugar of interest, either before or after nanofiltration/reverse osmosis, or both before and after filtration. Ion exchange is particularly desirable if it is desired to remove ions such as phosphate and nucleotides that remain after a first round of nanofiltration or reverse osmosis. In the case of sialyl lactose synthesis as discussed above, this can be accomplished, for example, by adding an anion exchange resin such as AG1X-8 (acetate form, BioRad; see, e.g., BioRad catalog for other ion exchange resins) to a retentate that is at about pH 3 or lower until the phosphate concentration is reduced as desired. In this process, acetic acid is released, so one may wish to follow the ion exchange with an additional purification through the nanofiltration or reverse osmosis system. For example, one can circulate the pH 3 or lower solution through an Osmonics MX07 or similar membrane until the conductivity of the permeate is low and stabilized. The pH of the solution can then be raised to about 7, e.g., 7.4, with NaOH and the solution recirculated through the same membrane to remove remaining sodium acetate and salt. Cations can be removed in a similar manner; for example, to remove $Mn^{2+}$, an acidic ion exchange resin can be used, such as AG50WX8 ($H^+$) (Bio-Rad).

Filtration

In one embodiment, following synthesis, a nucleotide sugar solution is optionally clarified by filtration. The nucleotide sugar solution passes through a membrane filter (e.g., a bag filter) in which contaminating salts and other undesired contaminants are filtered out of the nucleotide sugar solution. The clarification step can be incorporated at any step of the process. In a preferred embodiment, the nucleotide sugar solution is clarified after synthesis of the nucleotide sugar. The nucleotide sugar solution may be clarified one or more times.

In one example, the nucleotide sugar solution is purified using hollow fiber filtration. Hollow fiber filtration removes, e.g., proteins introduced by the enzyme preparation of the nucleotide sugar. The hollow fiber membrane retains proteins from the enzyme preparation while allowing for passage of the nucleotide sugar solution through the membrane. In an exemplary embodiment, the hollow fiber membrane comprises a hollow fiber membrane with a tangential filtration skid. The hollow fiber filtration step can be incorporated at any step of the process. In one embodiment, the nucleotide sugar solution goes through hollow fiber filtration after clarification. In another embodiment, the nucleotide sugar solution goes through hollow fiber filtration after synthesis of the nucleotide sugar. The nucleotide sugar solution may be filtered one or more times using hollow fiber filtration.

In another embodiment, the nucleotide sugar solution is purified using nanofiltration. Nanofiltration removes salts and other low molecular weight components from a mixture. Nanofiltration membranes separate molecules based on molecular weight and ionic charge. Molecular weight-cut-offs for non-ionized molecules are typically in the range from 100-20,000 daltons. In an exemplary application, saccharides of interest will be retained by the nanofiltration membrane and contaminating salts and other undesired components will pass through. The nanofiltration step can be incorporated at any step of the process. In one embodiment, the nucleotide sugar solution goes through hollow-fiber filtration first and then nanofiltration. In another embodiment, the nucleotide sugar solution goes through nanofiltration first and then hollow fiber filtration. In the alternative, the nucleotide sugar solution may be purified using either hollow-fiber filtration or nanofiltration. In another embodiment, the nucleotide sugar solution goes through nanofiltration after clarification. In yet another embodiment, the nucleotide sugar solution goes through nanofiltration after synthesis of the nucleotide sugar. The nucleotide sugar solution may be filtered one or more times using nanofiltration. After nanofiltration, the purified nucleotide sugar solution may generally be stored or may undergo further purification.

In another embodiment, the nucleotide sugar solution may optionally be decolorized (e.g., by passing the solution over activate carbon). In a preferred embodiment, decolorization involves passing the nucleotide sugar solution over a prepacked column of activated carbon attached to a chromatography system. Decolorization can be incorporated at any step of the process. In one embodiment, the nucleotide sugar solution is decolorized after nanofiltration. In another embodiment, the nucleotide sugar solution is decolorized after hollow-fiber filtration. In yet another embodiment, the nucleotide sugar solution is decolorized after clarification. The nucleotide sugar solution may be decolorized one or more times.

In another embodiment, the nucleotide sugar solution is purified using a charged depth media filter. The charged depth media filter removes, e.g., endotoxins from the nucleotide sugar solution. Endotoxins are toxic, natural compounds such as lipopolysaccharides found inside pathogens on the outer cell wall of bacteria. Purification by a charged depth media filter can be incorporated at any step of the process. In one embodiment, the nucleotide sugar solution is filtered after decolorization. In another embodiment, the nucleotide sugar solution is purified by a charged depth media filter after nanofiltration. In yet another embodiment, the nucleotide sugar solution is purified by a charged depth media filter after hollow-fiber filtration. In another embodiment, the nucleotide sugar solution is purified by a charged depth media filter after clarification. In another embodiment, the nucleotide sugar solution is purified by a charged depth media filter after synthesis of the nucleotide sugar. The nucleotide sugar solution may be filtered one or more times using a charged depth media filter.

In another embodiment, the nucleotide sugar solution is purified using a sterile filter. The sterile filter removes contaminating salts and other undesired contaminants from the nucleotide sugar solution. In a more preferred embodiment, the sterile filter is pre-packaged and sterilized with a bag manifold system for final filtration and storage. Purification by a sterile filter can be incorporated at any step of the process. In one embodiment, the nucleotide sugar solution is filtered by a sterile filter after purification by a charged depth media filter. In another embodiment, the nucleotide sugar solution is purified by a sterile filter after decolorization. In yet another embodiment, the nucleotide sugar solution is purified by a sterile filter after nanofiltration. In another embodiment, the nucleotide sugar solution is purified by a sterile filter after hollow fiber filtration. In another embodiment, the nucleotide sugar solution is purified by a sterile filter after clarification. In another embodiment, the nucleotide sugar solution is purified by a sterile filter after synthesis of the nucleotide sugar. The nucleotide sugar solution may be filtered one or more times using a sterile filter.

The following examples are offered solely for the purposes of illustration, and are intended neither to limit nor to define the invention. The following examples describe processes for the production of CMP-SA-PEGs. This focus is for clarity of illustration and should not be construed as limiting the process. A person of skill in the art will appreciate that the described processes equally apply to modified nucleotide sugars that include nucleotides and sugar moieties other than CMP and sialic acid, respectively.

EXAMPLES

General

Previous manufacturing processes for the production of CMP-SA-PEGs (e.g., CMP-SA-PEG-10 kDa, CMP-SA-PEG-20 kDa and CMP-SA-glycerol-PEG-40 kDa) utilized reversed phase chromatography (e.g., C-4 resins). An exemplary known process includes base hydrolysis, followed by TFF, followed by pH neutralization, followed by reverse-phase chromatography, followed by desalting, followed by removal of solvent (e.g., rotary evaporation) and freeze drying. This process was found to be non-suitable for large-scale applications (production of kg quantities) largely due to limitations associated with the reverse-phase chromatography step (e.g., high cost of the resin, the availability of prepacked commercial-scale C-4 columns, requirement to use of organic solvents) as well as the inability of this approach to completely separate all reaction contaminants. An alternative, streamlined production process was therefore developed to address the above destribed drawbacks and, particularly, to reduce the number of unit operations.

An exemplary improved process is depicted in FIG. 1. In one embodiment, the improved process incorporates only five unit operations. These include the coupling (PEGylation) reaction to form CMP-SA-PEG, rotary evaporation to essentially remove THF, anion exchange chromatography (purification step), desalting/concentration/diafiltration using TFF, and freeze-drying to form a solid product. Each step, except for freeze-drying, was optimized to improve performance of the process, which provides CMP-SA-PEGs in high purity.

The conversion yields for the coupling reaction ranged from 67-99% depending on the size of the PEG. The step yield for the AEX chromatography ranged from 95-99% and the TFF step from 90-95% and essentially removes all contaminants originating from the coupling reaction, including SA-PEG. Overall product recoveries for the combined reaction, rotoevaporation, ion-exchange, TFF and freeze-drying unit operations were between about 65 and 77%. The CMP-SA-PEGs produced by the new process had purities of between about 90 and 95%. $^1$H-NMR analyses of the final products showed no evidence of SA-PEG impurities. ICP analysis indicated the product was in the disodium salt form and contained no additional sodium salts.

Methods and Materials

Q Sepharose Big Beads were obtained from GE Healthcare. CMP-SA-Glycine Sodium salt ws obtained from AMRI. 10 kDa mPEG-p-nitrophenyl carbonate was obtained from (Dow Chemical Company. 40 kDa mPEG-p-nitrophenyl carbonate was obtained from NOF.

The following equipment was generally used: Peristaltic Pump (Cole-Palmer, Masterflex L/S digital standard drive, easy-load II pump head); Peristaltic Pump (Cole-Palmer, Masterflex console drive, easy-load I pump head); FPLC (GE Healthcare, AKTA FPLC); HPLC Pump A and B (Dynamax, SD-1); HPLC Detector (Dynamax, UV-C); HPLC Detector (Varian, ProStar model 340); ELS Detector (S.E.D.E.R.E. France, Sedex 55), Freeze Drier (VirTis, 6K Benchtop); Ion-Exchange Column (4 L) (Sepracor SA, 285530, 180×300 mm); Ion-Exchange Column (12 mL) (Biovalve, Inc., Omnifit, 006CC-10-50-AF, 10×250 mm); Ion-Exchange Column (2 L) (GE Healthcare, BPG 100/500 column, 18-1103-01); Ion-Exchange Column (100 mL) (GE Healthcare, XK 26/40, 18-8768-01); Conductivity Meter (Fisher Thermo Electron Corporation, Accumet Basic AB30, Orion 4 star); pH Meter (Orion Model 250A0; Positive displacement pump (Teknoflow Inc., Labtop (300/350)); Pellicon 2 Standard 1K Membrane, regenerated cellulose (Millipore, P2PLACV01; 1 kDa Regenerated Cellulose membrane; 0.1 m$^2$; V screen); Pellicon 2 Standard 3K Membrane, regenerated cellulose (Millipore, P2PLBCV01; 3 kDa Regenerated Cellulose membrane; 0.1 m$^2$; V screen); Pellicon 2 Standard 5K Membrane, regenerated cellulose (Millipore, P2C005C01; 5 kDa Regenerated Cellulose membrane; 0.1 m$^2$; C screen); Pellicon 2 Standard 1K Membrane, regenerated cellulose (Millipore, P2PLACC01; 1 kDa Regenerated Cellulose membrane; 0.1 m$^2$; C screen); Pellicon 2 Standard 1K Membrane, regenerated cellulose (Millipore, P2PLACV05; 1 kDa Regenerated Cellulose membrane; 0.5 m$^2$; V screen).

NWP=normalized water permeability; GSC=CMP-SA-Glycine; PSC=CMP-SA-PEG-20 kDa $^1$H-NMR (500 MHz, 800 MHz) spectra were recorded in D$_2$O. Chemical shifts are expressed in parts per million relative to the water peak.

Mixtures containing CMP-SA-PEGs were analyzed using reverse-phase HPLC (e.g., purity and recovery determinations). An exemplary method is described in the following: A Chromolith Performance RP18 column (VWR or Phenomonex) was attached to a Beckman HPLC system. Samples were injected via autosampler (10° C.) onto the column maintained at 35° C. The column was eluted at a flow rate of 5.0 mL/min, under the following gradient conditions (Eluent A: 20 mM Potassium Phosphate, 1 mM TABHS, pH=6.2; Eluent B: 100% acetonitrile): 0.5% B for 2 minutes, followed by a series of linear gradients to 20% B over 2 minutes and to 40% B over 8 minutes and a final isocratic elution at 40% B for 7 minutes. The column was re-equilibrated at 0.5% B for 3 minutes providing a total analysis time of 22 minutes. Eluted peaks were detected at 271 nm. GSC and CMP-SA-PEG-10 kDa (AMRI) were used as retention time and calibration standards. GSC standards (AMRI) were used to determine a standard curve, for calculating concentrations of CMP-SA-PEG-10 kDa. The purity of these standards was determined by quantitative NMR analysis.

The sodium content of purified and desalted CMP-SA-PEG samples was determined by inductively coupled plasma analysis (ICP).

Example 1

Preparation of CMP-SA-PEGs 1.1. Preparation of CMP-SA-PEGs-10 kDa

Cytidine-5'-monophospho-N-glycylsialic acid (CMP-SA-Glycine) disodium salt (1.23 g, 73.5 wt % pure, 1.34 mmol) was dissolved in Milli Q water (80 mL) in a 1 L single neck round bottom flask. The pH of the colorless solution was 10.48. Anhydrous THF was added (320 mL) and the pH adjusted to 8.6 by the dropwise addition of 5.5 mL of 500 mM monosodium phosphate solution (pH 4.6). The 10 kDa mPEG-p-nitrophenyl carbonate (20 g, 2.0 mmol, 1.5 eq.) was then added in one portion to the reaction solution. After the PEG reagent had dissolved, the pH of the solution was 8.7. The yellow solution was stirred at 20° C. for 21 hrs. The pH of the reaction mixture was then adjusted from 7.8 to 8.5 by addition of 0.1 M NaOH (4.0 mL). The reaction mixture was stirred an additional 3 hours and the THF removed by evaporation under reduced pressure at 30° C. using a rotary evaporator. The evaporation was stopped when the volume of the collected liquid was greater than 320 mL. The resulting yellow solution was diluted with Milli Q water (400 mL) and the solution filtered through a 0.22 micron 1 L Nalgene filter unit using a vacuum to remove any insoluble material. The final volume of the yellow filtrate was 684 mL and had a conductivity of 0.97 mS/cm. The conversion yield as determined by HPLC was 82% (Table 1, batch 9).

1.2. Preparation of CMP-SA-PEG-20 kDa

Cytidine-5'-monophospho-N-glycylsialic acid (CMP-SA-Glycine) disodium salt (0.61 g, 73.5 wt %, 0.656 mmol) was dissolved in Milli Q water (40 mL) in a 500 mL single neck round bottom flask. The pH of the colorless solution was 10.5. Anhydrous THF (160 mL) was added to the stirred solution and the pH adjusted to 8.5 (from 11.2) by the dropwise addition of 2.0 mL of 500 mM monosodium phosphate solution (pH 4.6). The 20 kDa mPEG-p-nitrophenyl carbonate (20.0 g, 1.0 mmol, 1.5 eq.) was added in one portion to the reaction solution. After the PEG had dissolved, the pH of the solution was 8.6. The yellow mixture was stirred at 20° C. for 21 hours. The pH of the reaction mixture was adjusted with NaOH (1.0 N, 2.0 mL) to 8.5 and the reaction mixture stirred for an additional 18 hours. The THF was removed by rotary evaporation using reduced pressure at 35° C. in a rotary evaporator. The evaporation was stopped when the volume of the collected liquid was more than 160 mL. The resulting yellow solution was diluted with Milli Q water (300 mL) and the solution filtered through a 0.22 micron 1 L Nalgene filter unit using vacuum to remove any insoluble material. The final volume of the yellow solution was 476 mL and had a conductivity of 0.725 mS/cm at pH 7.21. The conversion yield as determined by HPLC was 87% (Table 5, example 2).

1.3. Preparation of CMP-SA-glycerol-PEG-40 kDa

Cytidine-5'-monophospho-N-glycylsialic acid (CMP-SA-Glycine) disodium salt (368 mg, 73.5 wt % pure, 0.40 mmol) was dissolved in 40 mL of Milli Q water in a 500 mL single neck round bottom flask. Anhydrous THF (160 mL) was added to the stirred solution. The pH of the mixture was carefully adjusted from 11.5 to 8.6 by dropwise addition of 2.0 mL of 500 mM monosodium phosphate solution (pH 4.6). The 40 kDa mPEG-p-nitrophenyl carbonate (20.96 g, 90% activation, 0.44 mmol, 1.1 eq.) was added to the reaction mixture in one portion. After 20 hours, the pH of the reaction mixture was adjusted from 8.31 to 8.82 by the addition of 1.4 mL of 0.1N NaOH solution. After an additional 22 hours, about 0.8 mL of 0.1N NaOH was added to bring the pH of the mixture from 8.52 to 8.89. After another 24 hours (66 hours total reaction time), the THF was removed using a rotary evaporator under reduced pressure using a water bath temperature below 35° C. The evaporation was stopped when the volume of the collected liquid was more than 160 mL. The resulting yellow solution was diluted with 600 mL of Milli Q water and filtered through a 0.22 micron 1 L Nalgene filter with a vacuum pump. The filter was rinsed with about 50 mL Milli Q water. The final volume of the yellow filtrate solution was 678 mL and had a conductivity of 0.40 mS/cm with a pH of 7.25. The conversion yield was 57% by HPLC (Table 6, example 5). The reaction mixture was split into two equal portions of 335 mL. One portion was purified as described below.

Example 2

Anion Exchange Chromatography of CMP-SA-PEGs 2.1. Column Packing Procedure for Q-sepharose Big Bead Resin (2 L Scale)

Columns were prepared according to manufacturer's instructions. A representative procedure is described below:

An empty GE BPG 100/500 chromatography column was inspected for cleanliness and structural integrity. The bottom frit was wetted with water. The column outlet was plugged and 1-2 cm of the water was poured in the bottom of the column. Q-Sepharose Big Beads resin slurry in 20% ethanol (about 3.2 L, 65%) was resuspended to assure homogeneity. The resin slurry was poured slowly down the inside of the column to prevent air entrapment. After the resin slurry had been transferred to the column, the inside of the column was rinse using a squirt bottle containing 20% ethanol. The resin was allowed to settle for about 30 minutes, making sure that the height of the resin was about 3-5 cm higher than the desired height of 25 cm. (Add more resin if necessary). The flow adaptor was filled with water and placed into the column. Care was taken to insure that no air was trapped between the flow adaptor and the liquid. The column outlet was opened and the flow adaptor was adjusted down to rest gently on the bed. The inlet was connected to the Dynamax SD-1 HPLC pump. The pump was started and slowly ramped up to the target flow rate of 200 mL/min. (The flow rate can be ramped up in several incremental changes with hold up time of 2 min). After the bed was fully consolidated, the pump was shut off. The flow adaptor was adjusted down onto the bed until resistance was such that the adaptor would go no further. The column outlet was closed. The height of the resin was marked (25.4 cm). Ready for use, the column was first washed with 4 L of degassed RO water to remove the 20% ethanol from the resin slurry. It was charged with NaOH (2 CV, at 100 mL/min, 40 min residence time) to sanitize the column and generate the hydroxide form of the resin, washed with RO water (2 CV, at 200 mL/min) and then charged with 1 M sodium bicarbonate (3 CV, 200 mL/min) to generate the bicarbonate counterion form as described above.

2.2. Q-Sepharose Big Beads Purification of CMP-SA-PEG-10 kDa

In a BPG 100/500 column, 2.0 L of Q-Sepharose Big Beads anion exchange resin (chloride form; 10 cm ID×26 cm) was packed as described above and connected to a Dynamax SD-1 HPLC system equipped with a UV detector capable of reading at both 214 and 271 nm. The column was washed with 2 CV (4 L) degassed water at 100 mL/min (76 cm/hr) to remove the 20% ethanol packing solution. The column was then sanitized by washing with 1 M NaOH (2 CV, 4 L, 100 mL/min, 76 cm/hr) and then converted to the bicarbonate salt form by then washing with RO water (2 CV, 4 L, 200 mL/min, 130 cm/hr) followed by 1 M NaHCO$_3$ (3 CV, 6 L, 200 mL/min, 130 cm/hr) and finally with RO water (3 CV, 6 L, 200 mL/min, 130 cm/hr). The conductivity of the column effluent was ≤10 microS/cm (pH 4.5-6) when completed.

Figure 4:
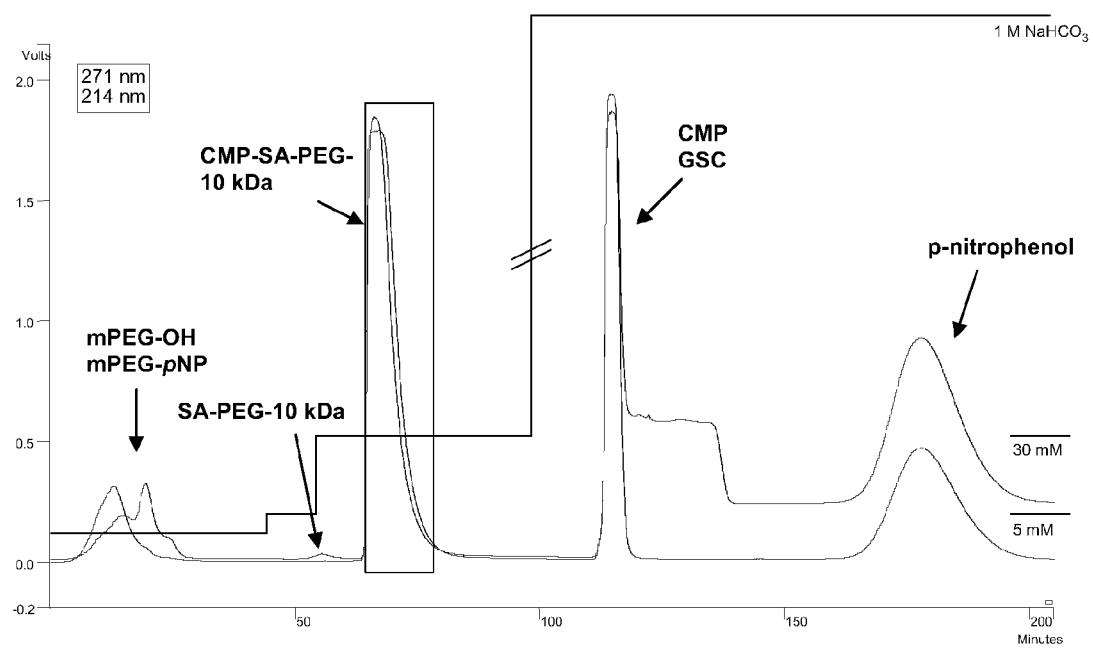
FIG. 4 is an anion exchange chromatogram obtained during the purification of CMP-SA-PEG-10 kDa using a Q Sepharose Big Beads chromatography column and a stepwise sodium bicarbonate elution protocol as described in Example 2.2 (5 mM NaHCO$_3$ for 0.6 CV; 30 mM for 3 CV; and 1 M for 7 CV). The retention times were: SA-PEG-10 kDa (55 min); CMP-SA-PEG-10 kDa (63 min); CMP and CMP-SA-Gly (GSC, 110 min) and p-nitrophenol (180 min).

The aqueous CMP-SA-PEG-10 kDa reaction mixture according to Example 1.1 (684 mL, pH 7.27, conductivity 0.97 mS/cm) was loaded onto the column at a flow rate of 65 mL/min (50 cm/hr). After loading was complete, the column was washed with 4 L (2 CV) of RO water at a flow rate of 130 mL/min (100 cm/hr) until all the non-binding impurities had been washed from the column and the UV signal (271 and 214 nm) returned to baseline. A step elution was used to obtain the product. The SA-PEG impurity was eluted first (55 min retention time) from the column using 1.2 L (0.6 CV) of 5 mM NaHCO$_3$ at a flow rate of 130 mL/min (100 cm/hr) as shown in FIG. 4. The elution buffer concentration was then increased and the product eluted (63 min retention time) with 6 L (3 CV) of 30 mM NaHCO$_3$ at a flow rate of 100 cm/hr. The excess CMP-SA-Glycine and other reaction by-products were then eluted from the column using 14 L (7 CV) of 1 M NaHCO$_3$ prior to column regeneration. Column elution was monitored using UV at both 214 nm and 271 nm and the appropriate fractions collected manually (FIG. 4). The product fraction started when the UV 271 reading rose above the base line following the elution of the SA-PEG impurity peak, and ended at about 5% of the peak maximum at the trailing side of the product peak. The product-containing fraction (fraction 1, 2.0 L) was split into two portions. About 500 mL was used to optimize the Tangential Flow Filtration (TFF) step while the remaining 1.5 L was processed by the optimized TFF procedure as described below.

2.3. Q-Sepharose Big Beads Purification of CMP-SA-PEG-20 kDa

In a BPG 100/500 column, 2.0 L of Q-Sepharose Big Beads anion exchange resin (chloride form; 10 cm ID×26 cm) was packed as described above and connected to a Dynamax SD-1 HPLC system equipped with a UV detector capable of reading at both 214 and 271 nm. The column was washed with 2 CV (4 L) degassed water at 100 mL/min (76 cm/hr) to remove the 20% ethanol packing solution. The column was then sanitized by washing with 1 M NaOH (2 CV, 4 L, 100 mL/min, 76 cm/hr) and then converted to the bicarbonate form by then washing with RO water (2 CV, 4 L, 200 mL/min, 153 cm/hr) followed by 1 M NaHCO$_3$ (3 CV, 6 L, 200 mL/min, 153 cm/hr) and RO water (3 CV, 6 L, 200 mL/min, 153 cm/hr). The conductivity of the column effluent was ≤10 microS/cm (pH 4.5-6) when completed.

Figure 6:
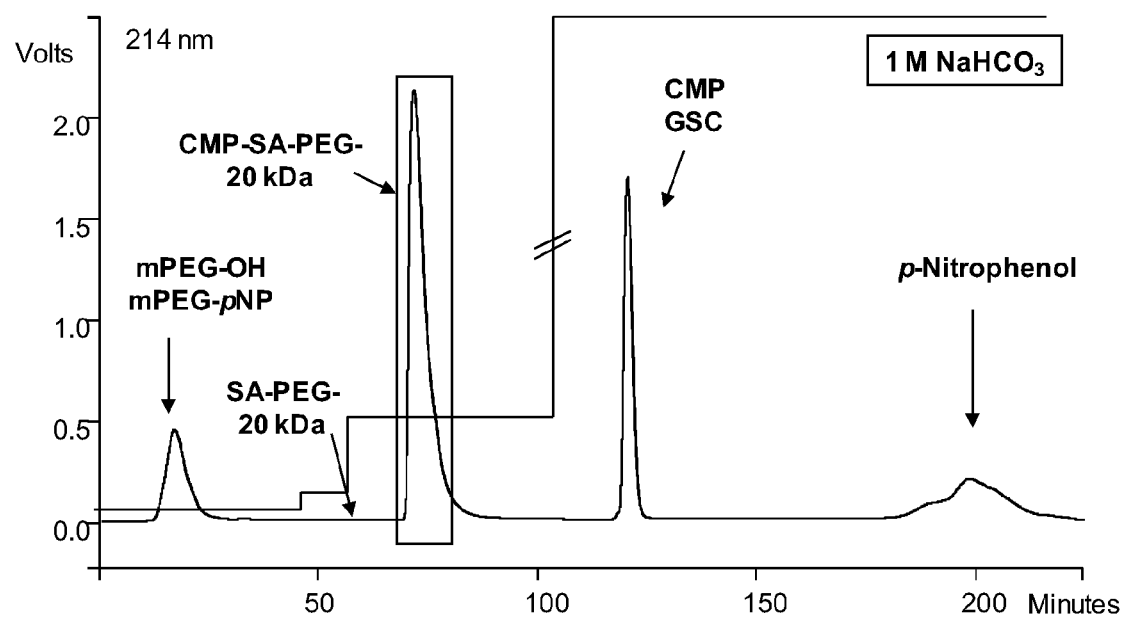
FIG. 6 is an anion exchange chromatogram obtained during the purification of CMP-SA-PEG-20 kDa using a Q Sepharose Big Beads chromatography column and a sodium bicarbonate stepwise elution protocol as described in Example 2.3 (2 mM NaHCO$_3$ for 1 CV; 30 mM for 3 CV; and 1 M for 7 CV). The retention times were: SA-PEG-20 kDa (55 min); CMP-SA-PEG-20 kDa (75 min); CMP and CMP-SA-Gly (120 min) and p-nitrophenol (200 min).

CMP-SA-PEG-20 kDa reaction mixture according to Example 1.2 (476 mL, pH 7.21, conductivity 0.725 mS/cm) was loaded onto the prepared column at a flow rate of 65 mL/min (50 cm/hr). After loading was complete, the column was washed with 4 L (2 CV) of RO water at a flow rate of 130 mL/min (100 cm/hr) until all of the non-binding impurities had been washed from the column and the UV signal (217 and 271 nm) returned to baseline. The product was eluted using a step elution. The SA-PEG impurity was eluted first (55 min retention time) from the column using 2.0 L (1.0 CV) of 2 mM NaHCO$_3$ at a flow rate of 130 mL/min (100 cm/hr) as shown in FIG. 6. The elution buffer concentration was then increased and the product eluted (75 min retention time) with 6 L (3 CV) of 30 mM NaHCO$_3$ at a flow rate of 130 mL/min (100 cm/hr). The excess CMP-SA-Glycine and other reaction by-products were then eluted from the column using 14 L (7 CV) of 1 M NaHCO$_3$ prior to column regeneration. Column elution was monitored by UV absorption at both 214 nm and 271 nm and the appropriate fractions collected (FIG. 6). The product fraction started when the UV271 reading rose above the base line following the elution of the SA-PEG impurity peak, and ended at about 5% of the peak maximum at the trailing side of the product peak. The product containing fraction (fraction 1, 2.0 L) was used for the next step.

2.4. Q-Sepharose Big Beads Purification of CMP-SA-glycerol-PEG-40 kDa

In a BPG 100/500 column, 2.0 L of Q-Sepharose Big Beads anion exchange resin (chloride form; 10 cm ID×25.5 cm) was packed as described above and connected to a Dynamax SD-1 HPLC system equipped with a UV detector capable of reading at both 214 and 271 nm. The column was washed with 2 CV (4 L) degassed water at 100 mL/min (76 cm/hr) to remove the 20% ethanol packing solution. The column was then sanitize by washing with 1 M NaOH (2 CV, 4 L, 100 mL/min, 76 cm/hr) and then converted to the bicarbonate form by then washing with RO water (2 CV, 4 L, 200 mL/min, 153 cm/hr) followed by 1 M NaHCO$_3$ (3 CV, 6 L, 200 mL/min, 153 cm/hr) and RO water (3 CV, 6 L, 200 mL/min, 153 cm/hr. The conductivity of the column effluent was ≤10 microS/cm (pH 4.5-6) when completed.

Figure 7:
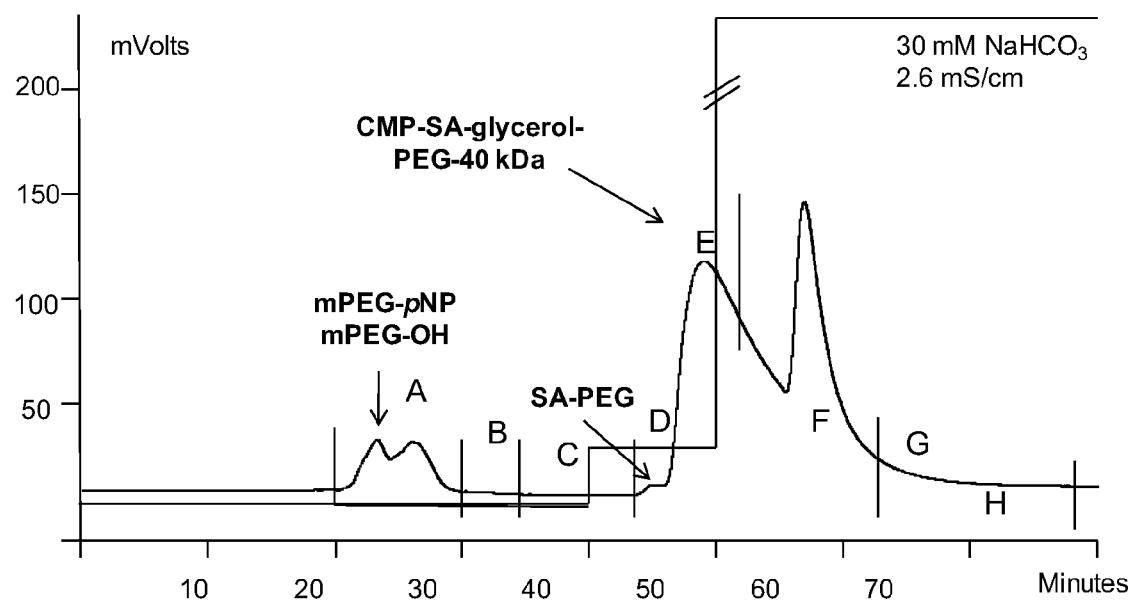
FIG. 7 is an anion exchange chromatogram obtained during the purification of CMP-SA-PEG-40 kDa using a Q Sepharose Big Beads chromatography column and a sodium bicarbonate stepwise elution elution protocol as described in Example 2.4 (2 mM for 1 CV and 30 mM for 3 CV).

The reaction mixture according to Example 1.3 (335 mL, pH 7.25, conductivity 0.40 mS/cm) was loaded onto the prepared column at a flow rate of 40 mL/min (30.6 cm/hr). After loading was complete, the container was rinsed with about 500 mL water, and the solution loaded onto the column. The column was then washed with 4 L (2 CV) of RO water at a flow rate of 200 mL/min (153 cm/hr) until all of the non-binding impurities had been washed from the column and the UV signal returned to baseline (217 and 271 nm). The product was eluted using a step elution. The SA-PEG impurity was eluted first (44 min retention time) from the column using 2.0 L (1.0 CV) of 2 mM NaHCO$_3$ at a flow rate of 200 mL/min (153 cm/hr) as shown in FIG. 7. The elution buffer concentration was then increased and the product eluted (47 min retention time) with 6 L (3 CV) of 20 mM NaHCO$_3$ at a flow rate of 200 mL/min (153 cm/hr). Column elution was monitored by UV absorption at both 214 nm and 271 nm and the appropriate fractions collected (FIG. 7). The product fraction started when the UV271 reading rose to 20% of the product peak max absorbance (allowing for removal of the SA-PEG impurity shoulder), and ended at about 5% of the peak maximum at the trailing side of the major product peak. The product containing fractions were pooled (4.05 L, pH=7.4, 1218 microS/cm) and used for the next step.

Example 3

Desalting Using Ultrafiltration 3.1. Tangential Flow Filtration of CMP-SA-glycerol-PEG-10 kDa Product Pool The 1.5 L Q Sepharose Big Beads product pool according to Example 2.2 was desalted by tangential flow filtration (TFF) using the process parameters summarized in Table 1, below. A Masterflex L/S peristaltic pump was connected with silicone tubing (L/S 24) to a Millipore Pellicon-2 Mini Holder equipped with three Millipore 1 kDa Pellicon 2 "MINI" filters (PLAC-V 1 kDa Regenerated Cellulose Membrane; Screen Type: V; 0.1 m$^2$). About 500 mL of the aqueous product solution was transferred to a 500 mL PETG bottle, which was immersed in an ice bath. The solution was stirred using a magnetic stir bar, and the temperature monitored and maintained at 14-16° C. throughout the process. Both the feed line and the retentate line were placed inside the PETG bottle on the TFF system. The remaining 1 L of solution, also chilled using an ice bath, was fed into the PETG bottle through another silicone tubing (L/S 25) using a second Masterflex peristaltic pump. The transfer flow rate of the second pump was set to equal the permeate flow rate of the TFF process in order to maintain a constant volume in the PETG bottle. The permeate solution was collected as fractions in a 250 mL graduated cylinder and each 250 mL of collected solution was transferred to storage bottles. The initial flow rate of the peristaltic pump was set at 1200 mL/min, and the retentate valve was adjusted to keep a constant TMP (~22 psi) throughout the process. The permeate solution was sampled every 250 mL volume, and the pH and conductivity were recorded. The permeate flow rate was also manually recorded. Once the original 1.5 L of product solution had been concentrated to a total volume of about 500 mL, chilled RO water was added into the PETG retentate bottle to maintain a constant volume. The permeate solution was continuously sampled every 500 mL. Once the volume of permeate had reached 2000 mL and the conductivity of the permeate solution dropped to 47 microS/cm, the transfer pump was stopped. The retentate solution was then transferred to another PETG bottle (1 L). RO water (150 mL) was then added to the retentate PETG bottle and re-circulated for 5 min through the TFF system. This removed the remaining product in the system. The original retentate solution and wash retentate solution were then combined. The overall TFF step recovery of the CMP-SA-PEG-10 kDa was 90% based on HPLC analysis (Table 2). The recombined retentate solution (488 mL, pH=7.31, 138 microS/cm) was freeze dried which provided 7.15 g (66% overall process yield) of a white solid that was 87% pure by the current analysis method (Table 3). The lyophilized product was analyzed by $^1$H NMR.

TABLE 1

Optimized Process Parameters for the Tangential Flow Filtration (TFF) Unit Operation for CMP-SA-PEG (10 and 20 kDa)

| | |
|---|---|
| Membrane | Three 0.1 m$^2$ Millipore 1K Pellicon 2 "MINI" filter (PLAC 1K Regenerated Cellulose Membrane, Type V Screen |
| Membrane area, m$^2$ | 0.3 |
| TMP | 22 ± 1 psig |
| Flux | 3.7 LMH |
| Retentate Volume (L) | 500 mL (after concentration and throughout the diafiltration) |
| Equilibration/Diafiltration Buffer | RO water |
| Diafiltration Criteria | 4 DF volumes (2000 mL total) |
| Total Processing Time | approximately 3 hours |
| Temperature (° C.) | ≤16° C. (preferably 4-8° C.) |
| Membrane Storage Conditions | 0.1 M NaOH or 20% ethanol |

TABLE 2

Experimental results for the Tangential Flow Filtration (TFF) Unit Operation for CMP-SA-PEGs (10 kDa and 20 kDa)

| PEG | Membrane Area (m$^2$) | NWP (L/hr/psig/m$^2$) | Retentate Volume (L) | Retentate Temp Initial/Final (° C.) | Retentate pH | Conductivity (mcS/cm) | Recovery (%) |
|---|---|---|---|---|---|---|---|
| 10 kDa | 0.1 | 0.20 | 0.15 | 21/23 | 6.6 | 112 | 96% |
| 10 kDa | 0.3 | 0.17 | 0.5 | 16/15 | 7.3 | 138 | 90% |
| 20 kDa | 0.3 | 0.17 | 0.5 | 14/16 | 7.8 | 110 | 112% |

In Table 2, the retentate volume was measured after concentration and desalting of the initial feed solution. The retentate temperature is the initial retentate temperature measured at the beginning of the concentration step and the final retentate temperature at the end of the diafiltration step. The retentate pH was measured after combination of first retentate (after concentration and diafiltration) with the system wash retentate. The conductivity of the retentate was measured after the combination of the first retentate (after concentration and diafiltration) and the system wash retentate. The overall product recovery was determined based on the total amount of product in the system feed solution compared to the amount of product in the final combined retentates (after concentration, diafiltration and system wash).

TABLE 3

Overall Process Recoveries for CMP-SA-PEG (10 kDa and 20 kDa)

| Process Batch | Dry Weight (g) | Purity (%) | Overall Recovery |
|---|---|---|---|
| CMP-SA-PEG-10 kDa | 2.53 | 85.9% | 70% |
| CMP-SA-PEG-10 kDa | 7.15 | 87.0% | 64% |
| CMP-SA-PEG-20 kDa | 10.52 | 95.7% | 77% |

In Table 3, the dry weight is the solid weight after freeze-drying. The purity was determined by dividing the amount of product in the freeze-dried product as determined by RP-HPLC by the total amount of solid in the freeze-dried sample (assumed as product mass of 10,600 Dalton for CMP-SA-PEG-10 kDa or 20,600 Dalton for CMP-SA-PEG-20 kDa). Overall Recoveries for the production process (the reaction, solvent evaporation, AEX purification, concentration/diafiltration and freeze-drying steps) were calculated based on the ratio of moles of product obtained divided by the moles of the limiting reagent (CMP-SA-Gly) used in the coupling reaction multiplied by the fraction of the product pool processed×100%.

3.2. Tangential Flow Filtration of CMP-SA-glycerol-PEG-20 kDa Product Pool

The Q Sepharose Big Beads product pool according to Example 2.3 (2.0 L) was desalted by tangential flow filtration using the process parameters summarized in Table 1, above. A Masterflex L/S peristaltic pump was connected with silicone tubing (L/S 24) to a Millipore Pellicon-2 Mini Holder equipped with three Millipore 1 kDa Pellicon 2 "MINI" filters (PLAC-V 1 kDa Regenerated Cellulose Membrane; Screen Type: V; 0.1 m$^2$). About 500 mL of the aqueous product solution was transferred to a 500 mL PETG bottle, which was immersed in an ice bath. The solution was stirred using a magnetic stir bar, and the temperature monitored and maintained at 4° C. throughout the process. Both the feed line and the retentate line were placed inside the PETG bottle on the TFF system. The remaining 1.5 L of solution, also chilled using an ice bath, was fed into the PETG bottle through another silicone tubing (L/S 25) using a second Masterflex peristaltic pump. The transfer flow rate of the second pump was set to equal the permeate flow rate of the TFF process in order to maintain a constant volume in the feed PETG bottle. The permeate solution was collected as 500 mL fractions using a 500 mL graduated cylinder and were transferred to storage bottles. The initial flow rate of the peristaltic pump was set at 1200 mL/min, then the retentate valve was adjusted to keep a constant TMP (~22 psi) throughout the process. During processing, the permeate solution was sampled after every 500 mL collection, and the pH and conductivity were recorded. The permeate flow rate was also manually recorded. Once the original volume of product solution in the feed (2.0 L) had been concentrated to a total volume of about 500 mL, the retentate solution was then diafiltered. Chilled RO water (4° C.) was added into the PETG retentate bottle connected to the TFF system at a rate to maintain a constant volume during diafiltration. The permeate solution was continuously sampled every 500 mL and the conductivity and pH recorded. Once the volume of permeate had reached ~2000 mL and the conductivity of the permeate solution dropped to 56 microS/cm, the transfer pump was stopped. The retentate solution was then transferred to another PETG bottle (1 L). RO water (150 mL) was added to the feed PETG bottle and re-circulated through the TFF system for 5 min. The original retentate solution and the wash retentate solution were then combined. The overall TFF step recovery of the CMP-SA-PEG-20 kDa was 112% as determined by HPLC analysis (Table 3). The combined retentate solution (530 mL, pH=7.81, 110 microS/cm) was freeze dried to yield 10.52 g (77% overall processs yield) as a white solid that was 96% pure by the current analysis method (Table 3). The lyophilized product was analyzed by $^1$H-NMR.

3.3. Tangential Flow Filtration of CMP-SA-glycerol-PEG-40 kDa Product Pool

The Q Sepharose Big Beads product pool according to Example 2.4 (4.05 L) was desalted by tangential flow filtration (TFF) using the process parameters summarized in Table 4, below. A Masterflex L/S peristaltic pump (TFF pump) was connected through silicone tubing (L/S 35) to a Millipore Pellicon-2 Holder equipped with two Millipore 1 kDa Pellicon 2 Regenerated Cellulose Membranes; Screen Type: V; 0.5 m$^2$. About 1 L of the aqueous product solution was transferred to a 1 L PETG bottle which was immersed in an ice bath. The solution was stirred with a magnetic stir bar, and the temperature was monitored through the entire process. The remaining product solution was chilled on an ice bath, and the solution fed into the PETG bottle through silicone tubing (L/S 25) by a second Masterflex peristaltic pump. The transfer speed of the second pump was set to equal to the permeate flow rate in order to maintain a constant volume in the PETG bottle. Both the feed line and the retentate line were placed inside the PETG bottle on the TFF system. The permeate solution was collected as 1.0 L fractions in a 1.0 L graduated cylinder and transferred to storage bottles. The initial flow rate of the TFF peristaltic pump was set at 2.4 L/min, and the retentate valve was adjusted to maintain a constant TMP (~20 psi) throughout the process. The permeate solution was sampled after each 1.0 L of solution collected, and the pH and conductivity were recorded. The permeate flow rate was also manually recorded. Once the original 4.0 L of product solution had been concentrated to a total volume of about 1.0 L, the retentate was diafiltered. Chilled RO water (4° C.) was added into the PETG retentate bottle at a rate to maintain a constant volume during diafiltration. The permeate solution was continuously sampled every 1.0 L. Once the total volume of the permeate solution had reached ~4.0 L and the conductivity of the permeate solution had dropped to 56 microS/cm, the transfer pump was stopped. The retentate solution was then transferred to another PETG bottle (2 L). RO water (350 mL) was added to the PETG retentate bottle and re-circulated in the TFF system for 5 min. The original retentate solution and the wash retentate solution were then combined. The overall TFF step recovery of the CMP-SA-glycerol-PEG-40 kDa was 93% based on HPLC analysis of the final retentate pool and the original ion exchange pool (Table 5, process #1). The final TFF product solution (1060 mL, pH 7.60, 66 microS/cm) was freeze-dried to afford 5.82 g (67% overall process yield) of a white solid with a purity of 92% by HPLC (Table 6, process 1). The freeze-dried product was analyzed by $^1$H-NMR.

TABLE 4

Process Parameters for the Tangential Flow Filtration (TFF) Unit Operation for CMP-SA-glycerol-PEG-40 kDa

| | |
|---|---|
| Membrane | Two 0.5 m$^2$ Millipore 1K Pellicon 2 Regenerated Cellulose Membrane, Type V Screen |
| Membrane area, m$^2$ | 1.0 |
| TMP | 20 ± 1 psig |
| Flux | 3 LMH |
| Retentate Volume (L) | 1 L (after concentration and throughout the diafiltration) |
| Equilibration/Diafiltration Buffer | RO water |
| Diafiltration Criteria | ≥3 DF volumes (3000 mL total) |
| Total Processing Time | Approximately 3 hours |
| Temperature (° C.) | ≤15° C. (optimal temperature of 4-8° C.) |
| CIP Conditions | 0.1 M NaOH, hold 30 minutes |
| Membrane Storage Condition | 0.01 M NaOH or 20% ethanol |

TABLE 5

Results of the Tangential flow filtration unit operation for CMP-SA-glycerol-PEG-40 kDa

|  | Membrane Area ($m^2$) | NWP L/hr/psig/$m^2$ | Retentate Volume (L) | Initial/Final Temp (° C.) | Retentate pH | Retentate Conductivity (mcS/cm) | Recovery |
| --- | --- | --- | --- | --- | --- | --- | --- |
| Batch 1 | 1.0 | 0.15 | 1 | 15-12 | 7.6 | 66 | 93% |
| Batch 2 | 1.0 | 0.15 | 1 | 13-10 | 7.0 | 45 | 86% |

In Table 5, the retentate volume was determined after concentration and desalting of the initial feed solution. The initial retentate temperature in the system was measured at the beginning of the concentration step. The final retentate temperature was determined at the end of the diafiltion step. The pH of the retentate was determined after combination of the first retentate (after concentration and diafiltration) with the system wash retentate. The conductivity of the retentate was measured after the combination of the first retentate (after concentration and diafiltration) and the system wash retentate. Product recovery was calculated from the ratio of the product in the final TFF retentate pool (RP-HPLC concentration×volume) to that of the starting IEX pool (RP-HPLC concentration×volume).

TABLE 6

Process Summary Results for the Production of CMP-SA-glycerol-PEG-40 kDa

|  | Dry Weight (g) | Amount (g) | Purity | Overall Recovery |
| --- | --- | --- | --- | --- |
| Batch 1 | 5.82 | 5.14 | 92.0% | 67% |
| Batch 2 | 5.36 | 4.81 | 93.1% | 62% |

In Table 6, product mass was calculated from the RP-HPLC concentration value and volume of the TFF retentate pool. The purity was determined using RP-HPLC and was calculated using the manufacturers (NOF) certificate of analysis mPEG molecular weight for the mass of CMP-SA-glycerol-PEG-40 kDa (43,347 Daltons). Overall Recoveries were calculated for the combined reaction, chromatography and TFF processes based on the ratio of moles of product obtained (from dry weight) divided by the moles of limiting reagent in the reaction multiplied by the fraction of the product pool processed×100%.

Example 4

Additional Desalting Experiments Using Ultrafiltration 4.1. Desalting of CMP-SA-glycerol-PEG-40 kDa using a 5 kDa Membrane.

A Masterflex L/S peristaltic pump was connected through silicone tubing (L/S 15, #96400-15) to a Millipore Pellicon-2 Mini Holder equipped with one Millipore 5 kDa Pellicon 2 "MINI" filter (PLCC 5 kDa Regenerated Cellulose Membrane; Screen Type: C, 0.1 $m^2$). The system was flushed with 2 L of water at 1000 mL/min. Water (2 L) was then re-circulated in the system at 1000 mL/min, and about 500 mL of permeate was collected with a TMP of 20 psi. The conductivity of the retentate was measured as 3 microS/cm. The normalized water permeability (NWP) was measured as ~1.4 L/hr/$m^2$/psi. The CMP-SA-glycerol-PEG-40 kDa (4.0 g) was dissolved in 200 mL of chilled Milli Q water in a 500 mL plastic bottle, which was immersed in an ice bath. The solution was stirred with a magnetic stir bar. Both the feed line and the retentate line were placed inside the bottle. The solution was re-circulated through the system for 5 min at 500 mL/min. The pump speed was then increased to 1000 mL/min and the retentate pressure adjusted to 13 psi which provided a feed pressure of 25 psi and TMP of 19 psi. The TMP was maintained constant through the process. The permeate was collected in 100 mL fractions, the corresponding time for each fraction and temperature of the retentate were recorded. A second peristaltic was used to transfer chilled milli Q water to maintain a constant volume in the retentate bottle. The dialysis step was completed when 600 mL of the permeate was collected. The conductivity of the final 100 mL fraction was 12 microS/cm. The temperature of the retentate was between 15-16° C. during the process. The average permeate flow rate was 28.6 mL/min with a calculated flux of 17.2 L/hr/$m^2$. The normalized permeate rate was 0.90 L/hr/$m^2$/psi. The retentate was transferred into a separate bottle, and the system was recirculated with 100 mL of water for 5 min. The original retentate solution and the wash retentate solution were then combined. The final combined retentate solutions (~350 mL, pH 6.6, 33 microS/cm) was freeze-dried to afford 3.92 g of a white solid with a recovery of 98% (Table 7).

4.2. Desalting of CMP-SA-glycerol-PEG-40 kDa using a 3 kDa Membrane.

A Masterflex L/S peristaltic pump was connected through silicone tubing (L/S 15, #96400-15) to a Millipore Pellicon-2 Mini Holder equipped with one Millipore 3 kDa Pellicon 2 "MINI" filter (PLCC 3 kDa Regenerated Cellulose Membrane; Screen Type: C, 0.1 $m^2$). The system was flushed with 2 L of water at 1000 mL/min. Then it was re-circulated with 2 L water at 1000 mL/min, and about 500 ml of permeate was collected with TMP at 20 psi. The conductivity of the retentate was measured as 5 microS/cm. The normalized water permeability (NWP) was measured as ~0.75 L/hr/$m^2$/psi. CMP-SA-glycerol-PEG-40 kDa (4.0 g) was dissolved in 200 mL of chilled Milli Q water in a 500 mL plastic bottle, which was immersed in an ice bath. The solution was stirred with a magnetic stir bar. Both the feed line and the retentate line were placed inside the bottle. The solution was recirculated through the system for 5 min at 500 mL/min. The pump speed was then increased to 1000 mL/min and the retentate pressure adjusted to 20 psi providing a feed pressure of 20 psi and a TMP of 20 psi. The TMP was maintained constant through the process. The permeate was collected in 100 mL fractions, the corresponding time for each fraction and temperature of the retentate were recorded. A second peristaltic was used to transfer chilled milli Q water to maintain a constant volume in the retentate bottle. The dialysis step was completed when 600 mL of the permeate was collected. The conductivity of the final 100 mL fraction was 34 microS/cm. The temperature of the retentate was between 13-15° C. during the process. The average permeate flow rate is 16.7 ml/min, and the calculated flux was 10.0 L/hr/$m^2$, and the normalized permeate rate was 0.50 L/hr/$m^2$/psi. The retentate was transferred into a separate bottle, and the system was re-circulated with 100 ml of water for 5 min. The original retentate solution and the wash retentate solution were then combined. The combined retentate solutions (~300 mL, pH 7.4, 56 microS/cm) was freeze-dried to afford 3.86 g of a white solid with a recovery of 95% (Table 7).

TABLE 7

Tangential Flow Filtration of CMP-SA-glycerol-PEG-40 kDa using Regenerated Cellulose Membranes (3 kDa and 5 kDa)

| Membrane Type | Membrane Area ($m^2$) | Retentate Initial Conc. (mg/mL) | TMP (psi) | Temp (° C.) | Permeate flux (L/hr/$m^2$) | NWP L/hr/$m^2$/psi | Conductivity (microS/cm) | Recovery |
|---|---|---|---|---|---|---|---|---|
| 5 kDa | 0.1 | 20 | 19 | 15-16 | 10.0 | 0.90 | 33 | 98% |
| 3 kDa | 0.1 | 20 | 20 | 13-15 | 7.6 | 0.50 | 56 | 95% |

In Table 7, the temperature is the retentate temperature range in the system throughout the diafiltration process. The conductivity was measured in the retentate after the combination of the first retentate (after diafiltration) and the system wash retentate. Product recovery was calculated from the ratio of the mass of the lyophilized TFF product to that of the CMP-SA-glycerol-PEG used to prepare the original solution for TFF (4 g).

Example 5

Optimization of the Coupling (PEGylation) Reaction

The coupling reaction used to form CMP-SA-PEG-10 kDa was optimized to improve conversion yields and simplify process manipulations during the reaction (Table 8). A slight molar excess of mPEG-pNP reagent (1.2-1.5 mole eq.) was required to obtain the highest conversion yields. The reactions were performed in THF/water (4/1) at CMP-SA-Glycine concentrations between 3.4-3.7 mM and mPEG-pNP concentrations between 50-55 mg/mL.

TABLE 8

Coupling-Reaction Results for CMP-SA-PEG-10 kDa

| Rkt No | 10-kDa-PEG-pNP (mmol) | GSC (mmol) | THF (mL) | Water (mL) | Buffer (mcL) | pH Range | Rkt Time (hrs) | Final Volume (mL) | PSC/GSC Ratio | Conc. CMP-SA-PEG (mg/mL) | Yield |
|---|---|---|---|---|---|---|---|---|---|---|---|
| 1 | 0.09 | 0.073 | 16 | 4 | 0.4 | 8.2-7.8 | 42 | 25 | N/A | 3.9 | 12% |
| 2 | 0.90 | 0.73 | 160 | 40 | 4.0 | 8.2-7.8 | 88 | 200 | N/A | 14 | 36% |
| 3 | 0.09 | 0.073 | 16 | 4 | 0.3 | 8.6-7.9 | 64 | 25 | 6.8/1 | 46.5 | 149% |
| 4 | 0.11 | 0.073 | 16 | 4 | 0.3 | 8.6-7.8 | 64 | 25 | 15.8/1 | 45.5 | 146% |
| 5 | 1.10 | 0.735 | 160 | 40 | 2.9 | 8.7-7.9 | 26 | 250 | 15.0/1 | 32.7 | 104% |
| 6 | 2.75 | 1.838 | 400 | 100 | 7.0 | 8.7-8.1 | 40 | 660 | 44.2/1 | 33.8 | 113% |
| 7 | 5.50 | 3.675 | 800 | 200 | 14.0 | 8.7-8.1 | 45 | 1285 | 77.9/1 | 32 | 105% |
| 8 | 2.75 | 1.838 | 400 | 100 | 7.0 | 8.6-8.1 | 46 | 675 | 2.5/1 | 22.4 | 77% |
| 9 | 2.00 | 1.342 | 320 | 80 | 5.5 | 8.6-7.8 | 19 | 684 | 7.1/1 | 17.1 | 81% |

In Table 8, PEG-pNP is 10 kDa-PEG-pNP (assumed MW: 10,000 Dalton, assumed 100% activation), buffer is amount of phosphate buffer (0.5 M) added to maintain the pH of the reaction and pH is observed pH range during the coupling reaction. The ratio of the amounts of PSC to GSC after the completion of the coupling reaction was measured using HPLC. All calculations incorporate a dry weight purity of 73.5% purity for GSC (CMP-SA-glycine) as a disodium salt (MW=673) and assume a molecular weight of 10,000 Daltons for the 10 kDa-mPEG-pNP and 10,700 Daltons for the CMP-SA-PEG-10 kDa. All reactions were performed between about 19 and about 20° C. The mass and moles of GSC added to each reaction was corrected for the actual reagent purity. Rkt time is total reaction time. The concentration of the PSC after the reaction was complete as determined by HPLC. Conversion yield was based on the ratio of amounts of PSC (HPLC) to GSC (amount used). Reactions 1 through 4 were analyzed by RP-HPLC using CMP-SA-PEG-10 kDa as the calibration standard. Reactions 5 through 10 used CMP-SA-glycine as the calibration standard.

The data indicates that an initial pH of 8.6-8.7 of the reaction mixture was critical at achieving the highest conversion yields (Table 8). The optimum pH range throughout the process was between about 8.0 and 8.8. When the pH dropped below 8.0, the reaction slowed dramatically resulting in poor conversion yields. Care was taken to not allow the pH to fall below 7.0 as CMP-SA-Glycine and CMP-SA-PEG decomposes under these conditions due to hydrolysis to form CMP, sialic acid-glycine and sialic acid-PEG (FIG. 3). At a pH above 8.8, the 10 kDa-mPEG-pNP reagent hydrolyzed rapidly leading to low conversion yields (FIG. 1, Table 8: reactions 1 and 2). Certain CMP-SA-Glycine reagents contained residual NaOH (to insure the sodium salt form of this reagent) that created solutions with a pH >10 when dissolved in water. Therefore, the first steps in setting up the coupling reaction involved dissolving the CMP-SA-Glycine in water required the addition of buffer (sodium phosphate, pH 4.6) to lower the pH to about 8.6 prior to addition of mPEG-pNP. After pH adjustment, mPEG-pNP was added to the reaction mixture and the reaction mixtures were kept at ambient temperature (about 19-20° C.). As the reactions proceeded, the added phosphate buffer prevented the pH from dropping below 8.0 as the acidic species p-nitrophenol was formed. However, if the pH did fall to 8.0, sodium hydroxide (0.1 N) was used to raise the pH to 8.6.

It was occasionally difficult to achieve a stable pH reading due to the viscosity of the reaction mixture, especially for the reactions involving the larger PEGs. Higher mPEG-pNP concentrations were used for the larger PEGs (20 kDa and glycerol-40 kDa) to increase yields. Concentrations of 100 mg mPEG-pNP/mL reaction mixtures were used with CMP-SA-glycine concentrations of 3.3 (Tables 9 and 10). Conversion yields increased by about 10% when higher PEG concentrations were used (Table 10, reactions 1-4).

did not dissolve readily. This affected the rate and conversion yield of the reaction. Different buffers were also examined as part of the PEGylation optimization process using only water as a solvent. However, both sodium bicarbonate buffer (10 mM, pH 8.1) and sodium borate buffer (10 mM, pH 8.6) resulted in lower conversion yields (Table 10).

TABLE 9

Coupling reaction results for CMP-SA-PEG-20 kDa[1]

| Rkt No | 10-kDa-PEG-pNP (mmol) | GSC (mmol) | THF (mL) | Water (mL) | Buffer (mcL) | pH Range | Rkt Time (hrs) | Final Volume (mL) | PSC/GSC Ratio | Conc. CMP-SA-PEG (mg/mL) | Yield |
|---|---|---|---|---|---|---|---|---|---|---|---|
| 1 | 0.50 | 0.327 | 80 | 20 | 1200 | 8.7-8.3 | 29 | 200 | 22.7 | 31.8 | 96% |
| 2 | 1.0 | 0.656 | 160 | 40 | 2000 | 8.6-8.2 | 39 | 476 | 21 | 25.1 | 87% |
| 3 | 0.11 | 0.073 | 0 | 30 | 120 | 8.7-7.8 | 25 | 45 | 20 | 29.4 | 84% |
| 4 | 0.55 | 0.365 | 0 | 100 | 800 | 8.4-8.0 | 24 | 220 | 20 | 29.4 | 84% |

The coupling reactions required between about 24 and about 72 hrs to completion. Reactions were monitored using RP-HPLC. Reaction times as long as about 48 to about 72 hrs were required for some reaction conditions, especially those involving larger PEG molecules.

No significant difference in conversion yields was observed when different ratios of coupling reagents (GSC and 40 kDa-glycerol-mPEG-p-nitrophenyl carbonate) were used. Table 10 shows that a reaction with 1.4 mol eq. GSC/1 mol eq activated PEG gave the same result as a reaction containing 1.1 mol eq. activated PEG/mol eq GSC under otherwise identical conditions (reactions 2 and 3). Although it may be possible to increase the conversion yield using a much larger excess of 40 kDa-glycerol-mPEG-p-nitrophenyl carbonate, the economics of the process would become much less favorable.

The PEGylation reaction to produce CMP-SA-PEG-20 kDa and CMP-SA-glycerol-PEG-40 kDa was also performed in 100% water (no THF) (Table 9). It was initially assumed that in the absence of THF, the reaction process might proceed more quickly and the process itself would no longer require rotary evaporation as a unit operation. The results indicate that an aqueous reaction is possible. However, for the 20 kDa reaction, extensive pH monitoring and adjustment with 0.1 N NaOH was required, especially during the initial hours of the reaction. AS a result, no significant time savings were observed. In addition, when 100% water was used to produce the CMP-SA-glycerol-PEG-40 kDa, the glycerol-mPEG-p-nitrophenylcarbonate In Table 9, GSC is CMP-SA-Glycine and PSC is CMP-SA-PEG-20 kDa. All calculations incorporate a dry weight purity of 73.5% purity (HPLC) for the GSC as a disodium salt (673 Daltons) and assume a molecular weight of 20,000 Daltons and 100% activation for the 20 kDa mPEG-pNP and a moleculare weight of 20,700 Daltons for the CMP-SA-PEG-20 kDa. The mass and moles of GSC added to each reaction was corrected for the actual reagent purity. "Buffer" indicates the amount of phosphate buffer (0.5 M) added to maintain the pH of the reaction. "pH range" indicates the observed pH range during the coupling reaction. "Rkt time" is total reaction time. The ratio of the amounts of PSC to GSC was determined after the completion of the coupling reaction by HPLC. The concentration of the PSC after the reaction was complete as determined by HPLC. Conversion yields are based on the ratio of amounts of PSC to GSC as determined by HPLC.

TABLE 10

Coupling Reaction Results for CMP-SA-glycerol-PEG-40 kDa

| Rkt No | 10-kDa-PEG-pNP (mmol) | GSC (mmol) | THF (mL) | Water (mL) | Buffer (mcL) | pH Range | Rkt Time (hrs) | Final Volume (mL) | PSC/GSC Ratio | Conc. CMP-SA-PEG (mg/mL) | Yield |
|---|---|---|---|---|---|---|---|---|---|---|---|
| 1 | 0.083 | 0.066 | 32 | 8 | 250 | 8.7-8.4 | 21 | 60 | 2.54 | 30.08 | 67% |
| 2 | 0.022 | 0.020 | 16 | 4 | 90 | 8.7-8.4 | 75 | 25 | 1.38 | 17.36 | 53% |
| 3 | 0.020 | 0.024 | 16 | 4 | 120 | 8.7-8.4 | 75 | 35 | 0.77 | 12.56 | 54% |
| 4 | 0.11 | 0.10 | 40 | 10 | 500 | 8.7-8.1 | 68 | 165 | 3.57 | 17.92 | 73% |
| 5 | 0.44 | 0.40 | 160 | 40 | 2000 | 8.9-8.3 | 66 | 678 | 2.73 | 13.72 | 57% |
| 6 | 0.010 | 0.012 | 0 | 10 | 50 | ~8.2 | 20 | 10 | 0.68 | 15.5 | 38% |
| 7 | 0.015 | 0.010 | 0 | 10 | 40 | ~8.2 | 22 | 10 | 1.23 | 19.16 | 47% |
| 8 | 0.010 | 0.012 | 0 | 0[10] | 0 | ~8.6 | 20 | 10 | 0.46 | 17.18 | 42% |
| 9 | 0.015 | 0.010 | 0 | 0[10] | 0 | ~8.6 | 22 | 10 | 0.95 | 17.09 | 42% |

In Table 10, GSC is CMP-SA-Glycine and PSC is CMP-SA-PEG-40 kDa. All calculations incorporate a dry weight purity of 73.5% purity for the GSC as a disodium salt (673 Daltons) and assumed a molecular weight of 42,843 Daltons for the 40 kDa mPEG-pNP (90% activation) and a molecular weigh of 40,700 Daltons for the CMP-SA-glycerol-PEG-40 kDa. The mass and moles of GSC added to each reaction was corrected for the actual reagent purity. "Buffer" indicates the amount of phosphate buffer (0.5 M) added to maintain the pH of the reaction. "pH range" indicates the observed pH range during the coupling reaction. "Rkt time" is total reaction time. The ratio of the amounts of PSC to GSC was determined after the completion of the coupling reaction by HPLC. The concentration of the PSC after the reaction was complete as determined by HPLC. Conversion yields are based on the ratio of amounts of PSC to GSC as determined by HPLC. Reactions 8 and 9 were performed using 10 mL of 10 mM Na borate buffer, pH 8.6 as a replacement for sodium phosphate buffer.

Example 6

Exemplary Processes for the Production of CMP-SA-PEGs 6.1. Exemplary Process for the Production of CMP-SA-PEG-10 kDa CMP-SA-Glycine was dissolved in water and THF (1 part to 4 parts) at a concentration of 3.4 mM. The solution was adjusted to pH 8.6 with sodium phosphate and then 10 kDa mPEG-pNP reagent was added (1.5 mole equivalents relative to actual moles of CMP-SA-Glycine). The reaction was stirred at room temperature for 20-48 hours while maintaining the pH at 8.6. The reaction was monitored by RP-HPLC and when complete, and the reaction mixture was concentrated by rotary evaporation to remove the THF. The concentrated aqueous reaction mixture was diluted with water (400 mL) to a final volume that was 1.7 times the original reaction volume. The conductivity was measured and was below 1 mS/cm. The dilute product solution was loaded onto a Q-sepharose Big Beads column (10 g of PEG reagent per liter of resin with at least a 10 cm resin bed height) at a flow rate of 50 cm/hr. Non-binding material was washed from the column with 2 CV of water. The SA-PEG-10 kDa impurity was eluted from the column with 5 mM $NaHCO_3$ (0.6 CV) at a flow rate of 100 cm/hr. The pure product, CMP-SA-PEG-10 kDa, was eluted with 30 mM $NaHCO_3$ (3 CV) also at a flow rate of 100 cm/hr. The product fraction started when the UV271 reading rose above the base line following the SA-PEG impurity peak, and ended at about 5% of the peak maximum at the trailing side of the product peak as shown in FIG. 4. The pooled product was cooled to 4° C. and concentrated 3-fold (to a product concentration of approximately 14 g/L) using a tangential flow filtration system that used 1 kDa regenerated cellulose membranes. Diafiltration of the retentate with 4° C. water (4 retentate volumes) was used to remove the salt and was continued until the permeate conductivity approached that of feed water. The purified CMP-SA-PEG-10 kDa solution was then frozen and freeze-dried to dryness.

6.2. Exemplary Process for the Production of CMP-SA-PEG-20 kDa

CMP-SA-Glycine was dissolved in water and THF (1 part to 4 parts) at a concentration of 3.3 mM. The solution was adjusted to pH 8.6 with sodium phosphate and the 20 kDa mPEG-pNP reagent (1.5 mole equivalents relative to actual moles of CMP-SA-Glycine) was added. The reaction was stirred at room temperature for 20-48 hours while maintaining the pH at 8.6. The reaction was monitored by RP-HPLC and when the reaction was complete, the reaction mixture was concentrated by rotary evaporation to remove the THF. The concentrated aqueous reaction mixture was diluted with water (300 mL) to a final volume that was 2.4 times greater than the original total reaction volume. The conductivity was measured and verified to be less than 0.8 mS/cm. The diluted product solution was loaded onto a Q-sepharose Big Beads column (10 g of PEG reagent per liter of resin with at least a 10 cm resin bed height) at a flow rate of 50 cm/hr. Non-binding material was washed from the column with 2 CV of water. The SA-PEG-10 kDa impurity was eluted from the column with 2 mM $NaHCO_3$ (1 CV) at a flow rate of 100 cm/hr. The pure product was eluted with 30 mM $NaHCO_3$ (3 CV) also at 100 cm/hr (FIG. 6). The product fraction that was collected began when the UV271 reading rose above the base line following the SA-PEG impurity peak, and ended at about 5% of the maximum product peak on the trailing side of that peak. The pooled product was cooled to 4° C. and concentrated 4-fold (to a product concentration of approximately 21 g/L) using a tangential flow filtration system that contained 1 kDa regenerated cellulose membranes. Diafiltration of the retentate with 4° C. water (4 retentate volumes) was used to remove the salt and was continued until the permeate conductivity approached that of feed water. The purified CMP-SA-PEG-20 kDa solution was frozen and freeze-dried to dryness.

6.3. Exemplary Process for the Production of CMP-SA-glycerol-PEG-40 kDa

CMP-SA-Glycine was dissolved in water and THF (1 part to 4 parts) at a concentration of 2 mM. The solution was adjusted to pH 8.6 with sodium phosphate and the 40 kDa mPEG-pNP reagent (1.1 mole equivalents relative to actual moles of CMP-SA-Glycine) was added. The reaction was stirred at room temperature for 60-66 hours while maintaining the pH at 8.6. The reaction was monitored by RP-HPLC and when the reaction was complete, the reaction mixture was concentrated by rotary evaporation to remove the THF. The concentrated aqueous reaction mixture was diluted with water (600 mL) to adjust the volume to 3.4 times the original total reaction volume and the conductivity to less than 0.5 mS/cm. The dilute product solution was loaded onto a Q-sepharose Big Beads column (5 g of PEG reagent per liter of resin with at least a 10 cm resin bed height) at a flow rate of 30 cm/hr. Non-binding material was washed from the column with 2 CV water. The SA-PEG-10 kDa impurity was eluted from the column) with 2 mM $NaHCO_3$ (1 CV) at a flow rate of 150 cm/hr. The pure CMP-SA-glycerol-PEG-40 kDa was eluted with 30 mM $NaHCO_3$ (3 CV) also at 150 cm/hr (FIG. 7). The product fraction started when the UV271 reading rose to 20% of the product peak max absorbance (allowing for removal of the SA-PEG impurity shoulder), and ended at about 5% of the peak maximum at the trailing side of the product peak (FIG. 7). The pooled product was cooled to 4° C. and concentrated 4-fold using a tangential flow filtration system that contained 1 kDa regenerated cellulose membranes (to a product concentration of approximately 6 g/L). Further concentration was limited by the large working volume required by the system. Diafiltration of the retentate with 4° C. water (4 retentate volumes) was used to remove the salt and was continued until the permeate conductivity approached that of feed water. The purified CMP-SA-glycerol-PEG-40 kDa solution was frozen and freeze-dried to dryness.

Example 7

Optimization of Anion Exchange Conditions

Q-Sepharose Big Beads resin from GE Healthcare was selected as the resin of choice for the purification of the CMP-SA-PEGs because the resins low cost, high binding capacity, high linear flow rates and quaternary amine ion binding functionality. Different counterion forms of the resin were examined for their ability to bind CMP-SA-PEGs including chloride, hydroxide, phosphate and bicarbonate ions. It was observed that the CMP-SA-PEGs had a low binding avidity for this resin most likely due to the large PEG moieties on the reagent that interfere with reagent-resin ion interactions. As a result, the conductivities of the load solutions was chosen to be below 1 mS/cm.

The CMP-SA-PEGs did not bind to the chloride form of the resin but did bind to the hydroxide, phosphate and bicarbonate forms (Table 11). The hydroxide form of the resin could not be used in processing since when the CMP-SA-PEG was eluted using sodium chloride, no resolution of the SA-PEG could be achieved and the pH of the solution became very basic. The increase in pH caused the decomposition of the CMP-SA-PEG (Table 11). Elution of the product from the phosphate form of the resin using sodium phosphate (pH 7.5 or pH 8.0) provided poor resolution of the contaminants (Table 11).

Figure 5:
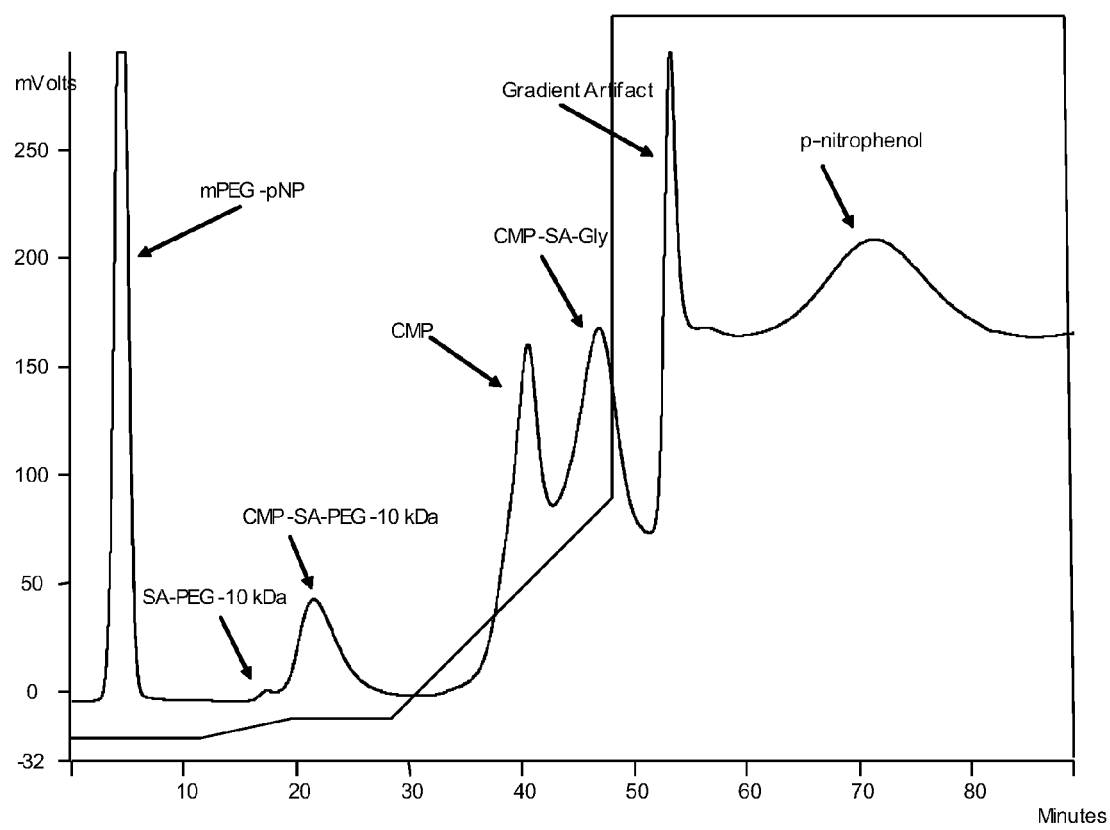
FIG. 5 is an anion exchange chromatogram obtained during the purification of CMP-SA-PEG-10 kDa using a Q Sepharose Big Beads chromatography column and sodium bicarbonate gradient elution as described in Example 7 (0-30 mM over 3 CV; 30 mM for 2 CV; 30 mM to 280 mM over 5 CV; and 1 M for 10 CV).

Only the elution of the product from the bicarbonate form of the Q-Sepharose Big Bead resin with sodium bicarbonate as the elution buffer provided the separation of many of the related contaminants in the feed solution including CMP, SA-PEG and CMP-SA-Glycine (FIG. 5). A shallow NaHCO$_3$ gradient or small step elution method was necessary to selectively elute the CMP-SA-PEGs from SA-PEG that may form during the reaction or production process. Only a very small step increase in conductivity was required to elute SA-PEG and CMP-SA-PEG (<30 mM NaHCO$_3$, <2.7 mS/cm). However, the other binding reaction components (CMP, CMP-SA-Glycine, p-nitrophenol) were all eluted only when much higher NaHCO$_3$ concentrations were used.

In Table 11, the conductivity of the concentrated and diluted coupling reaction mixture solution was <1.0 mS/cm. Resolution means separation of CMP-SA-PEG-10 kDa product from other related contaminants (e.g., CMP, GSC, SA-PEG, PEG and p-nitrophenol). PEG and p-nitrophenol were easily separated from the product by all of the methods except when the resin was in the chloride ion form. The phosphate buffer at pH 8.0 was also examined by the same elution methods. Similar results were observed as seen for the phosphate buffer at pH 7.5.

Step Elution Optimization.

Using the HCO$_3^-$ form of the Q Sepharose Big Beads resin, step elution conditions with NaHCO$_3$ buffer were carefully optimized for each CMP-SA-PEG product. The resolution between the early eluting SA-PEG impurity peak and the product was maximized. Small steps from water to low NaHCO$_3$ concentrations (30 mM, 10 mM, 5 mM) were investigated for CMP-SA-PEG-10 kDa as described in Table 12. Baseline resolution was achieved between SA-PEG-10 kDa and the product with an initial step to 5 mM NaHCO$_3$. Although the product also eluted at 5 mM NaHCO$_3$ concentration, the product peak elution profile was very broad. Therefore after 0.6 CV at 5 mM, the gradient was immediately stepped to 30 mM NaHCO$_3$. The pure CMP-SA-PEG-10 kDa was efficiently collected in approximately 1.5 CV at pH 8.3-8.6 as shown in FIG. 3. The more tightly bound CMP, CMP-SA-Gly and p-nitrophenol impurities were eluted with a step elution to 1 M NaHCO$_3$. The SA-PEG-10

TABLE 11

Purification of CMP-SA-PEG-10 kDa with a Q-Sepharose Big Beads Column using Various Elution Conditions

| Resin | Elution Salt | Elution Method | Resolution |
|---|---|---|---|
| Hydroxide | NaCl | Linear gradient (no buffer in the 1 M sodium chloride) Note: Column elution pH was >11 resulting in decomposition of the CMP-SA-PEG | Poor resolution of CMP and GSC; no resolution of SA-PEG |
| Phosphate | sodium phosphate (pH 7.5) | Linear gradients; 0-15 mM Na phosphate, pH 7.5 in 6 CV; then, 15-140 mM Na Phosphate, pH 7.5 in 5 CV; and then 0.5 M Na Phophate, pH 7.5. | Poor resolution of CMP and GSC; no resolution of SA-PEG |
| Phosphate | sodium phosphate (pH 7.5) | Linear gradients; 0-30 mM Na phosphate, in 6 CV, 30-280 mM Na phosphate in 5 CV, 0.5 M Na phosphate. | Poor resolution of CMP and GSC; no resolution of SA-PEG |
| Bicarbonate | NaCl | Linear gradient; 0-0.5 M NaCl (no buffer) in 5 CV | Poor resolution of CMP and GSC; no resolution of SA-PEG |
| Bicarbonate | NaCl | Linear gradient; 0-0.3 M NaCl (no buffer) over 6 CV | Partial resolution of CMP and GSC; no resolution of SA-PEG |
| Bicarbonate | NaCl | Step elution from 0 to 30 mM NaCl (no buffer); then linear gradient 30-250 mM NaCl over 5 CV | Separation of CMP and GSC; no resolution of SA-PEG |
| Bicarbonate | sodium phosphate (pH 8.0) | Linear gradient; 0-30 mM Na phosphate, pH 8 over 6 CV, then 30-280 mM Na phosphate in 5 CV | Good resolution of CMP and GSC; no separation of SA-PEG |
| Bicarbonate | sodium bicarbonate | Step from 0 to 0.01% NaHCO$_3$ for 1.5 CV; then a step to 0.1% NaHCO$_3$ for 1.5 CV; then a linear gradient from 30 mM-280 mM NaHCO$_3$ over 5 CV | Good resolution of CMP and GSC; no resolution of SA-PEG |
| Bicarbonate | sodium bicarbonate | Linear gradient; 0-30 mM NaHCO$_3$ in 3 CV, then 30 mM NaHCO$_3$ for 2 CV, then linear gradient from 30-280 mM NaHCO$_3$ over 5 CV | Excellent resolution of CMP and GSC; partial resolution of SA-PEG |
| Bicarbonate | sodium bicarbonate | Step elution; 0-5 mM NaHCO$_3$ over 0.6 CV, then step to 30 mM NaHCO$_3$ and hold for 3 CV, then step to 1 M NaHCO$_3$ or NaOH | Excellent resolution of all contaminants including SA-PEG |
| Chloride | — | CMP-SA-PEG does not bind | — | kDa peak was also collected, desalted (on a G-25 column, not described) and freeze-dried. Analysis of the solid by $^1$H-NMR verified its structure.

Figure 8:
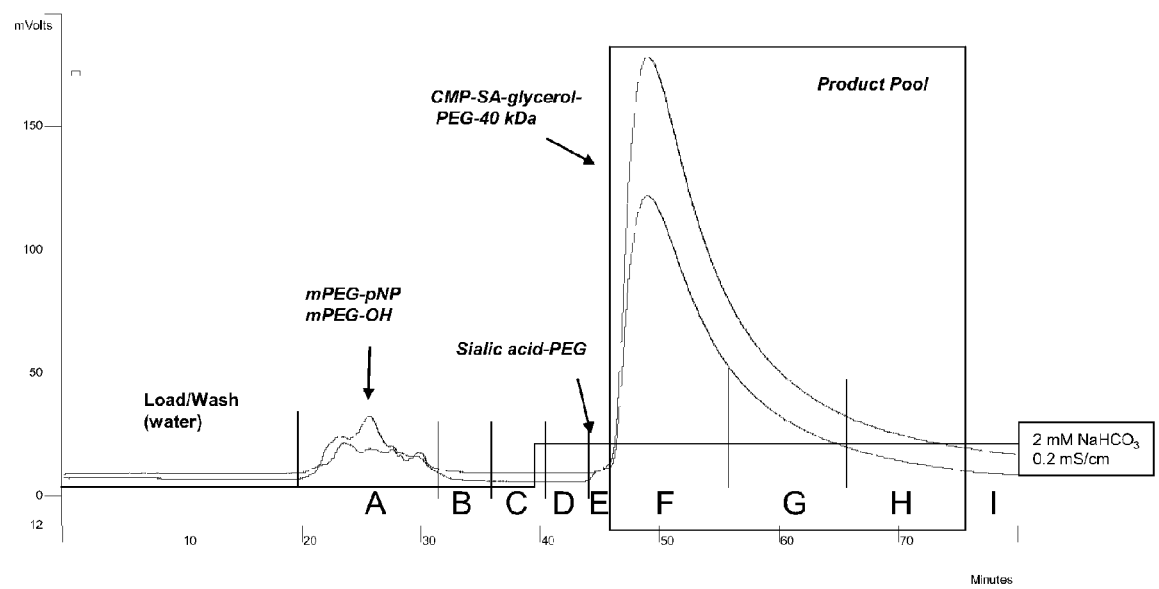
FIG. 8 is an anion exchange chromatogram obtained during the purification of CMP-SA-PEG-40 kDa using a Q Sepharose Big Beads chromatography column and a sodium bicarbonate elution as described in Example 7 (2 mM NaHCO$_3$ for 4 CV).

In order to achieve the same baseline separation between the SA-PEG-20 kDa and the CMP-SA-PEG-20 kDa product, an initial step elution to 2 mM NaHCO$_3$ was required (FIG. 6). The product also began to elute at 2 mM NaHCO$_3$. To avoid a very broad elution product peak, the gradient was stepped to 30 mM NaHCO$_3$ after only 1 CV at 2 mM sodium bicarbonate. The pure product was collected in approximately 1.5 CV at pH 7.8 (FIG. 5). The SA-PEG-20 kDa peak was also collected, desalted (on a G-25 column, not described) and freeze-dried. Analysis of the solid by $^1$H-NMR verified its structure.

tially resolved as a very small shoulder on the leading edge of the product peak (FIG. 8). When the CMP-SA-glycerol-PEG-40 kDa was collected using 2 mM sodium bicarbonate, a broad elution peak (3 CV) was collected. The pH of this elution peak was only 6.5 which caused product decomposition.

Therefore, the SA-PEG-40 kDa was eluted using a step elution with 2 mM sodium bicarbonate (1 CV). The product was then eluted by increasing the step elution with 30 mM NaHCO$_3$ to quickly elute the product as shown in FIG. 7. Using these conditions, the CMP-SA-glycerol-PEG-40 kDa product was collected from the column in 2 CV with a pH of 7.4. Further pH adjustment was not necessary. The unusual peak shape observed in FIG. 5 could be prevented

TABLE 12

Optimization of Q-Sepharose Big Beads Elution Conditions for CMP-SA-PEG-10 kDa

| | PEG Load* (grams PEG/L resin) | Volumetric Flow Rate Load/wash/Elution (mL/min) | Linear Flow Rate Load/Elution (cm/hr) | Gradient | Comments |
|---|---|---|---|---|---|
| 1 | 11 g PEG/L resin | 1.7/3.4/3.4 | 19.2/38.4 | Water wash 3.2 CV, 10 mM NaHCO$_3$ for 2.5 CV, 10-30 mM NaHCO$_3$ over 1.5 CV, 30 mM NaHCO$_3$ for 1 CV, 30-280 mM NaHCO$_3$ in 5 CV, 1 M NaHCO$_3$ for 2 CV. | Some resolution of SA-PEG and CMP-SA-PEG, but product elution begins at 10 mM NaHCO$_3$. |
| 2 | 11 g PEG/L resin | 1.7/3.4/3.4 | 19.2/38.4 | Water wash 3.2 CV, 5 mM NaHCO$_3$ for 2 CV, 10 mM NaHCO$_3$ for 2 CV, 20 mM NaHCO$_3$ for 2 CV, 30 mM NaHCO$_3$ for 2 CV, 30-280 mM NaHCO$_3$ over 1 CV, 280 mM-1 M NaHCO$_3$ over 1 CV, 1 M NaHCO$_3$ for 2 CV. | Good resolution of SA-PEG and CMP-SA-PEG. Product elution begins at 10 mM NaHCO$_3$. |
| 3 | 11 g PEG/L resin | 1.7/3.4/8.9 | 19.2/100 | Water wash 2.2 CV, 30 mM NaHCO$_3$ for 3 CV, 30-280 mM NaHCO$_3$ over 1 CV, 280 mM-1 M NaHCO$_3$ over 1 CV, 1 M NaHCO$_3$ for 2 CV. | Poor resolution of SA-PEG and CMP-SA-PEG. |
| 4 | 22 g PEG/L resin | 1.7/3.4/3.4 | 19.2/38.4 | Water wash 2.2 CV, 30 mM NaHCO$_3$ for 3 CV, 30-280 mM NaHCO$_3$ over 1 CV, 280 mM-1 M NaHCO$_3$ over 1 CV, 1 M NaHCO$_3$ for 2 CV. | No resolution of SA-PEG and CMP-SA-PEG. |
| 5 | 11 g PEG/L resin | 1.7/8.9/8.9 | 19.2/100 | Water wash 2.2 CV, 5 mM NaHCO$_3$ for 0.6 CV, 30 mM NaHCO$_3$ for 3 CV, 1 M NaHCO$_3$ for 7 CV. | Best separation of SA-PEG and CMP-SA-PEG. |
| 6 | 8.2 g PEG/L resin | 1.7/8.9/8.9 | 19.2/100 | Water wash 2.2 CV, 5 mM NaHCO$_3$ for 0.6 CV, 30 mM NaHCO$_3$ for 3 CV, 30-280 mM NaHCO$_3$ over 1 CV, 280 mM-1 M NaHCO$_3$ over 1 CV, 1 M NaHCO$_3$ for 7 CV. | Best separation of SA-PEG and CMP-SA-PEG. Inadvertent underloading of column. Collected and confirmed identity of all peaks by RP-HPLC. |
| 7 | 10 g PEG/L resin | 65/130 | 50/100 | Water wash 2.2 CV, 5 mM NaHCO$_3$ for 0.6 CV, 30 mM NaHCO$_3$ for 3 CV, 1 M NaHCO$_3$ for 7 CV. | Best separation of SA-PEG and CMP-SA-PEG. FIG. 3. |

In Table 12, Q Big Beads Column is GE XK-26 (2.6 cm×18.8 cm, 100 mL), bicarbonate ion form for experiments 1-6 and GE BPG 100/500 Column (10 cm×26 cm, 2 L) bicarbonate form for experiment 7. PEG load was calculated from the mass of 10 kDa-mPEG-pNP in grams used in the source reaction multiplied by the fraction of the final reaction volume that was loaded on the column divided by the column volume in liters The CMP-SA-glycerol-PEG-40 kDa bound very weakly to the Q-Sepharose Big Beads resin. The product and SA-PEG by-product were both eluted using a step elution to 2 mM NaHCO$_3$. The SA-PEG-40 kDa impurity was parby shortening the 2 mM NaHCO$_3$ step from 1 full column volume (CV) of elution to 0.5 CV, as was done with the 10 kDa product (FIG. 4). Process step recoveries for this unit operation were routinely found to be in excess of 95 as determined by RP-HPLC (FIG. 7). The SA-PEG-40 kDa peak was also collected and freeze-dried. Analysis of the solid by $^1$H-NMR verified its structure.

Process Parameters. The rotavapped reaction mixtures of the CMP-SA-PEG-10 kDa and 20 kDa products were preferably diluted until the conductivities were reduced to less than 1 and 0.8 mS/cm, respectively. In addition, the pH of the solution were preferably between 7.1-7.6 to ensure complete capture of the product. The diluted solutions were loaded onto the AEX column at concentrations that corresponded to 10 g of activated mPEG-pNP starting reagent used for the reaction per liter of AEX resin. Higher product column loads could be used for the CMP-SA-PEG-10 kDa product (22 g mPEG-pNP/L resin) but resolution between the SA-PEG and CMP-SA-PEG-10 kDa was lost (Table 11).

The conductivity of the rotavaped CMP-SA-glycerol-PEG-40 kDa reaction mixtures were preferably reduced to below 0.5 mS/cm by water dilution. In addition, the pH of the solution was preferably between 7.1-7.6 to insure complete capture of the product. A small-scale loading study indicated that about 1 liter of Q-Sepharose Big Beads resin is required for each 5 grams of 40 kDa-mPEG-pNP starting reagent used in the reaction. Thus a 4 L column should be sufficient to capture the CMP-SA-glycerol-PEG-40 kDa reaction product that began with 20 g of 40 kDa-mPEG-pNP. This is about 70% of the maximal loading capacity for the AEX resin using these elution conditions. There were no observed differences in the performance of the chromatography with column bed heights between 15 and 28 cm.

The concentrated, diluted reaction mixtures were loaded onto the AEX column at linear flow rates of 15-50 cm/hour (corresponding to 20-65 mL/min on a 2 L column). In all cases the residence time of the load solution on the column was approximately 15 minutes. Using a 2 L AEX column, wash and elution flow rates of 100-150 cm/hr (130-200 mL/min for the 2 L column) were used for all three CMP-SA-PEG products. Therefore, the total unit operation time including reaction mixture loading and product elution was less than 1.5 hrs (FIGS. 3, 5 and 7). Higher elution flow rates, up to 200 cm/hr, were used with no observed loss in resolution between the SA-PEG-20 kDa and CMP-SA-PEG-20 kDa product.

Example 8

Optimization of Ultrafiltration/Diafiltration Desalting Step (TFF)

The CMP-SA-PEG ion-exchange elution pools were concentrated and desalted using ultrafiltration/diafiltration (TFF). The TFF system used Millipore Pellicon-2 flat sheet membranes (1 kDa MWCO; regenerated cellulose membranes) to desalt the feed solution and retain the products. Exemplary Tangential Flow Filtration Process.

CMP-SA-PEG-10 kDa ion-exchange product pool (1500 mL, FIG. 4) and CMP-SA-PEG-20 kDa ion-exchange product pool (FIG. 6) were both desalted using the Pellicon 2 "MINI" system with 3×0.1 m$^2$ membranes (Table 1) using a peristaltic pump. Transmembrane pressures of approximately 22 psi were used which created a flux of approximately 3.7 LMH.

Due to the large elution volumes from the AEX elution pools for CMP-SA-glycerol-PEG-40 kDa (FIG. 7), the elution pools were desalted using 2×0.5 m$^2$ membranes (Table 4). A peristaltic pump was used for this system which created a flux rate of 3 LMH with a TMP of 20 psi. The Q-sepharose Big Beads elution product pool was chilled in an ice bath during processing to prevent the decomposition of CMP-SA-glycerol-PEG-40 kDa as a result of the heat created from the pump.

The retentate solutions processed on the MINI system were concentrated to 500 mL (3 fold for CMP-SA-PEG-10 kDa, 4 fold for CMP-SA-PEG-20 kDa) corresponding to product concentrations of 14.3 g/L and 21 g/L respectively. No product breakthrough was observed in any of the permeate samples (RP-HPLC). Due to the large system hold-up volume of the 0.5 m$^2$ system (approximately 400 mL for 2 membrane cartridges) the minimum retentate volume that could be achieved was only 1 L (4-6 fold concentration). The resulting product concentration was quite dilute at approximately 5 g/L, which was much lower than the 20 g/L achieved for the smaller 20 kDa product.

After concentration, the retentates were each diafiltered at constant volume using 4 diavolumes of chilled water (2 L for the 10 and 20 kDa product; 4 L for the 40 kDa product). Permeate samples were collected throughout the concentration and diafiltration process and the pH and conductivity were recorded. The diafiltration was complete when the conductivity of the permeate solutions approached that of the water used for diafiltration (<50 microS/cm).

Table 8:

The final diafiltered retentate pools were analyzed by RP-HPLC and freeze dried to provide a white powder over a period of approximately 3 days. The final freeze dried TFF products were analyzed by RP-HPLC and NMR to determine product recovery (90-95%) and purity (>90%, Tables 2, 3, 5 and 6). Overall product recoveries for the combined reaction, rotoevaporation, ion-exchange, TFF unit operations and freeze-drying were 65-77%. $^1$H-NMR verified each products structure and ICP testing indicated that each product structure was in the disodium form. ICP testing also indicated that no additional sodium salts were present.

The purity and overall yield calculations are based on estimated average masses of the mPEG's used to produce each of the CMP-SA-PEG products (10,700 for CMP-SA-PEG-10 kDa; 20,700 for CMP-SA-PEG-20 kDa; 43,347 for CMP-SA-glycerol-PEG-40 kDa) as reported by the manufacturer. Underestimation of product molecular weights results in an underreporting of product content by RP-HPLC and therefore underestimation of product purity.

What is claimed is:

1. A method of making a composition comprising a modified nucleotide sugar covalently linked to a polymeric modifying group, said polymeric modifying group comprising at least one linear or branched poly(alkylene oxide) moiety, said method comprising:
    (i) contacting a reaction mixture comprising said modified nucleotide sugar with a Q-sepharose anion exchange resin;
    (ii) eluting said modified nucleotide sugar from said Q-sepharose anion exchange resin using a bicarbonate buffer, wherein said eluting comprises a first step wherein said buffer comprises between about 0.01 mM and about 10 mM of bicarbonate and a second step wherein said buffer comprises between about 10 mM and about 30 mM of bicarbonate, thereby forming an eluate fraction comprising said modified nucleotide sugar; and
    (iii) desalting said eluate fraction,
    wherein said method does not comprise ultrafiltration prior to step (i), thereby forming said composition, wherein said modified nucleotide sugar comprises cytidine-monophospho-sialic acid (CMP-SA), wherein said method provides said modified nucleotide sugar in a purity between about 80% and about 100% (w/w) and wherein the linear or branched poly(alkylene oxide) moiety has a molecular weight in the range of 10-40 kDa.

2. The method of claim 1, wherein said reaction mixture has a salt conductivity of less than about 5 mS/cm.

3. The method of claim 1, wherein said desalting is accomplished using membrane filtration.

4. The method of claim 3, wherein said membrane filtration is tangential flow filtration (TFF).

5. The method of claim 3, wherein said membrane filtration reduces the volume of said eluate fraction.

6. The method of claim 3, wherein said membrane filtration results in reduced salt conductivity of said eluate fraction compared to said salt conductivity prior to said membrane filtration.

7. The method of claim 6, wherein said reduced salt conductivity of said eluate fraction is between about 10 μS/cm and about 200 μS/cm.

8. The method of claim 6, wherein said reduced salt conductivity of said eluate fraction is less than about 50 μS/cm.

9. The method of claim 1, further comprising reducing the volume of said mixture prior to step (i).

10. The method of claim 9, wherein said reducing is accomplished using rotary evaporation.

11. The method of claim 1, wherein said eluate fraction comprising said modified nucleotide sugar is subjected to freeze drying or spray drying.

12. The method of claim 1, wherein said poly(alkylene oxide) moiety is a linear or branched poly(ethylene glycol) moiety.

13. The method of claim 1, wherein said nucleotide sugar is cytidine-monophospho-sialic acid (CMP-SA) covalently linked to a linear or branched poly(ethylene glycol) moiety.

14. The method of claim 13, wherein said branched poly(ethylene glycol) moiety comprises a glycerol backbone.

15. The method of claim 1, wherein said modified nucleotide sugar is a member selected from the group consisting of:

each Q is a member independently selected from the group consisting of H, a negative charge, and a salt counter ion; and each Q' is a member independently selected from the group consisting of H, methyl, ethyl, propyl, butyl, pentyl, and hexyl.

16. The method of claim 1, wherein said method provides said modified nucleotide sugar in an overall yield from about 50% to about 90%.

17. The method of claim 1, wherein said reaction mixture comprising said modified nucleotide sugar is formed by contacting a nucleotide sugar derivative comprising a nucleotide sugar and a primary amino group with an activated poly(alkylene oxide) moiety under conditions sufficient to form a covalent bond between said amino group of said nucleotide sugar derivative and said poly(alkylene oxide) moiety.

18. The method of claim 17, wherein said nucleotide sugar derivative is CMP-SA-glycine.

19. The method of claim 17, wherein said activated poly(alkylene oxide) moiety comprises a p-nitrophenyl carbonate moiety.

20. The method of claim 17, wherein said nucleotide sugar derivative and said poly(alkylene oxide) reagent are contacted in the presence of an aqueous solvent having a pH between about 8.0 and about 8.8.

21. The method of claim 17, wherein said poly(alkylene oxide) reagent is a poly(ethylene glycol)-p-nitrophenyl carbonate.

22. A method of making a composition comprising a modified nucleotide sugar covalently linked to a polymeric modifying group, said polymeric modifying group comprising at least one linear or branched poly(alkylene oxide) moiety, said method comprising:

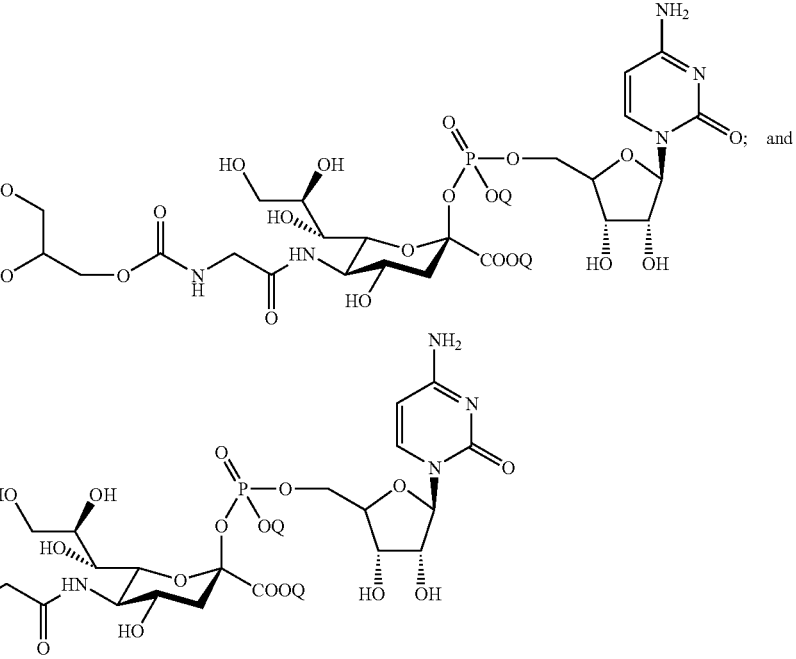

wherein each n is an integer independently selected such that the poly(alkylene oxide) moiety has a molecular weight in the range of 10-40 kDa;

(i) contacting a nucleotide sugar derivative comprising a primary amino group with an activated poly(alkylene oxide) moiety comprising a p-nitrophenyl carbonate moiety under conditions sufficient to form a covalent bond between said amino group of said nucleotide sugar derivative and said poly(alkylene oxide) moiety, wherein said contacting occurs in the presence of an aqueous solvent having a pH between about 8.0 and about 8.8, thereby forming a reaction mixture comprising said modified nucleotide sugar;

(ii) contacting said reaction mixture comprising said modified nucleotide sugar with a Q-sepharose anion exchange resin;

(iii) eluting said modified nucleotide sugar from said Q-sepharose anion exchange resin using a bicarbonate buffer, wherein said eluting comprises a first step wherein said buffer comprises between about 0.01 mM and about 10 mM of bicarbonate and a second step wherein said buffer comprises between about 10 mM and about 30 mM of bicarbonate thereby forming an eluate fraction comprising said modified nucleotide sugar;

(iv) desalting said eluate fraction using membrane filtration; and (v) removing water from said eluate fraction, wherein said method does not comprise ultrafiltration prior to step (i), thereby forming said composition wherein said modified nucleotide sugar comprises cytidine-monophospho-sialic acid (CMP-SA), wherein said method provides said modified nucleotide sugar in a purity between about 80% and about 100% (w/w), and wherein the linear or branched poly alkylene oxide) moiety has a molecular weight in the range of 10-40 kDa.

23. The method of claim 22, wherein said nucleotide sugar derivative is CMP-SA-glycine.

24. The method of claim 22, wherein said modified nucleotide sugar is CMP-SA covalently linked to a linear or branched poly(ethylene glycol) moiety.

* * * * *

UNITED STATES PATENT AND TRADEMARK OFFICE
CERTIFICATE OF CORRECTION

PATENT NO. : 9,493,499 B2  
APPLICATION NO. : 12/663748  
DATED : November 15, 2016  
INVENTOR(S) : Shawn DeFrees et al.

Page 1 of 1

It is certified that error appears in the above-identified patent and that said Letters Patent is hereby corrected as shown below:

In the Claims

Claim 19, Column 64, Line 21, "p-nitrophenyl" should read "*p*-nitrophenyl"

Claim 21, Column 64, Line 28, "poly(ethylene glycol)-p-nitrophenyl" should read "poly(ethylene glycol)-*p*-nitrophenyl"

Claim 22, Column 64, Line 36, "p-nitrophenyl" should read "*p*-nitrophenyl"

Claim 22, Column 66, Line 10, "poly alkylene oxide)" should read "poly(alkylene oxide)"

Signed and Sealed this  
Seventh Day of March, 2017

Michelle K. Lee  
*Director of the United States Patent and Trademark Office*